(12) United States Patent
During

(10) Patent No.: US 10,813,918 B2
(45) Date of Patent: Oct. 27, 2020

(54) USE OF GABOXADOL IN THE TREATMENT OF DIABETES AND RELATED CONDITIONS

(71) Applicant: Ovid Therapeutics Inc., New York, NY (US)

(72) Inventor: Matthew During, Weston, CT (US)

(73) Assignee: Ovid Therapeutics Inc., New York, NY (US)

( * ) Notice: Subject to any disclaimer, the term of this patent is extended or adjusted under 35 U.S.C. 154(b) by 62 days.

(21) Appl. No.: 16/053,081

(22) Filed: Aug. 2, 2018

(65) Prior Publication Data

US 2019/0038606 A1   Feb. 7, 2019

Related U.S. Application Data

(60) Provisional application No. 62/541,260, filed on Aug. 4, 2017.

(51) Int. Cl.
| | | |
|---|---|---|
| *A61K 31/437* | (2006.01) | |
| *A61K 9/00* | (2006.01) | |
| *A61K 45/06* | (2006.01) | |
| *A61P 3/10* | (2006.01) | |
| *A61K 31/155* | (2006.01) | |
| *A61K 31/4985* | (2006.01) | |

(52) U.S. Cl.
CPC .......... *A61K 31/437* (2013.01); *A61K 31/155* (2013.01); *A61K 31/4985* (2013.01); *A61K 45/06* (2013.01); *A61P 3/10* (2018.01)

(58) Field of Classification Search
None
See application file for complete search history.

(56) References Cited

U.S. PATENT DOCUMENTS

| | | |
|---|---|---|
| 4,278,676 A | 7/1981 | Krogsgaard-LarsenPovl |
| 4,353,910 A | 10/1982 | Perregaard |
| 4,362,731 A | 12/1982 | Hill |
| 8,569,355 B2 | 10/2013 | Laudon et al. |
| 9,339,495 B2 | 5/2016 | During |
| 9,399,034 B1 | 7/2016 | During et al. |
| 9,446,028 B2 | 9/2016 | During |
| 9,682,069 B2 | 6/2017 | During |
| 9,717,716 B2 | 8/2017 | During et al. |
| 2007/0112017 A1 | 5/2007 | Barlow et al. |
| 2007/0259912 A1 | 11/2007 | Cooper |
| 2008/0269278 A1 | 10/2008 | Lundahl et al. |
| 2009/0143335 A1 | 6/2009 | Larsen et al. |
| 2010/0029770 A1 | 2/2010 | Roberts et al. |
| 2010/0093787 A1 | 4/2010 | Lundahl et al. |
| 2011/0046090 A1 | 2/2011 | Barlow et al. |
| 2013/0251671 A1 | 9/2013 | Kaufman et al. |
| 2014/0296257 A1 | 10/2014 | Hersel et al. |
| 2016/0038469 A1 | 2/2016 | During |
| 2016/0228418 A1 | 8/2016 | During |
| 2017/0014392 A1 | 1/2017 | During |
| 2017/0014393 A1 | 1/2017 | During |
| 2017/0065572 A1 | 3/2017 | During |
| 2017/0348232 A1 | 12/2017 | During |
| 2018/0042903 A1 | 2/2018 | During |

FOREIGN PATENT DOCUMENTS

| | | |
|---|---|---|
| EP | 0000338 A2 | 1/1979 |
| EP | 0840601 B1 | 10/2001 |
| GB | 2410434 A | 8/2005 |
| WO | 9702813 A1 | 1/1997 |
| WO | 2005094820 A1 | 10/2005 |
| WO | 2009021521 A2 | 2/2009 |
| WO | 2015189744 A1 | 12/2015 |

OTHER PUBLICATIONS

Gomez et al., "GABA agonists differentially modify blood glucose levels of diabetic rats," Jpn. J. Pharmacol. 80:327-331 (1999) (Year: 1999).*
Cornier et al., "The Metabolic Syndrome", Endo. Rev. 29:777-822 (2008) (Year: 2008).*
Metabolic disease, Encyclopedia Britannica, accessed Feb. 12, 2020 at URL: britannica.com/science/metabolic-disease; pp. 1-17 (2019) (Year: 2019).*
Raptis et al., "Oral hypoglycemic agents: insulin secretagogues, alpha-glucosidase inhibitors an insulin sensitizers," Exp Clin Endrocrinol Diabetes 109(Suppl 2):S265-S287 (2011) (Year: 2011).*
Chaturvedi et al., "Fast Dissolving Films: A Review," Current Drug Delivery, 2011, vol. 8; pp. 373-380.
Ciper and Bodmeier, "Preparation and characterization of novel fast disintegrating capsules (Fastcaps) for administration in the oral cavity," Science Direct, International Journal of Pharmaceutics, 2005, vol. 303; pp. 62-71.
Boateng et al., "Characterisation of freeze-dried wafers and solvent evaporated films as potential drug delivery systems to mucosal surfaces," International Journal of Pharmaceutics, vol. 389, Issues 1-2, Apr. 15, 2010, pp. 24-31.
Deuterium labelling of the GABA agonists THIP, piperidine-4-sulphonic acid and the GABA uptake inhibitor THPO Journal of Labelled Compounds and Radiopharmaceuticals, 1982, vol. 19, No. 5; pp. 689-702.
International Search Report and Written Opinion, dated Oct. 31, 2017, corresponding to International Applicaiton No. PCT/US17/46256; 10 total pages.

(Continued)

*Primary Examiner* — Julie Ha
*Assistant Examiner* — Kristina M Hellman
(74) *Attorney, Agent, or Firm* — Carter, DeLuca & Farrell LLP

(57) ABSTRACT

Methods and compositions for treating a metabolic disease include administering gaboxadol or a pharmaceutically acceptable salt thereof to a patient diagnosed with a metabolic disease. In embodiments, administering gaboxadol or a pharmaceutically acceptable salt thereof to a patient diagnosed with a metabolic disease is effective to lower one or more of HbA1c level, fasting plasma glucose level, 2-hour oral glucose tolerance test (OGTT) result level, and random plasma glucose level. Gaboxadol or a pharmaceutically acceptable salt thereof may optionally be administered in combination with a hypoglycemic agent.

15 Claims, No Drawings

(56) References Cited

OTHER PUBLICATIONS

Richardson et al., "Extrasynaptic GABAA Receptors and Tonic Inhibition in Rat Auditory Thalamus", PLOS One, Jan. 2011, vol. 6, Issue 1, (e16508); pp. 1-5.
International Search Report and Written Opinion of the International Searching Authority, dated Apr. 24, 2018, corresponding to International Application No. PCT/US18/16602; 15 total pages.
International Search Report and Written Opinion, dated Oct. 11, 2018, corresponding to International Application No. PCT/US18/44973; 12 total pages.
Liebl, et al., "HbA1c Reduction With Basal Insulin in Type 2 Diabetes Mellitus, Insulin Therapy", Touch Briefings, European Endocrine Disease (2007); Insulin Therapy, 3 pages.
Botros et al., "Obstructive Sleep Apnea as a Risk Factor for Type 2 Diabetes", The American Journal of Medicine, vol. 122, No. 12 (Dec. 2009); pp. 1122-1127.
Pernicova et al., "Metformin—mode of action and clinical implications for diabetes and cancer", Nature Reviews| Endocrinology, vol. 10, Mar. 2014; pp. 143-156.
Johnson, "Metformin use in women with polycystic ovary syndrome", Annals of Translational Medicine, vol. 2, No. 6, (2014); 6 pages.
Cheng et al., "Inducing Anesthesia with a GABA Analog, THIP,", Anesthesiology, vol. 63, No. 2, Aug. 1985; pp. 147-151.
Ebert et al., "Treating Insomnia: Current and Investigational Pharmacological Approaches," Pharmacology & Therapeutics, vol. 112, 2006; pp. 612-629.
Evaluating and monitoring sedation, arousal, and agitation in the ICU Sessler et al., Semin. Respir. Crit. Care Med. (2013), vol. 34(2), pp. 169-178.
Walsh et al.,, "The Selective Extrasynaptic GABAA Agonist, Gaboxadol, Improves Traditional Hypnotic Efficacy Measures and Enhances Slow Wave Activity in a Model of Transient Insomnia," Sleep, vol. 30, No. 5, 2007; pp. 593-602.
Stephanie Saul, "Merck Cancels Work on a New Insomnia Medication," The New York Times, Business Day, Mar. 29, 2007; http://www.nytimes.com/2007/03/29/business/29sleep.html?.sub.-r=0; 3 pages.
Ransdell Pierson, "Update 2—Merck, Lundbeck scrap insomnia drug after trials," Rueters, (Dow Jones); 2015; 2 pages.
Egawa et al., Decreased Tonic Inhibition in Cerebellar Granule Cells Causes Motor Dysfunction in a Mouse Model of Angelman Syndrome, Neurodegenerative Disease, Science Translational Medicine, vol. 4, Issue 165 (163ra157), Dec. 5, 2012. pp. 1-10.
James K. Walsh, Ph.D., "Enhancement of Slow Wave Sleep: Implications for Insomnia," Journal of Clinical Sleep Medicine, Supplement to vol. 5, No. 2, (2009); pp. 827-832.
Wang et al., "Neurobiology of Disease—The Melatonin MT1 Receptor Axis Modulates Mutant Huntingin-Mediated Toxicity," The Journal of Neuroscience, vol. 31, No. 41, Oct. 12, 2011; pp. 14496-14507.
International Search Report and Written Opinion of the International Searching Authority, dated Aug. 26, 2015, corresponding to International Application No. PCT/US15/34018; 12 total pages.
Olmos-Serrano et al, "Defective GABAergic Neurotransmission and Pharmacological Rescue of Neuronal Hyperexcitability in the Amygdala in a Mouse Model of Fragile X Syndrome," The Journal of Neuroscience, vol. 30, No. 29, Jul. 21, 2010; pp. 9929-9938 (25 pages).
Walter Alexander, "Sleep: Gaboxadol Enhances Slow Wave Sleep," Perelman, School of Medicine, Jun. 22, 2006; 3 pages.
Brown et al., "Pharmacological Characterization of a Novel Cell Line Expressing Human α4β3δ GABAA Receptors," British Journal of Pharmacology, vol. 136, No. 7, 2002; pp. 965-974.
Deacon et al., "Effect of Short-Term Treatment with Gaboxadol on Sleep Maintenance and Initiation in Patients with Primary Insomnia," Sleep, vol. 30, No. 3, 2007; pp. 281-287.
Faulhaber et al., "The GABAA Agonist THIP Produces Slow Wave Sleep and Reduces Spindling Activity in NREM Sleep in Humans," Psychopharmacology, vol. 130, 1997; pp. 285-291.
Gaboxadol, from Wikipedia, the free encylopedia,http://en.wikipedia.org/wiki/Gaboxadol, 2014; 2 pages.
Gaboxadol, Investigational Agent—Drug Development Technology, http//www.drugdevelopment-technology.com/projects/gaboxadol—2014; 3 pages.
Gaboxadol, Bluelight, http://www.bluelight.org/vb/threads/370965-Gaboxadol—(2014); 1 page.
Glykys et al., "The Main Source of Ambident GABA Responsible for Tonic Inhibition in the Mouse Hippocampus," J Physiol, vol. 582, No. 3, 2007; pp. 1163-1178.
Hajak et al., "A 2-week Efficacy and Safety Study of Gaboxadol and Zolpidem Using Electronic Diaries in Primary Insomnia Outpatients," Sleep Medicine, vol. 10, 2009; pp. 705-712.
Jennum et al., "Sleep Disorders in Neurodegenerative Disorders and Stroke," European Handbook of Neurological Management, vol. 1, 2nd Edition, Chapter 39, Section 6—Sleep Disorders, (Ed. Gilhus et al.) Blackwell Publishing Ltd. 2011; pp. 529-543.
Lancel et al., "The GABAA Agonist THIP (Gaboxadol) Increases Non-REM Sleep and Enhances Delta Activity in the Rat," Sleep and Rhythms, NeuroReport, Rapid Science Publishers, vol. 7, No. 13; Sep. 1996; pp. 2241-2245.
Marike Lancel, "The GABAA Agonist THIP Increases Non-REM Sleep and Enhances Non-REM Sleep-Specific Delta Activity in the Rat During the Dark Period," Sleep, vol. 20, No. 12, American Sleep Disorders Association and Sleep Research Society (1997); pp. 1099-1104.
Marike Lancel, "Role of GABAA Receptors in the Regulation of Sleep: Initial Sleep Responses to Peripherally Administered Modulators and Agonists," Sleep, vol. 22, No. 1, (1999); pp. 33-42.
Lancel et al., "Effect of the GABAA Agonist Gaboxadol on Nocturnal Sleep and Hormone Secretion in Healthy Elderly Subjects," Am J. Physiol Endocrinol Metab, vol. 281; (2001), pp. E130-E137.
Larsen et al.,—Research Paper—"Intestinal Gaboxadol Absorption via PAT1 (SLC36A1): Modified Absorption in vivo Following Co-administration of L-tryptophan," British Journal of Pharmacology (BJP), vol. 157, (2009); pp. 1380-1389.
Lundahl et al., "Short-term Treatment with Gaboxadol Improves Sleep Maintenance and Enhances Slow Wave Sleep in Adult Patients with Primary Insomnia," Psychopharmacology, vol. 195, (2007); pp. 139-146.
Mathias et al., "The GABAA Agonist Gaboxadol Improves the Quality of Post-Nap Sleep," Psychopharmacology, vol. 157 (2001); pp. 299-304.
Mathias et al., "Effect of Repeated Gaboxadol Administration on Night Sleep and Next-Day Performance in Healthy Elderly Subjects," Neuropsychopharmacology, vol. 30, (2005) pp. 833-841.
Olmos-Serrano et al., "The GABAA Receptor Agonist THIP Ameliorates Specific Behavioral Deficits in the Mouse Model of Fragile X Syndrome," Developmental Neuroscience, vol. 33, Fragile X Syndrome/Review, (2011), pp. 395-403.
Videnovic et al., "Circadian Melatoni Rhythm and Excessive Daytime Sleepiness in Parkinson Disease Free," JAMA Neurol. 71(4), 2014; Original Investigation—Apr. 2014; pp. 463-469 (12 pages).
Vardya et al., "Positive Modulation of δ-Subunit Containing GABAA Receptors in Mouse neurons" Neuropharmacology, vol. 63; 2012; pp. 469-479.
International Search Report and Written Opinion of the International Searching Authority, dated Sep. 27, 2016, corresponding to International Application No. PCT/US16/42238; 8 total pages.
Egawa et al., "Pathophysiological power of improper tonic GABA(A) conductances in mature and immature models." Frontiers in Neural Circuits, Oct. 2013, vol. 7, Article 170; pp. 1-15.
PCT Notice concerning Transmittal of International Preliminary Report on Patentability (Chapter I of the Patent Cooperation Treaty), International Preliminary Report on Patentability and Written Opinion of the International Searching Authority, dated Feb. 1, 2018, corresponding to International Application No. PCT/US2016/042238; 8 total pages.
Reagan-Shaw et al., "Dose translation from animal to human studies revisited", FASEB J, vol. 22, No. 3, Oct. 17, 2007; pp. 659-661.
International Search Report and Written Opinion of the International Searching Authority, dated Aug. 14, 2015, corresponding to International Application No. PCT/US2015/029155; 19 total pages.

(56) References Cited

OTHER PUBLICATIONS

Boast et al., "5HT Antagonists Attenuate MK801-Impaired Radial Arm Maze Performance in Rats," Neurobiology of Learning and Memory, vol. 71, No. 3, May 1, 1999; pp. 259-271.
C. Idzikowski et al., "5-Hydroxytryptamine-2 Antagonist Increases Human Slow Wave Sleep," Brain Research, vol. 378, No. 1, Jul. 16, 1986, Elsevier; pp. 164-168.
Nagar et al., "Orally disintegrating tablets: formulation, preparation techniques and evaluation", Journal of Applied Phramaceutical Science, vol. 01, No. 04, 2011; pp. 35-45.
Gupta Nitan Bharti et al., "Pulsatile Drug Delivery as Modified Release Dosage Form: A Review", Journal of Drug Delivery & Therapeutics, vol. 2, No. 6, 2012; pp. 102-110.
Reddy et al., "Review on: Pulsatile Drug Delivery Systems", Journal of Pharmaceutical Sciences and Research, (ISSN: 0975-1459), vol. 1, No. 4, 2009; pp. 109-115.
The United States Pharmacopeia (USP) disintegration test method set forth at section 701 Disintegration, Revision Bulletin Official Aug. 1, 2008; pp. 1-3.
Bharawaj et al., "Orally Disintegrating Tablets: A Review", Drug Invention Today, vol. 2, No. 1, (ISSN: 0975-7619), 2010; pp. 81-88.
Boyle et al., "Tolerability, pharmacokinetics and night-time effects on postural sway and critical flicker fusion of gaboxadol and zolpidem in elderly subjects," British Journal of Clinical Pharmacology, 2008, vol. 67, No. 2; pp. 180-190.
Guidance for Industry, Orally Disintegrating Tablets, United States Department of Health and Human Services, Food and Drug Administraction, Center for Drug Evaluation and Research (CDER), Dec. 2008, Chemistry, pp. 1-8.
Yapar et al., "Orally Disintegrating Tablets: An Overview," Journal of Applied Pharmaceutical Science, Feb. 2014, vol. 4, No. 02, pp. 118-125.
Fu et al., "Drug Release Kinetics and Transport Mechanisms of Non-degradable and Degradable Polymeric Delivery Systems," NIH Public Access, Author Manuscript, National Institute of Health, Expert Opin Drug Deliv., Apr. 2010; vol. 7, No. 4 (pp. 429-444) 28 pages.
Kesisoglou et al., "Utility of PBPK Absorption Modeling to Guide Modified Release Formulation Development of Gaboxadol, a Highly Soluble Compound with Region-Dependent Absorption," Research Article—Pharmaceutics, Drug Delivery and Pharmaceutical Technology, Aug. 19, 2015; Journal of Pharmacetuical Sciences, vol. 105 (2016); pp. 722-728 (7 pages).
Boyle et al., "Next-day residual effects of gaboxadol and flurazepam administered at bedtime: a randomized double-blind study in healthy elderly subjects," Human Psychopharmacology, 2009, vol. 24, pp. 61-71.
Notification Conerning Transmittal of International Preliminary Report on Patentability, International Preliminary Report on Patentability and Written Opinion of the International Searching Authority, dated Feb. 13, 2020, corresponding to counterpart International Application No. PCT/US2018/044973; 12 total pages.

* cited by examiner

USE OF GABOXADOL IN THE TREATMENT OF DIABETES AND RELATED CONDITIONS

CROSS REFERENCE TO RELATED APPLICATIONS

This application claims benefit of and priority to U.S. Provisional Application No. 62/541,260, filed Aug. 4, 2017, which is incorporated herein by reference in its entirety.

BACKGROUND

1. Technical Field

Treatment of metabolic diseases such as diabetes and pre-diabetes with gaboxadol is provided.

2. Description of Related Art

According to the World Health Organization, diabetes is a chronic disease that occurs either when the pancreas does not produce enough insulin or when the body cannot effectively use the insulin it produces. Insulin regulates (decreases) the concentration of blood sugar (glucose). It is a peptide hormone produced by beta cells of the pancreatic islets. Insulin regulates the metabolism of carbohydrates, fats and protein by promoting the absorption of glucose from the blood into fat, liver and skeletal muscle cells. Pancreatic beta cells (β cells) are sensitive to glucose concentrations in the blood. In non-diabetics, when glucose concentrations in the blood are high, the pancreatic beta cells secrete insulin into the blood; when glucose levels are low, secretion of insulin is inhibited. Pancreatic alpha cells secrete glucagon, another peptide hormone, into the blood to raise the concentration of glucose in the blood in the opposite manner, i.e., increased secretion when blood glucose is low, and decreased secretion when glucose concentrations are high. The secretion of insulin and glucagon into the blood in response to the blood glucose concentration is the primary mechanism responsible for keeping the glucose levels in the extracellular fluids within narrow limits Hyperglycemia, or high blood sugar, is a common effect of uncontrolled diabetes and over time can lead to serious damage to many of the body's systems, especially the nerves and blood vessels. According to the World Health Organization the number of people with diabetes has risen from 108 million in 1980 to 422 million in 2014. In 2014, 8.5% of adults aged 18 years and older had diabetes. In 2012 diabetes was the direct cause of 1.5 million deaths and high blood glucose was the cause of another 2.2 million deaths. Diabetes is a major cause of blindness, kidney failure, heart attacks, stroke and lower limb amputation. Adults with diabetes have a 2-3-fold increased risk of heart attacks and strokes. Combined with reduced blood flow, neuropathy (nerve damage) in the feet increases the chance of foot ulcers, infection and eventual need for limb amputation. Diabetes is among the leading causes of kidney failure.

Type 1 diabetes (previously known as insulin-dependent, juvenile or childhood-onset) is characterized by deficient insulin production and typically requires daily administration of insulin. The majority of cases of Type 1 diabetes are primarily due to pancreatic islet beta-cell destruction. Type 1 diabetics are prone to ketoacidosis. Symptoms of type 1 diabetes include excessive excretion of urine (polyuria), thirst (polydipsia), constant hunger, weight loss, vision changes and fatigue. These symptoms may occur suddenly. Type 2 diabetes (formerly called non-insulin-dependent or adult-onset) results from the body's ineffective use of insulin. The majority of people with diabetes around the world have type 2 diabetes. Type 2 diabetes has been correlated to excess body weight and physical inactivity. Symptoms may be similar to those of Type 1 diabetes, but are often less marked. Sleep apnea has been correlated to an increased risk of developing Type 2 diabetes. See, Botros et al., *Amer. J. Med.*, 122(12), 1122-1127 (2009). Over 50% of Type 2 diabetics have sleep apnea. Until recently, Type 2 diabetes was seen only in adults but it is now also occurring increasingly frequently in children.

Impaired glucose tolerance (IGT) and impaired fasting glycemia (IFG) (collectively referred to as "pre-diabetes" herein) are intermediate conditions in the transition between normality and diabetes. IFG and IGT are not interchangeable and represent different abnormalities of glucose regulation, one in the fasting state and one post-prandial. People with IGT or IFG are at high risk of progressing to type 2 diabetes, although it is not inevitable.

According to the guidelines of the American Diabetes Association criteria for diabetes diagnosis involves four options: a fasting plasma glucose level greater than or equal to 126 mg/dl, a 2-hour oral glucose tolerance test (OGTT) providing a plasma glucose value of greater than or equal to 200 mg/dl, an HbA1c value greater than or equal to 6.5%, or a random plasma glucose level greater than or equal to 200 mg/dl in individuals with symptoms of hyperglycemia or hyperglycemic crisis. Pre-diabetes is defined as having a fasting glucose level of between 100 mg/dl and 125 mg/dl, a 2-hour OGTT plasma glucose level of between 140 mg/dl and 199 mg/dl, or an HbA1c value between 5.7 and 6.4%. Pre-diabetes may be considered to be a major risk factor for the development of type 2 diabetes mellitus, cardiovascular disease and mortality.

In the monitoring of the treatment of diabetes, the HbA1c value, which is the product of a non-enzymatic glycation of the hemoglobin B chain, may be considered to be an important parameter. HbA1c values depend on the blood sugar level and the life time of erythrocytes in the blood. HbA1c values typically reflect the average blood sugar level 4-12 weeks prior to removal and testing of a patient's blood. Diabetic patients whose HbA1c level has been well controlled over a long time treatment (i.e. <6.5% of the total hemoglobin in the sample) are typically better protected from diabetic microangiopathy. The available treatments for diabetes can give the diabetic an average improvement in their HbA1c level of the order of 1.0-1.5%. However, this reduction in the HbA1C level may not be sufficient in all diabetics to bring them into the desired target range of <7.0%, preferably <6.5% and more preferably <6% HbA1c.

Within glycemic control, in addition to improvement of the HbA1c level, other recommended therapeutic goals for type 2 diabetes patients are improvement of fasting plasma glucose (FPG) and of postprandial plasma glucose (PPG) levels to normal or as near normal as possible. Desired target ranges of preprandial (fasting) plasma glucose can be, e.g., 90-130 mg/dL or <110 mg/dL, and of two-hour postprandial plasma glucose can be, e.g., <180 mg/dL or <140 mg/dL.

Diet therapy and exercise therapy are frequently considered to be essential in the treatment of diabetes. When these therapies do not sufficiently control the condition of patients (especially their blood sugar levels), an oral or non-oral antidiabetic agent can be used for the treatment of diabetes. Conventional antidiabetic or hypoglycemic agents include, without limitation, biguanides, dipeptidyl peptidase-4 (DPP-4) inhibitors, sulphonylureas, thiazolidinediones, meglitinides (aka glinides), alpha-glucosidase blockers, GLP-1 and GLP-1 analogs, as well as insulin and insulin analogs.

Biguanides such as metformin, buformin and phenformin may be used as hypoglycemic agents in the treatment of diabetes. Metformin decreases hepatic glucose production, decreases intestinal absorption of glucose, and improves insulin sensitivity by increasing peripheral glucose uptake and utilization. The mechanistic aspects of metformin action are unclear. See, Pernicova and Korbonits, *Nature Reviews Endocrinol.*, 2014; 10:143-156. Metformin has also been used in the treatment of polycystic ovary syndrome (PCOS) and anovulatory infertility in women with PCOS. See, e.g., Johnson, *Ann. Transl. Med.*, 2014, 2(6):56.

Inhibitors of dipeptidyl peptidase 4, also known as DPP-4 inhibitors or gliptins, are a class of oral hypoglycemics that inhibit the enzymatic activity of DPP-4, thereby prolonging incretin effect in vivo. Incretin is a hormone that stimulates insulin secretion in response to meals. Glucagon-like peptide 1 receptor agonists, also known as GLP-1 receptor agonists or incretin mimetics are a class of parenterally administered hypoglycemics that are agonists of the GLP-1 receptor (GLP1R). GLP1R is known to be expressed in pancreatic beta cells. Activated GLP1R stimulates the adenylyl cyclase pathway which results in increased insulin synthesis and release of insulin. Sulfonylureas are a class of oral hypoglycemics that act by increasing insulin release from the beta cells in the pancreas. Sulfonylureas bind to an ATP-dependent K$^+$ (K$_{ATP}$) channel on the cell membrane of pancreatic beta cells. This increases the concentration of intracellular potassium, which causes the electric potential over the membrane to become more positive. This depolarization opens voltage-gated Ca$^{2+}$ channels. The rise in intracellular calcium leads to increased fusion of insulin granulae with the cell membrane, and therefore increased secretion of (pro)insulin. Thiazolidinediones or TZDs are a class of oral hypoglycemics that act by activating PPARs (peroxisome proliferator-activated receptors), a group of nuclear receptors. When activated, the receptor binds to DNA in complex with the retinoid X receptor (RXR), another nuclear receptor, increasing transcription of a number of certain genes and decreasing transcription of others. The main effect of expression and repression of specific genes is an increase in the storage of fatty acids in adipocytes, thereby decreasing the amount of fatty acids present in circulation. As a result, cells become more dependent on the oxidation of carbohydrates, more specifically glucose, in order to yield energy for other cellular processes. Meglitinides (also known as glinides) are a class of oral hypoglycemics that bind to an ATP-dependent K$^+$ (K$_{ATP}$) channel on the cell membrane of pancreatic beta cells in a similar manner to sulfonylureas but have a weaker binding affinity and faster dissociation from the SUR1 binding site. This increases the concentration of intracellular potassium, which causes the electric potential over the membrane to become more positive. This depolarization opens voltage-gated Ca$^{2+}$ channels. The rise in intracellular calcium leads to increased fusion of insulin granulae with the cell membrane, and therefore increased secretion of (pro)insulin. Alpha-glucosidase inhibitors are a class of oral hypoglycemics that cause competitive and reversible inhibition of intestinal alpha-glucosidases thereby delaying carbohydrate digestion, prolonging the overall carbohydrate digestion time, thus reducing the rate of glucose absorption.

Gaboxadol (4,5,6,7-tetrahydroisoxazolo [5,4-c] pyridine-3-ol) (THIP)) is described in U.S. Pat. Nos. 4,278,676, 4,362,731, 4,353,910, and WO 2005/094820 is a selective GABA$_A$ receptor agonist with a preference for δ-subunit containing GABA$_A$ receptors. In the early 1980s gaboxadol was the subject of a series of pilot studies that tested its efficacy as an analgesic and anxiolytic, as well as a treatment for tardive dyskinesia, Huntington's disease, Alzheimer's disease, and spasticity. In the 1990s gaboxadol moved into late stage development for the treatment of insomnia but failed to show significant effects in sleep onset and sleep maintenance in a three-month efficacy study. Additionally, patients with a history of drug abuse who received gaboxadol experienced a steep increase in psychiatric adverse events. As a result of these negative results the development of gaboxadol was terminated. A study involving gaboxadol was conducted to evaluate its effect on fasting and overload blood glucose in streptozotocin-induced diabetic rats with moderate to severe hyperglycemia. See, Gomez et al., *Jpn. J. Pharmacol.*, 80, 327-331 (1999). The hypoglycemic effect of gaboxadol was very mild and could only be seen in the moderately hyperglycemic rats. Id.

Although intensive treatment of hyperglycemia can reduce the incidence of chronic damage, many patients with diabetes remain inadequately treated, partly because of limitations in long term efficacy, tolerability and dosing inconvenience of existing antihyperglycemic therapies. The use of conventional hypoglycemic agents can be associated with various adverse effects. For example, metformin can be associated with lactic acidosis or gastrointestinal side effects; sulfonylureas, meglitinides (glinides) and insulin or insulin analogues can be associated with hypoglycemia or weight gain; thiazolidinediones can be associated with edema, bone fracture, weight gain or heart failure/cardiac effects; and alpha-glucosidase blockers and GLP-1 or GLP-1 analogues can be associated with gastrointestinal adverse effects (e.g. dyspepsia, flatulence or diarrhea, or nausea or vomiting). There exists a continuing need for improved antihyperglycemic therapy in the treatment of metabolic diseases.

SUMMARY

Methods of treating a metabolic disease described herein include administering gaboxadol or a pharmaceutically acceptable salt thereof to a patient in need thereof to lower one or more of HbA1c level, fasting plasma glucose level, 2-hour oral glucose tolerance test (OGTT) result level, and random plasma glucose level. In embodiments, the metabolic disease is diabetes. In embodiments the diabetes is type 2 diabetes. In embodiments the diabetes is type 1 diabetes. In embodiments, the metabolic disease is pre-diabetes. In embodiments, the HbA1c level is lowered by an amount greater than 0.25%. In embodiments, the HbA1c level is lowered by an amount greater than 0.5%. In embodiments, the HbA1c level is lowered by an amount greater than 0.75%. In embodiments, the HbA1c level is lowered by an amount greater than 1.0%. In embodiments, the HbA1c level is lowered by an amount greater than 1.5%. In embodiments, gaboxadol or a pharmaceutically acceptable salt thereof is administered in combination with one or more hypoglycemic agents such as a biguanide, a dipeptidyl peptidase-4 (DPP-4) inhibitor, a sulphonylurea, a thiazolidinedione, a meglitinide (glinide), an alpha-glucosidase blocker, an glucagon-like peptide-1 receptor agonist, insulin and an insulin analog. In embodiments, the combination of gaboxadol or a pharmaceutically acceptable salt thereof and the one or more hypoglycemic agents provides a therapeutic benefit greater than the additive effect of administering the same dosage of each of gaboxadol or a pharmaceutically acceptable salt thereof and the hypoglycemic agents alone.

Methods of treating a metabolic disease are provided which include administering gaboxadol or a pharmaceutically acceptable salt thereof to a patient diagnosed with the metabolic disease and sleep apnea in an amount effective to reduce episodes of sleep apnea. In embodiments, the metabolic disease is diabetes. In embodiments the diabetes is type 2 diabetes. In embodiments the diabetes is type 1 diabetes. In embodiments, the metabolic disease is pre-diabetes. In embodiments, the administering is effective to lower one or more of HbA1c level, fasting plasma glucose level, 2-hour oral glucose tolerance test (OGTT) result level, and random plasma glucose level in the patient. In embodiments, the HbA1c level is lowered by an amount greater than 0.5%. In embodiments, the HbA1c level is lowered by an amount greater than 0.75%. In embodiments, the HbA1c level is lowered by an amount greater than 1.0%. In embodiments, the HbA1c level is lowered by an amount greater than 1.5%. In embodiments, gaboxadol or a pharmaceutically acceptable salt thereof is administered in combination with one or more hypoglycemic agents such as a biguanide, a dipeptidyl peptidase-4 (DPP-4) inhibitor, a sulphonylurea, a thiazolidinedione, a meglitinide (glinide), an alpha-glucosidase blocker, an glucagon-like peptide-1 receptor agonist, insulin and an insulin analog. In embodiments, the combination of gaboxadol or a pharmaceutically acceptable salt thereof and the one or more hypoglycemic agents provides a therapeutic benefit greater than the additive effect of administering the same dosage of gaboxadol or a pharmaceutically acceptable salt thereof alone.

DETAILED DESCRIPTION

Provided herein are methods and compositions for use in treating metabolic disorders such as diabetes, including type 1 diabetes, type 2 diabetes and pre-diabetes. In embodiments, administration of gaboxadol or a pharmaceutically acceptable salt thereof, alone or optionally in combination with one or more hypoglycemic agents such as a biguanide, a dipeptidyl peptidase-4 (DPP-4) inhibitor, a sulphonylurea, a thiazolidinedione, a meglitinide (glinide), an alpha-glucosidase blocker, an glucagon-like peptide-1 receptor agonist, insulin or an insulin analog can reduce symptoms of, prevent, slow the progression of, or delay a metabolic disorder such as, e.g., type 1 diabetes, type 2 diabetes, pre-diabetes, impaired glucose tolerance (IGT), impaired fasting blood glucose (IFG), hyperglycemia, and postprandial hyperglycemia.

Methods and compositions for use in treating metabolic disorders disclosed herein are used for improving glycemic control. "Improvement of glycemic control", "improving glycemic control" or "glycemic control" refers to improvement of glucose tolerance, improvement of postprandial plasma glucose concentration, improvement of fasting plasma glucose concentration, improvement of the HbA1c value or/and improvement of fasting plasma insulin concentration.

Methods and compositions for use in treating metabolic disorders disclosed herein improve, reduce or alleviate symptoms or conditions associated with metabolic diseases. Conditions associated with metabolic disorders can include, e.g., sleep apnea, obesity, dyslipidemia, hyperlipidemia, hypercholesterolemia, hypertension, atherosclerosis, endothelial dysfunction, osteoporosis, chronic systemic inflammation, non-alcoholic fatty liver disease (NAFLD), retinopathy, neuropathy, nephropathy and/or metabolic syndrome. Methods and compositions for use in treating metabolic disorders disclosed herein can improve glycemic control, e.g., reduce fasting plasma glucose, reduce postprandial plasma glucose and/or reduce HbA1c. Methods and compositions for use in treating metabolic disorders disclosed herein can prevent, slow, delay or reverse progression from impaired glucose tolerance (IGT), impaired fasting blood glucose (IFG), insulin resistance from metabolic syndrome, to type 2 diabetes.

Methods and compositions for use in treating metabolic disorders disclosed herein can prevent, reduce the risk, slow the progression, delay or treat complications of diabetes such as micro- and macrovascular diseases including nephropathy, micro- or macroalbuminuria, proteinuria, retinopathy, cataracts, neuropathy, learning or memory impairment, neurodegenerative or cognitive disorders, cardio- or cerebrovascular diseases, tissue ischemia, diabetic foot ulcers, atherosclerosis, hypertension, endothelial dysfunction, myocardial infarction, acute coronary syndrome, unstable angina pectoris, stable angina pectoris, peripheral arterial occlusive disease, cardiomyopathy, heart failure, heart rhythm disorders, vascular restenosis, and/or stroke. Methods and compositions for use in treating metabolic disorders disclosed herein can prevent, slow the progression of, delay or treat type 2 diabetes with primary or secondary failure to conventional (oral) hypoglycemic mono- or combination therapy. Methods and compositions for use in treating metabolic disorders disclosed herein can achieve a reduction in the dose of conventional hypoglycemic medication required for adequate therapeutic effect, thereby reducing the risk for adverse effects associated with conventional hypoglycemic medication. Methods and compositions for use in treating metabolic disorders disclosed herein can maintain and/or improve insulin sensitivity and/or treat or prevent hyperinsulinemia and/or insulin resistance.

In embodiments, methods and compositions for use in treating metabolic disorders disclosed herein are used to treat inadequate or insufficient glycemic control in a patient with a metabolic disorder. Inadequate or insufficient glycemic control may be considered to be a condition wherein patients exhibit HbA1c values above 6.0%, e.g., above 6.5%, above 7.0%, above 7.5%, above 8%, above 8.5%, above 9%, above 9.5%, above 10%, above 10.5%, above 11%, or any value between 6.0% and 11.0%. For example, patients with inadequate or insufficient glycemic control may include patients having a HbA1c value from 6.5 to 7.0%, 7.0-7.5%, 7.5 to 10% or from 7.5 to 11%. For example, inadequately controlled patients can refer to patients with poor glycemic control including, without being limited, patients having a HbA1c value≥9%.

In embodiments, methods and compositions for use in treating metabolic disorders disclosed herein lower HbA1c levels by an amount greater than 0.25%. In embodiments, methods and compositions for use in treating metabolic disorders disclosed herein lower HbA1c levels by an amount greater than 0.5%. In embodiments, methods and compositions for use in treating metabolic disorders disclosed herein lower HbA1c levels by an amount greater than 0.75%. In embodiments, methods and compositions for use in treating metabolic disorders disclosed herein lower HbA1c levels by an amount greater than 1.0%. In embodiments, methods and compositions for use in treating metabolic disorders disclosed herein lower HbA1c levels by an amount greater than 1.25%. In embodiments, methods and compositions for use in treating metabolic disorders disclosed herein lower HbA1c levels by an amount greater than 1.5%.

Many pharmaceutical products are administered as a fixed dose, at regular intervals, to achieve therapeutic efficacy. The product's duration of action is typically reflected by its plasma half-life. Gaboxadol is a selective GABA$_A$ receptor agonist with a relatively short half-life (t½=1.5 h). Since efficacy is often dependent on sufficient exposure within the central nervous system administration of CNS drugs with a short half-life may require frequent maintenance dosing. Advantageously disclosed herein are methods of treating metabolic disorders such as diabetes or pre-diabetes by administration of gaboxadol or a pharmaceutically acceptable salt thereof. For example, in embodiments, methods of treating a treating metabolic disorder are provided which include administering to a patient in need thereof a pharmaceutical composition including about 0.05 mg to about 50 mg, e.g., 0.05 mg to about 30 mg, gaboxadol or a pharmaceutically acceptable salt thereof wherein the composition provides improvement in glycemic control for more than 6 hours after administration to the patient.

Embodiments described herein provide that a patient in need thereof is administered a pharmaceutical composition including gaboxadol or a pharmaceutically acceptable salt thereof. Gaboxadol or pharmaceutically acceptable salt thereof may be provided as an acid addition salt, a zwitter ion hydrate, zwitter ion anhydrate, hydrochloride or hydrobromide salt, or in the form of the zwitter ion monohydrate. Acid addition salts, include but are not limited to, maleic, fumaric, benzoic, ascorbic, succinic, oxalic, bis-methylene-salicylic, methanesulfonic, ethane-disulfonic, acetic, propionic, tartaric, salicylic, citric, gluconic, lactic, malic, mandelic, cinnamic, citraconic, aspartic, stearic, palmitic, itaconic, glycolic, p-amino-benzoic, glutamic, benzene sulfonic or theophylline acetic acid addition salts, as well as the 8-halotheophyllines, for example 8-bromo-theophylline. In other suitable embodiments, inorganic acid addition salts, including but not limited to, hydrochloric, hydrobromic, sulfuric, sulfamic, phosphoric or nitric acid addition salts may be used.

In embodiments, gaboxadol is provided as gaboxadol monohydrate. One skilled in the art will readily understand that the amounts of active ingredient in a pharmaceutical composition will depend on the form of gaboxadol provided. For example, pharmaceutical compositions of including 5.0, 10.0, or 15.0 mg gaboxadol correspond to 5.6, 11.3, or 16.9 mg gaboxadol monohydrate.

In embodiments, gaboxadol is crystalline, such as the crystalline hydrochloric acid salt, the crystalline hydrobromic acid salt, or the crystalline zwitter ion monohydrate. In embodiments, gaboxadol is provided as a crystalline monohydrate.

Deuteration of pharmaceuticals to improve pharmacokinetics (PK), pharmacodynamics (PD), and toxicity profiles, has been demonstrated previously with some classes of drugs. Accordingly the use of deuterium enriched gaboxadol is contemplated and within the scope of the methods and compositions described herein. Deuterium can be incorporated in any position in replace of hydrogen synthetically, according to the synthetic procedures known in the art. For example, deuterium may be incorporated to various positions having an exchangeable proton, such as the amine N—H, via proton-deuterium equilibrium exchange. Thus, deuterium may be incorporated selectively or non-selectively through methods known in the art to provide deuterium enriched gaboxadol. See Journal of Labeled Compounds and Radiopharmaceuticals 19(5) 689-702 (1982).

Deuterium enriched gaboxadol may be described by the percentage of incorporation of deuterium at a given position in the molecule in the place of hydrogen. For example, deuterium enrichment of 1% at a given position means that 1% of molecules in a given sample contain deuterium at that specified position. The deuterium enrichment can be determined using conventional analytical methods, such as mass spectrometry and nuclear magnetic resonance spectroscopy. In embodiments deuterium enriched gaboxadol means that the specified position is enriched with deuterium above the naturally occurring distribution (i.e., above about 0.0156%). In embodiments deuterium enrichment is no less than about 1%, no less than about 5%, no less than about 10%, no less than about 20%, no less than about 50%, no less than about 70%, no less than about 80%, no less than about 90%, or no less than about 98% of deuterium at a specified position.

In embodiments, methods of treating a metabolic disorder such as type 1 diabetes, type 2 diabetes or pre-diabetes include administering to a patient in need thereof a pharmaceutical composition including about 0.05 mg to about 50 mg gaboxadol or a pharmaceutically acceptable salt thereof. In embodiments, methods of treating a metabolic disorder such as type 1 diabetes, type 2 diabetes or pre-diabetes include administering to a patient in need thereof a pharmaceutical composition including about 0.1 mg to about 30 mg gaboxadol or a pharmaceutically acceptable salt thereof. In embodiments, methods of treating a metabolic disorder such as type 1 diabetes, type 2 diabetes or pre-diabetes include administering to a patient in need thereof a pharmaceutical composition including about 1.0 mg to about 20 mg gaboxadol or a pharmaceutically acceptable salt thereof.

In embodiments, the pharmaceutical compositions can include 0.1 mg to 30 mg, 0.1 mg to 25 mg, 0.1 mg to 20 mg, 0.1 mg to 15 mg, 0.5 mg to 25 mg, 0.5 mg to 20 mg, 0.5 to 15 mg, 1 mg to 25 mg, 1 mg to 20 mg, 1 mg to 15 mg, 1.5 mg to 25 mg, 1.5 mg to 20 mg, 1.5 mg to 15 mg, 2 mg to 25 mg, 2 mg to 20 mg, 2 mg to 15 mg, 2.5 mg to 25 mg, 2.5 mg to 20 mg, 2.5 mg to 15 mg, 3 mg to 25 mg, 3 mg to 20 mg, 3 mg to 15 mg gaboxadol or a pharmaceutically acceptable salt thereof.

In embodiments, the pharmaceutical compositions can include 5 mg to 20 mg, 5 mg to 10 mg, 4 mg to 6 mg, 6 mg to 8 mg, 8 mg to 10 mg, 10 mg to 12 mg, 12 mg to 14 mg, 14 mg to 16 mg, 16 mg to 18 mg, or 18 mg to 20 mg gaboxadol or a pharmaceutically acceptable salt thereof.

In embodiments, the pharmaceutical compositions can include 0.1 mg, 0.25 mg, 0.5 mg, 1 mg, 2.5 mg, 3 mg, 4 mg, 5 mg, 7 mg, 7.5 mg, 10 mg, 12.5 mg, 15 mg, 17.5 mg, 20 mg gaboxadol or a pharmaceutically acceptable salt thereof or amounts that are multiples of such doses. In embodiments, the pharmaceutical compositions include 2.5 mg, 5 mg, 7.5 mg, 10 mg, 15 mg, or 20 mg gaboxadol or a pharmaceutically acceptable salt thereof.

Pharmaceutical compositions herein may be provided with conventional release profiles or modified release profiles. Conventional (or unmodified) release oral dosage forms such as tablets or capsules typically release medications into the stomach or intestines as the tablet or capsule shell dissolves. The pattern of drug release from modified release (MR) dosage forms is deliberately changed from that of a conventional dosage form to achieve a desired therapeutic objective and/or better patient compliance. Types of MR drug products include orally disintegrating dosage forms (ODDFs) which provide immediate release, extended release dosage forms, delayed release dosage forms (e.g., enteric coated), and pulsatile release dosage forms. In embodiments, pharmaceutical compositions with different drug release profiles may be combined to create a two phase or three-phase release profile. For example, pharmaceutical compositions may be provided with an immediate release and an extended release profile. In embodiments, pharmaceutical compositions may be provided with an extended release and delayed release profile. Such composition may be provided as pulsatile formulations, multilayer tablets, or capsules containing tablets, beads, granules, etc. Compositions may be prepared using a pharmaceutically acceptable "carrier" composed of materials that are considered safe and effective. The "carrier" includes all components present in the pharmaceutical formulation other than the active ingredient or ingredients. The term "carrier" includes, but is not limited to, diluents, binders, lubricants, disintegrants, fillers, and coating compositions.

An ODDF is a solid dosage form containing a medicinal substance or active ingredient which disintegrates rapidly, usually within a matter of seconds when placed upon the tongue. The disintegration time for ODDFs generally range from one or two seconds to about a minute. ODDFs are designed to disintegrate or dissolve rapidly on contact with saliva. This mode of administration can be beneficial to people who may have problems swallowing tablets whether it be from physical infirmity or psychiatric in nature. In embodiments, when administered to an oral cavity, an ODDF herein disintegrates in less than one minute, less than 55 seconds, less than 50 seconds, less than 45 seconds, less than 40 seconds, less than 35 seconds, less than 30 seconds, less than 25 seconds, less than 20 seconds, less than 15 seconds, less than 10 seconds, or less than 5 seconds.

An orally disintegrating tablet (ODT) is a solid dosage form containing a medicinal substance or active ingredient which disintegrates rapidly, usually within a matter of seconds when placed upon the tongue. The disintegration time for ODTs generally ranges from several seconds to about a minute. ODTs are designed to disintegrate or dissolve rapidly on contact with saliva, thus eliminating the need to chew the tablet, swallow the intact tablet, or take the tablet with liquids. In embodiments, an ODT herein disintegrates in less than one minute, less than 55 seconds, less than 50 seconds, less than 45 seconds, less than 40 seconds, less than 35 seconds, less than 30 seconds, less than 25 seconds, less than 20 seconds, less than 15 seconds, less than 10 seconds, or less than 5 seconds, based upon, e.g., the United States Pharmacopeia (USP) disintegration test method set forth at section 701, Revision Bulletin Official Aug. 1, 2008.

In embodiments, the fast dissolving property of the ODTs requires quick ingress of water into the tablet matrix. This may be accomplished by maximizing the porous structure of the tablet, incorporation of suitable disintegrating agents and use of highly water-soluble excipients in the formulation. Excipients used in ODTs typically contain at least one superdisintegrant (which can have a mechanism of wicking, swelling or both), a diluent, a lubricant and optionally a swelling agent, sweeteners and flavorings. See, e.g., Nagar et al., *Journal of Applied Pharmaceutical Science* 2011; 01(04):35-45, incorporated herein by reference. Superdisintegrants can be classified as synthetic, natural and co-processed. In this context synthetic superdisintegrants can be exemplified by sodium starch glycolate, croscarmellose sodium, cross-linked polyvinylpyrrolidone, low-substituted hydroxypropyl cellulose, microcrystalline cellulose, partially pregelatinized starch, cross-linked alginic acid and modified resin. Diluents can include, e.g., mannitol, sorbitol, xylitol, calcium carbonate, magnesium carbonate, calcium sulfate, magnesium trisilicate and the like. Lubricants can include, e.g., magnesium stearate and the like. Those skilled in the art are familiar with ODT manufacturing techniques.

Other ODDFs which may be used herein include rapidly dissolving films which are thin oral strips that release medication such as gaboxadol or a pharmaceutically acceptable salt thereof quickly after administration to the oral cavity. The film is placed on a patient's tongue or any other mucosal surface and is instantly wet by saliva whereupon the film rapidly hydrates and dissolves to release the medication. See. e.g., Chaturvedi et al., *Curr Drug Deliv.* 2011 July; 8(4):373-80. Fastcaps are a rapidly disintegrating drug delivery system based on gelatin capsules. Freeze dried (lyophilized) wafers are rapidly disintegrating, thin matrixes that contain a medicinal agent. The wafer or film disintegrates rapidly in the oral cavity and releases drug which dissolves or disperses in the saliva. See, e.g., Boateng et al., *Int J Pharm.* 2010 Apr. 15; 389(1-2):24-31. Those skilled in the art are familiar with various techniques utilized to manufacture ODDFs such as freeze drying, spray drying, phase transition processing, melt granulation, sublimation, mass extrusion, cotton candy processing, direct compression, etc.

When administered, ODDFs containing gaboxadol or a pharmaceutically acceptable salt thereof, either alone or with one or more additional drugs discussed herein (collective referred to herein as "drug", "drugs", "active agent", or "active agents"), disintegrate rapidly to release the drug(s), which dissolves or disperses in the saliva. The drug may be absorbed in the oral cavity, e.g., sublingually, buccally, from the pharynx and esophagus or from other sections of gastrointestinal tract as the saliva travels down. In such cases, bioavailability can be significantly greater than that observed from conventional tablet dosage forms which travel to the stomach or intestines where drug can be released.

In embodiments, pharmaceutical compositions having modified release profiles provide pharmacokinetic properties which result in both rapid onset and sustained duration of action. Such pharmaceutical compositions include an immediate release aspect and an extended release aspect. Immediate release aspects are discussed above in connection with ODDFs. Extended release dosage forms (ERDFs) have extended release profiles and are those that allow a reduction in dosing frequency as compared to that presented by a conventional dosage form, e.g., a solution or unmodified release dosage form. ERDFs provide a sustained duration of action of a drug. In embodiments, modified release dosage forms herein are ERDFs that do not have an ODDF aspect. In embodiments, modified release dosage forms herein incorporate an ODDF aspect to provide immediate release of a loading dose and then an ERDF aspect that provides prolonged delivery to maintain drug levels in the blood within a desired therapeutic range for a desirable period of time in excess of the activity resulting from a single dose of the drug. In embodiments, the ODDF aspect releases the drug immediately and the ERDF aspect thereafter provides continuous release of drug for sustained action.

In embodiments, an ODDF can be applied as a coating or band over an ERDF, or as a layer adjacent to an ERDF, to allow direct exposure of the ODDF to the oral cavity and consequent disintegration of the ODDF. In embodiments, the ODDF and the ERDF can be mixed in a chewable resin, e.g., gum. Those skilled in the art are familiar with techniques for applying coatings, bands and layers to fabricate pharmaceutical dosage forms.

Suitable formulations which provide extended release profiles are well-known in the art. For example, coated slow release beads or granules ("beads" and "granules" are used interchangeably herein) in which, e.g., gaboxadol or a pharmaceutically acceptable salt thereof, alone or in combination with one or more drugs, is applied to beads, e.g., confectioners nonpareil beads, and then coated with conventional release retarding materials such as waxes, enteric coatings and the like. In embodiments, some beads incorporate one drug while other beads incorporate a different drug. In embodiments, beads can be formed in which one or more drugs are mixed with a material to provide a mass from which the drug leaches out. In embodiments, the beads may be engineered to provide different rates of release by varying characteristics of the coating or mass, e.g., thickness, porosity, using different materials, etc. Beads having different rates of release may be combined into a single dosage form to provide variable or continuous release. The beads can be contained in capsules or compressed into tablets. In embodiments, the ODDF is applied as a coating, a layer or a band to a capsule or tablet. In embodiments, slow release cores which are incorporated into tablets or capsules can also provide extended release profiles. For example, one or more drugs can be mixed in a substance or a mixture of substances non-absorbable from the gastrointestinal tract but capable of slow dissolution or loss of drug by leaching, and an outer drug containing ODDF layer which is applied to the core by, e.g., compression or spraying. In embodiments, extended release profiles may be provided by multiple layer tablets, each layer having different release properties. Multilayer tableting machines allow incorporation into one tablet of two or more separate layers which may be made to release one or more drugs at different rates. For example, one or more outer layers may be an ODDF, and each other layer an ERDF that exhibits different release rates. In embodiments, one or more drugs are incorporated into porous inert carriers that provide extended release profiles. In embodiments, the porous inert carriers incorporate channels or passages from which the drug diffuses into surrounding fluids. In embodiments, one or more drugs are incorporated into an ion-exchange resin to provide an extended release profile. Prolonged action results from a predetermined rate of release of the drug from the resin when the drug-resin complex contacts gastrointestinal fluids and the ionic constituents dissolved therein. In embodiments, membranes are utilized to control rate of release from drug containing reservoirs. In embodiments, liquid preparations may also be utilized to provide an extended release profile. For example, a liquid preparation consisting of solid particles dispersed throughout a liquid phase in which the particles are not soluble. The suspension is formulated to allow at least a reduction in dosing frequency as compared to that drug presented as a conventional dosage form (e.g., as a solution or a prompt drug-releasing, conventional solid dosage form). For example, a suspension of ion-exchange resin constituents or microbeads.

In embodiments, absorbable or non-absorbable polymers may be utilized to form ERDFs. Various ERDFs including those discussed above and others that can be utilizable herein are known to those with skill in the art. See, e.g., Fu and Kao, *Expert Opin Drug Deliv.* 2010 April; 7(4): 429-444.

In embodiments, modified dosage forms herein incorporate delayed release dosage forms having delayed release profiles. Delayed release dosage forms can include delayed release tablets or delayed release capsules. A delayed release tablet is a solid dosage form which releases a drug (or drugs) such as gaboxadol or a pharmaceutically acceptable salt thereof at a time other than promptly after administration. A delayed release capsule is a solid dosage form in which the drug is enclosed within either a hard or soft soluble container made from a suitable form of gelatin, and which releases a drug (or drugs) at a time other than promptly after administration. For example, with respect to tablets or capsules, enteric-coated articles are examples of delayed release dosage forms. In embodiments, a delayed release tablet is a solid dosage form containing a conglomerate of medicinal particles that releases a drug (or drugs) at a time other than promptly after administration. In embodiments, the conglomerate of medicinal particles are covered with a coating which delays release of the drug. In embodiments, a delayed release capsule is a solid dosage form containing a conglomerate of medicinal particles that releases a drug (or drugs) at a time other than promptly after administration. In embodiments, the conglomerate of medicinal particles are covered with a coating which delays release of the drug.

In embodiments, ODDFs with a delayed release formulation aspect are provided that are solid dosage forms containing medicinal substances which disintegrate rapidly, usually within a matter of seconds, when placed upon the tongue, but which also releases a drug (or drugs) at a time other than promptly after administration. Accordingly, in embodiments, modified release dosage forms herein incorporate an ODDF aspect to provide immediate release of a loading dose and then an a delayed release formulation aspect that provides a period in which there is no drug delivery followed by a period of drug delivery to provide drug levels in the blood within a desired therapeutic range for a desirable period of time in excess of the activity resulting from a single dose of the drug. In embodiments, the ODDF aspect releases drug immediately and then, after a period of delay, a delayed release formulation aspect thereafter provides a single release of drug to provide an additional period of activity. In embodiments, the ODDF aspect releases the drug immediately and then, after a period of delay, a delayed release formulation aspect thereafter provides a continuous release of drug for sustained action. In embodiments, different drugs are released together or at different times.

Delayed release dosage forms are known to those skilled in the art. For example, coated delayed release beads or granules ("beads" and "granules" are used interchangeably herein) in which, e.g., gaboxadol or a pharmaceutically acceptable salt thereof and/or other drug is applied to beads, e.g., confectioners nonpareil beads, and then coated with conventional release delaying materials such as waxes, enteric coatings and the like. In embodiments, beads can be formed in which drug is mixed with a material to provide a mass from which the drug leaches out. In embodiments, the beads may be engineered to provide different rates of release by varying characteristics of the coating or mass, e.g., thickness, porosity, using different materials, etc. In embodiments, enteric coated granules of drug can be contained in an enterically coated capsule or tablet which releases the granules in the small intestine. In embodiments, the granules have a coating which remains intact until the coated granules reach at least the ileum and thereafter provide a delayed release of the drug in the colon. Suitable enteric coating materials are well known in the art, e.g., Eudragit® coatings such methacrylic acid and methyl methacrylate polymers and others. The granules can be contained in capsules or compressed into tablets. In embodiments, the ODDF is applied as a coating, a layer or a band to the capsule or tablet. In embodiments, delayed release cores which are incorporated into tablets or capsules can also provide delayed release profiles. For example, gaboxadol or a pharmaceutically acceptable salt thereof can be mixed in a substance or a mixture of substances non-absorbable from the gastrointestinal tract but capable of slow dissolution or loss of drug by leaching, and an outer ODDF layer which is applied to the core by, e.g., compression or spraying. In embodiments, delayed release profiles may be provided by multiple layer tablets, each layer having different release properties. Multilayer tableting machines allow incorporation into one tablet of two or more separate layers which may be made to release drug at different rates after a period of delay. For example, one or more outer layers may be an ODDF, and each other layer a delayed release dosage form that exhibits different release rates. In embodiments, drug is incorporated into porous inert carriers that provide delayed release profiles. In embodiments, the porous inert carriers incorporate channels or passages from which the drug diffuses into surrounding fluids. In embodiments, drug is incorporated into an ion-exchange resin to provide a delayed release profile. Delayed action may result from a predetermined rate of release of the drug from the resin when the drug-resin complex contacts gastrointestinal fluids and the ionic constituents dissolved therein. In embodiments, membranes are utilized to control rate of release from drug containing reservoirs. In embodiments, liquid preparations may also be utilized to provide a delayed release profile. For example, a liquid preparation consisting of solid particles dispersed throughout a liquid phase in which the particles are not soluble. The suspension is formulated to allow at least a reduction in dosing frequency as compared to that drug presented as a conventional dosage form (e.g., as a solution or a prompt drug-releasing, conventional solid dosage form). For example, a suspension of ion-exchange resin constituents or microbeads.

In embodiments, modified release pharmaceutical compositions herein include pulsatile release dosage formulations (PRDFs). Pulsatile drug release involves rapid release of defined or discrete amounts of a drug (or drugs) such as gaboxadol or a pharmaceutically acceptable salt thereof after a lag time following an initial release of drug. In embodiments, PRDFs can provide a single pulse. In embodiments, PRDFs can provide multiple pulses over time. Various PRDFs are known to those with skill in the art.

In embodiments, a PRDF can be a capsule. In embodiments, release after a lag time is provided by a system that uses osmotic pressure to cause release of a plug. In this system, gaboxadol or a pharmaceutically acceptable salt thereof is contained in an insoluble capsule shell sealed by an osmotically responsive plug, e.g., a hydrogel, which is pushed away by swelling or erosion. When the seal is broken the drug is released as a pulse from the capsule body. Contact with gastrointestinal fluid or dissolution medium causes the plug to swell, either pushing itself out of the capsule or causing the capsule to rupture after the lag-time. Position & dimensions of the plug can control lag-time. For rapid release of drug effervescent or disintegrating agents may be added. Effervescent materials can cause an increase in pressure thus aiding or causing expulsion of the plug. Examples of suitable plug material may be swellable materials coated with permeable polymer (polymethacrylates), erodible compressed polymer (HPMC, polyvinyl alcohol), congealed melted polymer (glyceryl monooleate), and enzymatically controlled erodible polymers such as pectin. In embodiments, an insoluble capsule contains multiple drug compartments separated by osmotically activated plugs. When a first plug is exposed to the environmental fluids, the first compartment opens, drug is released and the adjacent plug is exposed. The process continues until no sealed compartment are left. Lag time between pulses can be further controlled by varying the thickness of the plug and the properties of the materials from which the plug is made. More hygroscopic materials will absorb fluid faster and will swell faster. In embodiments, a membrane may be substituted for the plug. If effervescent materials are included in one or more compartments, fluids pass through the membrane by osmosis and the effervescent action and pressure increase causes the membrane to rupture, thereby releasing the drug. In embodiments, the membrane(s) are erodible and dissolve to release the contents of the compartment(s). Varying the thickness, porosity and properties of materials of the membrane can allow further control of lag time between pulses. In embodiments, a PRDF can be a tablet. In embodiments, single pulse tablets involve a core containing gaboxadol or a pharmaceutically acceptable salt thereof surrounded by one or more layers of swellable, rupturable coatings. In embodiments, a rupturable coating surrounds a swellable layer. As the swellable layer expands, it causes the rupturable coating to rupture, thereby releasing the drug from the core. Swellable materials such as hydrogels are well known. In embodiments, an inner swelling layer can contain a superdisintegrant, e.g., croscarmellose sodium, and an outer rupturable layer can be made of a polymeric porous materials such as polyethylene oxides, ethylcellulose and the like. Porous film coats of sucrose may also be suitable. In embodiments, multiple pulse tablets incorporate multiple layers surrounding a core. As a first outermost layer erodes and releases the drug contained within the layer, an underlying layer is exposed, thus releasing drug after a predetermined lag time. The process repeats until the innermost core is exposed.

In embodiments, PRDFs can incorporate ODDFs that are solid dosage forms containing medicinal substances which disintegrate rapidly, usually within a matter of seconds, when placed upon the tongue, but which also releases a drug (or drugs) in pulsatile fashion. Accordingly, in embodiments, modified release dosage forms herein can incorporate an ODDF aspect to provide immediate release of a loading dose and a PRDF aspect that provides a period in which there is no drug delivery (lag time) followed by pulsatile drug delivery to provide drug levels in the blood within a desired therapeutic range for a desirable period of time in excess of the activity resulting from a single dose of the drug. In embodiments, the ODDF aspect releases the drug immediately and then, after a period of delay, the PRDF aspect thereafter provides a single pulse release of drug to provide an additional period of activity. In embodiments, the ODDF aspect releases the drug immediately and then, after a period of delay, the PRFD aspect thereafter provides multiple pulsatile release of drug for prolonged therapeutic effect.

In embodiments, an ODDF is applied as a coating or band over a PRDF, or as a layer adjacent to a PRDF, to allow direct exposure of the ODDF to the oral cavity and consequent disintegration of the ODDF. In embodiments, the ODDF and a PRDF can be mixed in a chewable resin, e.g., gum. Those skilled in the art are familiar with techniques for applying coatings, bands and layers to fabricate pharmaceutical dosage forms.

In embodiments, the modified release pharmaceutical compositions include 0.1 mg to 75 mg, 0.1 mg to 70 mg, 0.1 mg to 65 mg, 0.1 mg to 55 mg, 0.1 mg to 50 mg, 0.1 mg to 45 mg, 0.1 mg to 40 mg, 0.1 mg to 35 mg, 0.1 mg to 30 mg, 0.1 mg to 25 mg, 0.1 mg to 20 mg, 0.1 mg to 15 mg, 0.1 mg to 10 mg, 0.5 mg to 75 mg, 0.5 mg to 70 mg, 0.5 mg to 65 mg, 0.5 mg to 55 mg, 0.5 mg to 50 mg, 0.5 mg to 45 mg, 0.5 mg to 40 mg, 0.5 mg to 35 mg, 0.5 mg to 30 mg, 0.5 mg to 25 mg, 0.5 mg to 20 mg, 0.5 to 15 mg, 0.5 to 10 mg, 1 mg to 75 mg, 1 mg to 70 mg, 1 mg to 65 mg, 1 mg to 55 mg, 1 mg to 50 mg, 1 mg to 45 mg, 1 mg to 40 mg, 1 mg to 35 mg, 1 mg to 30 mg, 1 mg to 25 mg, 1 mg to 20 mg, 1 mg to 15 mg, 1 mg to 10 mg, 1.5 mg to 75 mg, 1.5 mg to 70 mg, 1.5 mg to 65 mg, 1.5 mg to 55 mg, 1.5 mg to 50 mg, 1.5 mg to 45 mg, 1.5 mg to 40 mg, 1.5 mg to 35 mg, 1.5 mg to 30 mg, 1.5 mg to 25 mg, 1.5 mg to 20 mg, 1.5 mg to 15 mg, 1.5 mg to 10 mg, 2 mg to 75 mg, 2 mg to 70 mg, 2 mg to 65 mg, 2 mg to 55 mg, 2 mg to 50 mg, 2 mg to 45 mg, 2 mg to 40 mg, 2 mg to 35 mg, 2 mg to 30 mg, 2 mg to 25 mg, 2 mg to 20 mg, 2 mg to 15 mg, 2 mg to 10 mg, 2.5 mg to 75 mg, 2.5 mg to 70 mg, 2.5 mg to 65 mg, 2.5 mg to 55 mg, 2.5 mg to 50 mg, 2.5 mg to 45 mg, 2.5 mg to 40 mg, 2.5 mg to 35 mg, 2.5 mg to 30 mg, 2.5 mg to 25 mg, 2.5 mg to 20 mg, 2.5 mg to 15 mg, 2.5 mg to 10 mg, 3 mg to 75 mg, 3 mg to 70 mg, 3 mg to 65 mg, 3 mg to 55 mg, 3 mg to 50 mg, 3 mg to 45 mg, 3 mg to 40 mg, 3 mg to 35 mg, 3 mg to 30 mg, 3 mg to 25 mg, 3 mg to 20 mg, 3 mg to 15 mg, 3 mg to 10 mg, 3.5 mg to 75 mg, 3.5 mg to 70 mg, 3.5 mg to 65 mg, 3.5 mg to 55 mg, 3.5 mg to 50 mg, 3.5 mg to 45 mg, 3.5 mg to 40 mg, 3.5 mg to 35 mg, 3.5 mg to 30 mg, 3.5 mg to 25 mg, 3.5 mg to 20 mg, 3.5 mg to 15 mg, 3.5 mg to 10 mg, 4 mg to 75 mg, 4 mg to 70 mg, 4 mg to 65 mg, 4 mg to 55 mg, 4 mg to 50 mg, 4 mg to 45 mg, 4 mg to 40 mg, 4 mg to 35 mg, 4 mg to 30 mg, 4 mg to 25 mg, 4 mg to 20 mg, 4 mg to 15 mg, 4 mg to 10 mg, 4.5 mg to 75 mg, 4.5 mg to 70 mg, 4.5 mg to 65 mg, 4.5 mg to 55 mg, 4.5 mg to 50 mg, 4.5 mg to 45 mg, 4.5 mg to 40 mg, 4.5 mg to 35 mg, 4.5 mg to 30 mg, 4.5 mg to 25 mg, 4.5 mg to 20 mg, 4.5 mg to 15 mg, 4.5 mg to 10 mg, 5 mg to 75 mg, 5 mg to 70 mg, 5 mg to 65 mg, 5 mg to 55 mg, 5 mg to 50 mg, 5 mg to 45 mg, 5 mg to 40 mg, 5 mg to 35 mg, 5 mg to 30 mg, 5 mg to 25 mg, 5 mg to 20 mg, 5 mg to 15 mg, or 5 mg to 10 mg, gaboxadol or a pharmaceutically acceptable salt thereof.

In embodiments, pharmaceutical compositions include 5 mg to 20 mg, 5 mg to 10 mg, 4 mg to 6 mg, 6 mg to 8 mg, 8 mg to 10 mg, 10 mg to 12 mg, 12 mg to 14 mg, 14 mg to 16 mg, 16 mg to 18 mg, or 18 mg to 20 mg gaboxadol or a pharmaceutically acceptable salt thereof.

In embodiments, pharmaceutical compositions include 0.1 mg, 0.25 mg, 0.5 mg, 1 mg, 2.5 mg, 3 mg, 4 mg, 5 mg, 7 mg, 7.5 mg, 10 mg, 12.5 mg, 15 mg, 17.5 mg, or 20 mg gaboxadol or a pharmaceutically acceptable salt thereof or amounts that are multiples of such doses. In embodiments, pharmaceutical compositions include 2.5 mg, 5 mg, 7.5 mg, 10 mg, 15 mg, or 20 mg gaboxadol or a pharmaceutically acceptable salt thereof.

In embodiments, ODDFs include 0.05 mg, 0.1 mg, 0.25 mg, 0.5 mg, 0.75 mg, 1 mg, 1.25 mg, 1.5 mg, 1.75 mg, 2 mg, 2.5 mg, 3 mg, 3.5 mg, 4 mg, 4.5 mg, 5 mg, 7 mg, 7.5 mg, 10 mg, 12.5 mg, 15 mg, 17.5 mg, or 20 mg gaboxadol or a pharmaceutically acceptable salt thereof or amounts that are multiples of such doses.

In embodiments, ERDFs include from about 1 mg to about 100 mg gaboxadol or a pharmaceutically acceptable salt thereof. In embodiments, ERDFs include 5 mg, 6 mg, 7 mg, 8 mg, 9 mg, 10 mg, 11 mg, 12 mg, 13 mg, 14 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, or 100 mg gaboxadol or a pharmaceutically acceptable salt thereof.

In embodiments, delayed release dosage forms include from about 0.05 mg to about 100 mg gaboxadol or a pharmaceutically acceptable salt thereof. In embodiments, delayed release dosage forms include 0.05 mg, 0.1 mg, 0.25 mg, 0.5 mg, 0.75 mg, 1 mg, 1.25 mg, 1.5 mg, 1.75 mg, 2 mg, 2.5 mg, 3 mg, 3.5 mg, 4 mg, 4.5 mg, 5 mg, 6 mg, 7 mg, 8 mg, 9 mg, 10 mg, 11 mg, 12 mg, 13 mg, 14 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, or 100 mg gaboxadol or a pharmaceutically acceptable salt thereof.

In embodiments, PRDFs include one or more pulse providing domains having from about 0.05 mg to about 100 mg gaboxadol or a pharmaceutically acceptable salt thereof. In embodiments, PRDFs include 0.05 mg, 0.1 mg, 0.25 mg, 0.5 mg, 0.75 mg, 1 mg, 1.25 mg, 1.5 mg, 1.75 mg, 2 mg, 2.5 mg, 3 mg, 3.5 mg, 4 mg, 4.5 mg, 5 mg, 6 mg, 7 mg, 8 mg, 9 mg, 10 mg, 11 mg, 12 mg, 13 mg, 14 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, or 100 mg gaboxadol or a pharmaceutically acceptable salt thereof.

In embodiments, the pharmaceutical compositions described herein are administered once, twice, or three times daily, or every other day. In embodiments, a pharmaceutical composition described herein is provided to the patient in the evening. In embodiments, a pharmaceutical composition described herein is provided to the patient in the morning. In embodiments, a pharmaceutical composition described herein is provided to the patient once in the evening and once in the morning. In embodiments, the total amount of gaboxadol or a pharmaceutically acceptable salt thereof administered to a subject in a 24-hour period is 1 mg to 30 mg. In embodiments, the total amount of gaboxadol or a pharmaceutically acceptable salt thereof administered to a subject in a 24-hour period is 0.05 mg to 30 mg, e.g., 1 mg to 20 mg. In embodiments, the total amount of gaboxadol or a pharmaceutically acceptable salt thereof administered to a subject in a 24-hour period is 5 mg, 10 mg, or 15 mg. In embodiments, the total amount of gaboxadol or a pharmaceutically acceptable salt thereof administered to a subject in a 24-hour period is 20 mg. In embodiments, the subject may be started at a low dose and the dosage is escalated. In this manner, it can be determined if the drug is well tolerated in the subject. In embodiments, the effect of gaboxadol or a pharmaceutical salt thereof, either alone or in combination with a hypoglycemic agent, is adjusted according to the patient's response. Dosages can be lower for children than for adults. In embodiments, a dose of gaboxadol or a pharmaceutically acceptable salt thereof for children can be 0.1 mg/kg to 1 mg/kg.

In embodiments, provided herein are methods of treating a metabolic disorder such as type 1 diabetes, type 2 diabetes or pre-diabetes including administering to a patient in need thereof a pharmaceutical composition including gaboxadol or a pharmaceutically acceptable salt thereof wherein the composition provides improvement in at least one symptom of the metabolic disorder. In embodiments, methods of treating metabolic disorder such as type 1 diabetes, type 2 diabetes or pre-diabetes by administering to a subject in need thereof an effective amount of gaboxadol or a pharmaceutically acceptable salt, derivative or analogue, or combination thereof, are provided. An effective amount or therapeutically effective amount can be a dosage sufficient to treat, inhibit, or alleviate one or more symptoms of the metabolic disorder discussed previously, or to provide a desired pharmacologic and/or physiologic effect, for example, reducing, inhibiting, or reversing one or more of the underlying pathophysiological mechanisms underlying the metabolic disorder. The precise dosage will vary according to a variety of factors such as subject-dependent variables (e.g., age, immune system health, clinical symptoms etc.).

In embodiments, provided herein are methods of treating a metabolic disorder such as type 1 diabetes, type 2 diabetes or pre-diabetes including administering to a patient in need thereof a pharmaceutical composition including gaboxadol or a pharmaceutically acceptable salt thereof wherein the composition provides improvement of at least one symptom for more than 4 hours after administration of the pharmaceutical composition to the patient. In embodiments, provided herein is improvement of at least one symptom for more than 6 hours after administration of the pharmaceutical composition to the patient. In embodiments, provided herein is improvement of at least one symptom for more than, e.g., 8 hours, 10 hours, 12 hours, 15 hours, 18 hours, 20 hours, or 24 hours after administration of the pharmaceutical composition to the patient. In embodiments, provided herein is improvement in at least one symptom for at least, e.g., 8 hours, 10 hours, 12 hours, 15 hours, 18 hours, 20 hours, or 24 hours after administration of the pharmaceutical composition to the patient. In embodiments, provided herein is improvement in at least one symptom for 12 hours after administration of the pharmaceutical composition to the patient.

In embodiments, methods of treating a metabolic disorder such as type 1 diabetes, type 2 diabetes or pre-diabetes include administration of gaboxadol or a pharmaceutically acceptable salt thereof in combination with one or more other active agents. The combination therapies can include administration of the active agents together in the same admixture, or in separate admixtures. In embodiments, the pharmaceutical composition includes two, three, or more active agents. In embodiments, the combinations result in a more than additive effect on the treatment of the disease or disorder. For example, the combination of the gaboxadol or a pharmaceutically acceptable salt thereof and one or more hypoglycemic agents provides a therapeutic benefit greater than the additive effect of administering the same dosage of each of the gaboxadol or a pharmaceutically acceptable salt thereof and the hypoglycemic agents alone. Thus, treatment is provided of a metabolic disorder with a combination of agents that combined, may provide a synergistic effect that enhances efficacy.

In embodiments, administration of gaboxadol or a pharmaceutically acceptable salt thereof, alone or optionally in combination with one or more hypoglycemic agents such as a biguanide, a dipeptidyl peptidase-4 (DPP-4) inhibitor, a sulphonylurea, a thiazolidinedione, a meglitinide glinide), an alpha-glucosidase blocker, an glucagon-like peptide-1 receptor agonist, insulin or an insulin analog to a patient in need thereof is provided. In embodiments, a pharmaceutical composition of gaboxadol or a pharmaceutically acceptable salt thereof, alone or optionally in combination with one or more hypoglycemic agents such as a biguanide, a dipeptidyl peptidase-4 (DPP-4) inhibitor, a sulphonylurea, a thiazolidinedione, a meglitinide (glinide), an alpha-glucosidase blocker, an glucagon-like peptide-1 receptor agonist, insulin or an insulin analog is provided.

In embodiments, a patient in need thereof is administered gaboxadol or a pharmaceutically acceptable salt thereof in combination with a biguanide or a pharmaceutically acceptable salt thereof. In embodiments, a patient in need thereof is administered a pharmaceutical composition including gaboxadol or a pharmaceutically acceptable salt thereof in combination with a biguanide or a pharmaceutically acceptable salt thereof. Biguanides include metformin, buformin and phenformin. Biguanides may be provided as an acid addition salt. For example, metformin, buformin and phenformin acid addition salts, include but are not limited to hydrochloric, maleic, fumaric, benzoic, ascorbic, succinic, oxalic, bis-methylenesalicylic, methanesulfonic, ethane-disulfonic, acetic, propionic, tartaric, salicylic, citric, gluconic, lactic, malic, mandelic, cinnamic, citraconic, aspartic, stearic, palmitic, itaconic, glycolic, p-amino-benzoic, glutamic, benzene sulfonic or theophylline acetic acid addition salts, as well as the 8-halotheophyllines, for example 8-bromo-theophylline. In embodiments, inorganic acid addition salts, including but not limited to, hydrochloric, hydrobromic, sulfuric, sulfamic, phosphoric or nitric acid addition salts may be used. Fatty acid salts may be used, e.g., laureate, succinate, caprate, palmitate, etc. Hydroxyacid salts may be used, including salts of hydroxy-aliphatic dicarboxylic acids, such as mesotartaric acid, tartaric acid, mesoxalic acids and oxidised maleates. Other salts may include pamoate, p-chlorophenoxyacetic, acetylsalicylic, nicotinic, and the like.

In embodiments, methods of treating a metabolic disorder such as type 1 diabetes, type 2 diabetes or pre-diabetes herein include, in addition to gaboxadol or a pharmaceutically acceptable salt thereof, administering to a patient in need thereof about 50 mg to about 3000 mg metformin or a pharmaceutically acceptable salt thereof. In embodiments, methods of treating a metabolic disorder such as type 1 diabetes, type 2 diabetes or pre-diabetes herein include administering gaboxadol or a pharmaceutically acceptable salt thereof, in combination with metformin or a pharmaceutically acceptable salt thereof. In embodiments, about 50 mg to about 3000 mg of metformin or a pharmaceutically acceptable salt thereof may be administered in 24 hours. In embodiments, the metformin or a pharmaceutically acceptable salt thereof may be administered in divided doses over 24 hours. In embodiments, metformin may be administered once a day, e.g., with an evening meal. In embodiments, metformin can be given in doses varying from about 500 mg to 2000 mg up to 2500 mg or 3000 mg per day using various dosing regimens from about 100 mg to 500 mg or 200 mg to 850 mg (1-3 times a day), or about 300 mg to 1000 mg once or twice a day, or delayed-release metformin in doses of about 100 mg to 1000 mg or 500 mg to 1000 mg once or twice a day or about 500 mg to 2000 mg once a day. Particular dosage strengths may be 250, 500, 625, 750, 850 and 1000 mg of metformin hydrochloride.

In embodiments, the patient is administered 50 mg to 75 mg, 75 mg to 100 mg, 100 mg to 125 mg, 125 mg to 150 mg, 150 mg to 175 mg, 175 mg to 200 mg, 200 mg to 225 mg, 225 mg to 250 mg, 250 mg to 275 mg, 275 mg to 300 mg, 300 mg, to 325 mg, 325 mg to 350 mg, 350 mg to 375 mg, 375 mg to 400 mg, 400 mg to 425 mg, 425 mg to 450 mg, 450 mg to 475 mg, 475 mg to 500 mg, 500 mg to 525 mg, 525 mg to 550 mg, 550 mg to 575 mg, 575 mg to 600 mg, 600 mg to 625 mg, 625 mg to 650 mg, 650 mg to 675 mg, 675 mg to 700 mg, 700 mg to 725 mg, 725 mg to 750 mg, 750 mg to 775 mg, 775 mg to 800 mg, 800 mg to 825 mg, 825 mg to 850 mg, 850 mg to 875 mg, 875 mg to 900 mg, 900 mg to 925 mg, 925 mg to 950 mg, 950 mg to 975 mg, 975 mg to 1000 mg, 1000 mg to 1025 mg, 1025 mg to 1050 mg, 1050 mg to 1075 mg, 1075 mg to 1100 mg, 1100 mg to 1125 mg, 1125 mg to 1150 mg, 1150 mg to 1175 mg, 1175 mg to 1200 mg, 1200 mg to 1225 mg, 1225 mg to 1250 mg, 1250 mg to 1275 mg, 1275 mg to 1300 mg, 1300 mg to 1325 mg, 1325 mg to 1350 mg, 1350 mg to 1375 mg, 1375 mg to 1400 mg, 1400 mg to 1425 mg, 1425 mg to 1450 mg, 1450 mg to 1475 mg, 1475 mg to 1500 mg, 1500 mg to 1525 mg, 1525 mg to 1550 mg, 1550 mg to 1575 mg, 1575 mg to 1600 mg, 1600 mg to 1625 mg, 1625 mg to 1650 mg, 1650 mg to 1675 mg, 1675 mg to 1700 mg, 1700 mg to 1725 mg, 1725 mg to 1750 mg, 1750 mg to 1775 mg, 1775 mg to 1800 mg, 1800 mg to 1825 mg, 1825 mg to 1850 mg, 1850 mg to 1875 mg, 1875 mg to 1900 mg, 1900 mg to 1925 mg, 1925 mg to 1950 mg, 1950 mg to 1975 mg, 1975 mg to 2000 mg, 2000 mg to 2025 mg, 2025 mg to 2050 mg, 2050 mg to 2075 mg, 2075 mg to 2100 mg, 2100 mg to 2125 mg, 2125 mg to 2150 mg, 2150 mg to 2175 mg, 2175 mg to 2200 mg, 2200 mg to 2225 mg, 2225 mg to 2250 mg, 2250 mg to 2275 mg, 2275 mg to 2300 mg, 2300 mg to 2325 mg, 2325 mg to 2350 mg, 2350 mg to 2375 mg, 2375 mg to 2400 mg, 2400 mg to 2425 mg, 2425 mg to 2450 mg, 2450 mg to 2475 mg, 2475 mg to 2500 mg, 2500 mg to 2525 mg, 2525 mg to 2550 mg, 2550 mg to 2575 mg, 2575 mg to 2600 mg, 2600 mg to 2625 mg, 2625 mg to 2650 mg, 2650 mg to 2675 mg, 2675 mg to 2700 mg, 2700 mg to 2725 mg, 2725 mg to 2750 mg, 2750 mg to 2775 mg, 2775 mg to 2800 mg, 2800 mg to 2825 mg, 2825 mg to 2850 mg, 2850 mg to 2875 mg, 2875 mg to 2900 mg, 2900 mg to 2925 mg, 2925 mg to 2950 mg, 2950 mg to 2975 mg, or 2975 mg to 3000 mg, metformin or a pharmaceutically acceptable salt thereof.

In embodiments, the patient is administered 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1225 mg, 1250 mg, 1275 mg, 1300 mg, 1325 mg, 1350 mg, 1375 mg, 1400 mg, 1425 mg, 1450 mg, 1475 mg, 1500 mg, 1525 mg, 1550 mg, 1575 mg, 1600 mg, 1625 mg, 1650 mg, 1675 mg, 1700 mg, 1725 mg, 1750 mg, 1775 mg, 1800 mg, 1825 mg, 1850 mg, 1875 mg, 1900 mg, 1925 mg, 1950 mg, 1975 mg, 2000 mg, 2025 mg, 2250 mg, 2275 mg, 2300 mg, 2325 mg, 2350 mg, 2375 mg, 2400 mg, 2425 mg, 2450 mg, 2475 mg, 2500 mg, 2525 mg, 2550 mg, 2575 mg, 2600 mg, 2625 mg, 2650 mg, 2675 mg, 2700 mg, 2725 mg, 2750 mg, 2775 mg, 2800 mg, 2825 mg, 2850 mg, 2875 mg, 2900 mg, 2925 mg, 2950 mg, 2975 mg, or 3000 mg, metformin or a pharmaceutically acceptable salt thereof.

In embodiments methods of treating a metabolic disorder such as type 1 diabetes, type 2 diabetes or pre-diabetes include administering to a patient in need thereof a pharmaceutical composition including gaboxadol or a pharmaceutically acceptable salt thereof in combination with about 50 mg to about 3000 mg metformin or a pharmaceutically acceptable salt thereof.

In embodiments, the pharmaceutical compositions include 50 mg to 75 mg, 75 mg to 100 mg, 100 mg to 125 mg, 125 mg to 150 mg, 150 mg to 175 mg, 175 mg to 200 mg, 200 mg to 225 mg, 225 mg to 250 mg, 250 mg to 275 mg, 275 mg to 300 mg, 300 mg to 325 mg, 325 mg to 350 mg, 350 mg to 375 mg, 375 mg to 400 mg, 400 mg to 425 mg, 425 mg to 450 mg, 450 mg to 475 mg, 475 mg to 500 mg, 500 mg to 525 mg, 525 mg to 550 mg, 550 mg to 575 mg, 575 mg to 600 mg, 600 mg to 625 mg, 625 mg to 650 mg, 650 mg to 675 mg, 675 mg to 700 mg, 700 mg to 725 mg, 725 mg to 750 mg, 750 mg to 775 mg, 775 mg to 800 mg, 800 mg to 825 mg, 825 mg to 850 mg, 850 mg to 875 mg, 875 mg to 900 mg, 900 mg to 925 mg, 925 mg to 950 mg, 950 mg to 975 mg, 975 mg to 1000 mg, 1000 mg to 1025 mg, 1025 mg to 1050 mg, 1050 mg to 1075 mg, 1075 mg to 1100 mg, 1100 mg to 1125 mg, 1125 mg to 1150 mg, 1150 mg to 1175 mg, 1175 mg to 1200 mg, 1200 mg to 1225 mg, 1225 mg to 1250 mg, 1250 mg to 1275 mg, 1275 mg to 1300 mg, 1300 mg to 1325 mg, 1325 mg to 1350 mg, 1350 mg to 1375 mg, 1375 mg to 1400 mg, 1400 mg to 1425 mg, 1425 mg to 1450 mg, 1450 mg to 1475 mg, 1475 mg to 1500 mg, 1500 mg to 1525 mg, 1525 mg to 1550 mg, 1550 mg to 1575 mg, 1575 mg to 1600 mg, 1600 mg to 1625 mg, 1625 mg to 1650 mg, 1650 mg to 1675 mg, 1675 mg to 1700 mg, 1700 mg to 1725 mg, 1725 mg to 1750 mg, 1750 mg to 1775 mg, 1775 mg to 1800 mg, 1800 mg to 1825 mg, 1825 mg to 1850 mg, 1850 mg to 1875 mg, 1875 mg to 1900 mg, 1900 mg to 1925 mg, 1925 mg to 1950 mg, 1950 mg to 1975 mg, 1975 mg to 2000 mg, 2000 mg to 2025 mg, 2025 mg to 2050 mg, 2050 mg to 2075 mg, 2075 mg to 2100 mg, 2100 mg to 2125 mg, 2125 mg to 2150 mg, 2150 mg to 2175 mg, 2175 mg to 2200 mg, 2200 mg to 2225 mg, 2225 mg to 2250 mg, 2250 mg to 2275 mg, 2275 mg to 2300 mg, 2300 mg to 2325 mg, 2325 mg to 2350 mg, 2350 mg to 2375 mg, 2375 mg to 2400 mg, 2400 mg to 2425 mg, 2425 mg to 2450 mg, 2450 mg to 2475 mg, 2475 mg to 2500 mg, 2500 mg to 2525 mg, 2525 mg to 2550 mg, 2550 mg to 2575 mg, 2575 mg to 2600 mg, 2600 mg to 2625 mg, 2625 mg to 2650 mg, 2650 mg to 2675 mg, 2675 mg to 2700 mg, 2700 mg to 2725 mg, 2725 mg to 2750 mg, 2750 mg to 2775 mg, 2775 mg to 2800 mg, 2800 mg to 2825 mg, 2825 mg to 2850 mg, 2850 mg to 2875 mg, 2875 mg to 2900 mg, 2900 mg to 2925 mg, 2925 mg to 2950 mg, 2950 mg to 2975 mg, 2975 mg to 3000 mg, metformin or a pharmaceutically acceptable salt thereof.

In embodiments, the pharmaceutical compositions include 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1225 mg, 1250 mg, 1275 mg, 1300 mg, 1325 mg, 1350 mg, 1375 mg, 1400 mg, 1425 mg, 1450 mg, 1475 mg, 1500 mg, 1525 mg, 1550 mg, 1575 mg, 1600 mg, 1625 mg, 1650 mg, 1675 mg, 1700 mg, 1725 mg, 1750 mg, 1775 mg, 1800 mg, 1825 mg, 1850 mg, 1875 mg, 1900 mg, 1925 mg, 1950 mg, 1975 mg, 2000 mg, 2025 mg, 2250 mg, 2275 mg, 2300 mg, 2325 mg, 2350 mg, 2375 mg, 2400 mg, 2425 mg, 2450 mg, 2475 mg, 2500 mg, 2525 mg, 2550 mg, 2575 mg, 2600 mg, 2625 mg, 2650 mg, 2675 mg, 2700 mg, 2725 mg, 2750 mg, 2775 mg, 2800 mg, 2825 mg, 2850 mg, 2875 mg, 2900 mg, 2925 mg, 2950 mg, 2975 mg, 3000 mg, metformin or a pharmaceutically acceptable salt thereof.

In embodiments, methods of treating a metabolic disorder such as type 1 diabetes, type 2 diabetes or pre-diabetes include in addition to gaboxadol or a pharmaceutically acceptable salt thereof, administering to a patient in need thereof about 10 mg to about 500 mg buformin or a pharmaceutically acceptable salt thereof. In embodiments, methods of treating a metabolic disorder such as type 1 diabetes, type 2 diabetes or pre-diabetes herein include administering gaboxadol or a pharmaceutically acceptable salt thereof, in combination with buformin or a pharmaceutically acceptable salt thereof. In embodiments, the amount of buformin or a pharmaceutically acceptable salt thereof is administered in 24 hours. In embodiments, the buformin or a pharmaceutically acceptable salt thereof is administered in divided doses over 24 hours.

In embodiments, the patient is administered 10 mg to 15 mg, 15 mg to 20 mg, 20 mg to 25 mg, 25 mg to 30 mg, 30 mg to 35 mg, 35 mg to 40 mg, 40 mg to 45 mg, 45 mg to 50 mg, 50 mg to 55 mg, 55 mg to 60 mg, 60 mg to 75 mg, 75 mg, to 80 mg, 80 mg to 85 mg, 85 mg to 90 mg, 90 mg to 95 mg, 95 mg to 100 mg, 100 mg to 110 mg, 110 mg to 115 mg, 115 mg to 120 mg, 125 mg to 130 mg, 130 mg to 135 mg, 135 mg to 140 mg, 140 mg to 145 mg, 145 mg to 150 mg, 150 mg to 155 mg, 155 mg to 160 mg, 160 mg, to 165 mg, 165 mg to 170 mg, 175 mg to 180 mg, 180 mg to 185 mg, 185 mg to 190 mg, 190 mg to 195 mg, 195 mg to 200 mg, 200 mg to 225 mg, 225 mg to 250 mg, 250 mg to 275 mg, 275 mg to 300 mg, 300 mg to 325 mg, 325 mg to 350 mg, 350 mg to 375 mg, 375 mg to 400 mg, 400 mg to 425 mg, 425 mg to 450 mg, 450 mg to 475 mg, or 475 mg to 500 mg, buformin or a pharmaceutically acceptable salt thereof.

In embodiments, the patient is administered 10 mg, 15 mg, 20 mg, 25 mg, 30 mg, 35 mg, 40 mg, 45 mg, 50 mg, 55 mg, 60 mg, 75 mg, 80 mg, 85 mg, 90 mg, 95 mg, 100 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 225 mg, 250 mg, 275 mg, 300 mg, 325 mg, 350 mg, 375 mg, 400 mg, 425 mg, 450 mg, 475 mg, or 500 mg, buformin or a pharmaceutically acceptable salt thereof.

In embodiments, methods of treating a metabolic disorder such as type 1 diabetes, type 2 diabetes or pre-diabetes include administering to a patient in need thereof a pharmaceutical composition including gaboxadol or a pharmaceutically acceptable salt thereof, in combination with about 10 mg to about 500 mg buformin or a pharmaceutically acceptable salt thereof.

In embodiments, the compositions include 10 mg to 15 mg, 15 mg to 20 mg, 20 mg to 25 mg, 25 mg to 30 mg, 30 mg to 35 mg, 35 mg to 40 mg, 40 mg to 45 mg, 45 mg to 50 mg, 50 mg to 55 mg, 55 mg to 60 mg, 60 mg to 75 mg, 75 mg, to 80 mg, 80 mg to 85 mg, 85 mg to 90 mg, 90 mg to 95 mg, 95 mg to 100 mg, 100 mg to 110 mg, 110 mg to 115 mg, 115 mg to 120 mg, 125 mg to 130 mg, 130 mg to 135 mg, 135 mg to 140 mg, 140 mg to 145 mg, 145 mg to 150 mg, 150 mg to 155 mg, 155 mg to 160 mg, 160 mg, to 165 mg, 165 mg to 170 mg, 175 mg to 180 mg, 180 mg to 185 mg, 185 mg to 190 mg, 190 mg to 195 mg, 195 to 200 mg, 200 mg to 225 mg, 225 mg to 250 mg, 250 mg to 275 mg, 275 mg to 300 mg, 300 mg to 325 mg, 325 mg to 350 mg, 350 mg to 375 mg, 375 mg to 400 mg, 400 mg to 425 mg, 425 mg to 450 mg, 450 mg to 475 mg, or 475 mg to 500 mg, buformin or a pharmaceutically acceptable salt thereof.

In embodiments, the compositions include 10 mg, 15 mg, 20 mg, 25 mg, 30 mg, 35 mg, 40 mg, 45 mg, 50 mg, 55 mg, 60 mg, 75 mg, 80 mg, 85 mg, 90 mg, 95 mg, 100 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 225 mg, 250 mg, 275 mg, 300 mg, 325 mg, 350 mg, 375 mg, 400 mg, 425 mg, 450 mg, 475 mg, or 500 mg, buformin or a pharmaceutically acceptable salt thereof.

In embodiments, methods of treating a metabolic disorder such as type 1 diabetes, type 2 diabetes or pre-diabetes include, in addition to gaboxadol or a pharmaceutically acceptable salt thereof, administering to a patient in need thereof about 10 mg to about 300 mg phenformin or a pharmaceutically acceptable salt thereof. In embodiments, methods of treating a metabolic disorder such as type 1 diabetes, type 2 diabetes or pre-diabetes herein include administering gaboxadol or a pharmaceutically acceptable salt thereof, in combination with phenformin or a pharmaceutically acceptable salt thereof. In embodiments, the amount of phenformin or a pharmaceutically acceptable salt thereof is administered in 24 hours. In embodiments, the phenformin or a pharmaceutically acceptable salt thereof is administered in divided doses over 24 hours.

In embodiments, the patient is administered 10 mg to 15 mg, 15 mg to 20 mg, 20 mg to 25 mg, 25 mg to 30 mg, 30 mg to 35 mg, 35 mg to 40 mg, 40 mg to 45 mg, 45 mg to 50 mg, 50 mg to 55 mg, 55 mg to 60 mg, 60 mg to 75 mg, 75 mg, to 80 mg, 80 mg to 85 mg, 85 mg to 90 mg, 90 mg to 95 mg, 95 mg to 100 mg, 100 mg to 110 mg, 110 mg to 115 mg, 115 mg to 120 mg, 125 mg to 130 mg, 130 mg to 135 mg, 135 mg to 140 mg, 140 mg to 145 mg, 145 mg to 150 mg, 150 mg to 155 mg, 155 mg to 160 mg, 160 mg, to 165 mg, 165 mg to 170 mg, 175 mg to 180 mg, 180 mg to 185 mg, 185 mg to 190 mg, 190 mg to 195 mg, 195 to 200 mg, 200 mg to 225 mg, 225 mg to 250 mg, 250 mg to 275 mg, or 275 mg to 300 mg, phenformin or a pharmaceutically acceptable salt thereof.

In embodiments, the patient is administered 10 mg, 15 mg, 20 mg, 25 mg, 30 mg, 35 mg, 40 mg, 45 mg, 50 mg, 55 mg, 60 mg, 75 mg, 80 mg, 85 mg, 90 mg, 95 mg, 100 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 225 mg, 250 mg, 275 mg, or 300 mg, phenformin or a pharmaceutically acceptable salt thereof.

In embodiments methods of treating a metabolic disorder such as type 1 diabetes, type 2 diabetes or pre-diabetes include, administering to a patient in need thereof a pharmaceutical composition including gaboxadol or a pharmaceutically acceptable salt thereof, in combination with about 10 mg to about 300 mg phenformin or a pharmaceutically acceptable salt thereof.

In embodiments, the compositions include 10 mg to 15 mg, 15 mg to 20 mg, 20 mg to 25 mg, 25 mg to 30 mg, 30 mg to 35 mg, 35 mg to 40 mg, 40 mg to 45 mg, 45 mg to 50 mg, 50 mg to 55 mg, 55 mg to 60 mg, 60 mg to 75 mg, 75 mg, to 80 mg, 80 mg to 85 mg, 85 mg to 90 mg, 90 mg to 95 mg, 95 mg to 100 mg, 100 mg to 110 mg, 110 mg to 115 mg, 115 mg to 120 mg, 125 mg to 130 mg, 130 mg to 135 mg, 135 mg to 140 mg, 140 mg to 145 mg, 145 mg to 150 mg, 150 mg to 155 mg, 155 mg to 160 mg, 160 mg, to 165 mg, 165 mg to 170 mg, 175 mg to 180 mg, 180 mg to 185 mg, 185 mg to 190 mg, 190 mg to 195 mg, 195 to 200 mg, 200 mg to 225 mg, 225 mg to 250 mg, 250 mg to 275 mg, or 275 mg to 300 mg, phenformin or a pharmaceutically acceptable salt thereof.

In embodiments, the compositions include 10 mg, 15 mg, 20 mg, 25 mg, 30 mg, 35 mg, 40 mg, 45 mg, 50 mg, 55 mg, 60 mg, 75 mg, 80 mg, 85 mg, 90 mg, 95 mg, 100 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 225 mg, 250 mg, 275 mg, or 300 mg, phenformin or a pharmaceutically acceptable salt thereof.

In embodiments, a patient in need thereof is administered gaboxadol or a pharmaceutically acceptable salt thereof in combination with a DPP-4 inhibitor or a pharmaceutically acceptable salt thereof. In embodiments a patient in need thereof is administered a pharmaceutical composition including gaboxadol or a pharmaceutically acceptable salt thereof in combination with a DPP-4 inhibitor or a pharmaceutically acceptable salt thereof. Examples of DPP-4 inhibitors include sitagliptin, vildagliptin, saxagliptin, linagliptin, gemigliptin, anagliptin, teneligliptin, alogliptin, trelagliptin, omarigliptin, evogliptin, dutogliptin, and berberine.

In embodiments, methods of treating a metabolic disorder such as type 1 diabetes, type 2 diabetes or pre-diabetes herein include, in addition to gaboxadol or a pharmaceutically acceptable salt thereof, administering to a patient in need thereof about 10 mg to about 500 mg sitagliptin or a pharmaceutically acceptable salt thereof. In embodiments, methods of treating a metabolic disorder such as type 1 diabetes, type 2 diabetes or pre-diabetes herein include administering a pharmaceutical composition including gaboxadol or a pharmaceutically acceptable salt thereof, in combination with sitagliptin or a pharmaceutically acceptable salt thereof. In embodiments, about 10 mg to about 100 mg of sitagliptin or a pharmaceutically acceptable salt thereof may be administered in 24 hours. In embodiments, about 15 mg to about 100 mg of sitagliptin or a pharmaceutically acceptable salt thereof may be administered in 24 hours. In embodiments, about 20 mg to about 200 mg of sitagliptin or a pharmaceutically acceptable salt thereof may be administered in 24 hours. In embodiments, about 25 mg to about 100 mg of sitagliptin or a pharmaceutically acceptable salt thereof may be administered in 24 hours. In embodiments, about 25 mg to about 100 mg of sitagliptin or a pharmaceutically acceptable salt thereof may be administered in 24 hours. In embodiments, about 25 mg to about 100 mg of sitagliptin or a pharmaceutically acceptable salt thereof may be administered in 24 hours. In embodiments, about 25 mg to about 200 mg of sitagliptin or a pharmaceutically acceptable salt thereof may be administered in 24 hours. In embodiments, about 25 mg to about 100 mg of sitagliptin or a pharmaceutically acceptable salt thereof may be administered in 24 hours. In embodiments, about 50 mg of sitagliptin or a pharmaceutically acceptable salt thereof may be administered in 24 hours. In embodiments, the sitagliptin or a pharmaceutically acceptable salt thereof may be administered in divided doses over 24 hours. In embodiments, sitagliptin may be administered once a day, e.g., with an evening meal.

In embodiments, pharmaceutical compositions include 10 mg to 15 mg, 15 mg to 20 mg, 20 mg to 25 mg, 25 mg to 30 mg, 30 mg to 35 mg, 35 mg to 40 mg, 40 mg to 45 mg, 45 mg to 50 mg, 50 mg to 55 mg, 55 mg to 60 mg, 60 mg to 75 mg, 75 mg, to 80 mg, 80 mg to 85 mg, 85 mg to 90 mg, 90 mg to 95 mg, 95 mg to 100 mg, 100 mg to 110 mg, 110 mg to 115 mg, 115 mg to 120 mg, 125 mg to 130 mg, 130 mg to 135 mg, 135 mg to 140 mg, 140 mg to 145 mg, 145 mg to 150 mg, 150 mg to 155 mg, 155 mg to 160 mg, 160 mg, to 165 mg, 165 mg to 170 mg, 175 mg to 180 mg, 180 mg to 185 mg, 185 mg to 190 mg, 190 mg to 195 mg, or 195 to 200 mg of sitagliptin or a pharmaceutically acceptable salt thereof. In embodiments, the compositions include 5 mg, 10 mg, 15 mg, 20 mg, 25 mg, 30 mg, 35 mg, 40 mg, 45 mg, 50 mg, 55 mg, 60 mg, 75 mg, 80 mg, 85 mg, 90 mg, 95 mg, 100 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, or 200 mg, sitagliptin or a pharmaceutically acceptable salt thereof.

In embodiments, methods of treating a metabolic disorder such as type 1 diabetes, type 2 diabetes or pre-diabetes herein include, in addition to gaboxadol or a pharmaceutically acceptable salt thereof, administering to a patient in need thereof about 10 mg to about 500 mg vildagliptin or a pharmaceutically acceptable salt thereof. In embodiments, methods of treating a metabolic disorder such as type 1 diabetes, type 2 diabetes or pre-diabetes herein include administering gaboxadol or a pharmaceutically acceptable salt thereof, in combination with vildagliptin or a pharmaceutically acceptable salt thereof. In embodiments, methods of treating a metabolic disorder such as type 1 diabetes, type 2 diabetes or pre-diabetes herein include administering a pharmaceutical composition including gaboxadol or a pharmaceutically acceptable salt thereof, in combination with vildagliptin or a pharmaceutically acceptable salt thereof.

In embodiments, about 10 mg to about 100 mg of vildagliptin or a pharmaceutically acceptable salt thereof may be administered in 24 hours. In embodiments, about 15 mg to about 100 mg of vildagliptin or a pharmaceutically acceptable salt thereof may be administered in 24 hours. In embodiments, about 20 mg to about 200 mg of vildagliptin or a pharmaceutically acceptable salt thereof may be administered in 24 hours. In embodiments, about 25 mg to about 100 mg of vildagliptin or a pharmaceutically acceptable salt thereof may be administered in 24 hours. In embodiments, about 25 mg to about 100 mg of vildagliptin or a pharmaceutically acceptable salt thereof may be administered in 24 hours. In embodiments, about 25 mg to about 100 mg of vildagliptin or a pharmaceutically acceptable salt thereof may be administered in 24 hours. In embodiments, about 25 mg to about 200 mg of vildagliptin or a pharmaceutically acceptable salt thereof may be administered in 24 hours. In embodiments, about 25 mg to about 100 mg of vildagliptin or a pharmaceutically acceptable salt thereof may be administered in 24 hours. In embodiments, about 50 mg of vildagliptin or a pharmaceutically acceptable salt thereof may be administered in 24 hours. In embodiments, the vildagliptin or a pharmaceutically acceptable salt thereof may be administered in divided doses over 24 hours. In embodiments, vildagliptin may be administered once a day, e.g., with a morning or evening meal. In embodiments, vildagliptin may be administered twice a day, e.g., with a morning and evening meal.

In embodiments, pharmaceutical compositions include 10 mg to 15 mg, 15 mg to 20 mg, 20 mg to 25 mg, 25 mg to 30 mg, 30 mg to 35 mg, 35 mg to 40 mg, 40 mg to 45 mg, 45 mg to 50 mg, 50 mg to 55 mg, 55 mg to 60 mg, 60 mg to 75 mg, 75 mg, to 80 mg, 80 mg to 85 mg, 85 mg to 90 mg, 90 mg to 95 mg, 95 mg to 100 mg, 100 mg to 110 mg, 110 mg to 115 mg, 115 mg to 120 mg, 125 mg to 130 mg, 130 mg to 135 mg, 135 mg to 140 mg, 140 mg to 145 mg, 145 mg to 150 mg, 150 mg to 155 mg, 155 mg to 160 mg, 160 mg, to 165 mg, 165 mg to 170 mg, 175 mg to 180 mg, 180 mg to 185 mg, 185 mg to 190 mg, 190 mg to 195 mg, or 195 to 200 mg of vildagliptin or a pharmaceutically acceptable salt thereof. In embodiments, the compositions include 5 mg, 10 mg, 15 mg, 20 mg, 25 mg, 30 mg, 35 mg, 40 mg, 45 mg, 50 mg, 55 mg, 60 mg, 75 mg, 80 mg, 85 mg, 90 mg, 95 mg, 100 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, or 200 mg, vildagliptin or a pharmaceutically acceptable salt thereof.

In embodiments, methods of treating a metabolic disorder such as type 1 diabetes, type 2 diabetes or pre-diabetes herein include, in addition to gaboxadol or a pharmaceutically acceptable salt thereof, administering to a patient in need thereof about 0.1 mg to about 10 mg saxagliptin or a pharmaceutically acceptable salt thereof. In embodiments, methods of treating a metabolic disorder such as type 1 diabetes, type 2 diabetes or pre-diabetes herein include administering gaboxadol or a pharmaceutically acceptable salt thereof, in combination with saxagliptin or a pharmaceutically acceptable salt thereof. In embodiments, methods of treating a metabolic disorder such as type 1 diabetes, type 2 diabetes or pre-diabetes herein include administering a pharmaceutical composition including gaboxadol or a pharmaceutically acceptable salt thereof, in combination with saxagliptin or a pharmaceutically acceptable salt thereof.

In embodiments, about 1 mg to about 7.5 mg of saxagliptin or a pharmaceutically acceptable salt thereof may be administered in 24 hours. In embodiments, about 1.5 mg to about 7 mg of saxagliptin or a pharmaceutically acceptable salt thereof may be administered in 24 hours. In embodiments, about 2 mg to about 6 mg of saxagliptin or a pharmaceutically acceptable salt thereof may be administered in 24 hours. In embodiments, about 2.5 mg to about 5.5 mg of saxagliptin or a pharmaceutically acceptable salt thereof may be administered in 24 hours. In embodiments, about 2.5 mg to about 5 mg of saxagliptin or a pharmaceutically acceptable salt thereof may be administered in 24 hours. In embodiments, about 1.75 mg to about 5 mg of saxagliptin or a pharmaceutically acceptable salt thereof may be administered in 24 hours. In embodiments, about 2.25 mg to about 5 mg of saxagliptin or a pharmaceutically acceptable salt thereof may be administered in 24 hours. In embodiments, about 2.75 mg to about 5 mg of saxagliptin or a pharmaceutically acceptable salt thereof may be administered in 24 hours. In embodiments, about 2.5 mg of saxagliptin or a pharmaceutically acceptable salt thereof may be administered in 24 hours. In embodiments, about 5 mg of saxagliptin or a pharmaceutically acceptable salt thereof may be administered in 24 hours. In embodiments, the saxagliptin or a pharmaceutically acceptable salt thereof may be administered in divided doses over 24 hours. In embodiments, saxagliptin may be administered once a day.

In embodiments, pharmaceutical compositions include 0.1 mg to 5 mg, 0.5 mg to 5 mg, 0.75 mg to 5 mg, 1.0 mg to 5 mg, 1.25 mg to 5 mg, 1.5 mg to 5 mg, 1.75 mg to 5 mg, 2.0 mg to 5 mg, 2.5 mg to 5 mg, 2.75 to 5 mg, 3 mg to 5 mg, 3.5 mg to 5 mg, 4 mg to 5 mg, 4.5 mg, to 5 mg, 0.1 mg to 2.5 mg, 0.5 mg to 2.5 mg, 0.75 mg to 2.5 mg, 1.0 mg to 2.5 mg, 1.25 mg to 2.5 mg, 1.5 mg to 2.5 mg, 1.75 mg to 2.5 mg, 2.0 mg to 2.5 mg of saxagliptin or a pharmaceutically acceptable salt thereof. In embodiments, the compositions include 0.1 mg, 0.5 mg, 0.75 mg, 1 mg, 1.25 mg, 1.5 mg, 1.75 mg, 2 mg, 2.25 mg, 2.5 mg, 2.75 mg, 3 mg, 3.25 mg, 3.5 mg, 3.75 mg, 4 mg, 4.25 mg, 4.5 mg, 4.75 mg, 5 mg, 7.5 mg, or 10 mg saxagliptin or a pharmaceutically acceptable salt thereof.

In embodiments, methods of treating a metabolic disorder such as type 1 diabetes, type 2 diabetes or pre-diabetes herein include, in addition to gaboxadol or a pharmaceutically acceptable salt thereof, administering to a patient in need thereof about 0.1 mg to about 10 mg linagliptin or a pharmaceutically acceptable salt thereof. In embodiments, methods of treating a metabolic disorder such as type 1 diabetes, type 2 diabetes or pre-diabetes herein include administering gaboxadol or a pharmaceutically acceptable salt thereof, in combination with linagliptin or a pharmaceutically acceptable salt thereof. In embodiments, methods of treating a metabolic disorder such as type 1 diabetes, type 2 diabetes or pre-diabetes herein include administering a pharmaceutical composition including gaboxadol or a pharmaceutically acceptable salt thereof, in combination with linagliptin or a pharmaceutically acceptable salt thereof.

In embodiments, about 1 mg to about 7.5 mg of linagliptin or a pharmaceutically acceptable salt thereof may be administered in 24 hours. In embodiments, about 1.5 mg to about 7 mg of linagliptin or a pharmaceutically acceptable salt thereof may be administered in 24 hours. In embodiments, about 2 mg to about 6 mg of linagliptin or a pharmaceutically acceptable salt thereof may be administered in 24 hours. In embodiments, about 2.5 mg to about 5.5 mg of linagliptin or a pharmaceutically acceptable salt thereof may be administered in 24 hours. In embodiments, about 2.5 mg to about 5 mg of linagliptin or a pharmaceutically acceptable salt thereof may be administered in 24 hours. In embodiments, about 1.75 mg to about 5 mg of linagliptin or a pharmaceutically acceptable salt thereof may be administered in 24 hours. In embodiments, about 2.25 mg to about 5 mg of linagliptin or a pharmaceutically acceptable salt thereof may be administered in 24 hours. In embodiments, about 2.75 mg to about 5 mg of linagliptin or a pharmaceutically acceptable salt thereof may be administered in 24 hours. In embodiments, about 2.5 mg of linagliptin or a pharmaceutically acceptable salt thereof may be administered in 24 hours. In embodiments, about 3 mg of linagliptin or a pharmaceutically acceptable salt thereof may be administered in 24 hours. In embodiments, about 4 mg of linagliptin or a pharmaceutically acceptable salt thereof may be administered in 24 hours. In embodiments, about 5 mg of linagliptin or a pharmaceutically acceptable salt thereof may be administered in 24 hours. In embodiments, about 6 mg of linagliptin or a pharmaceutically acceptable salt thereof may be administered in 24 hours. In embodiments, about 7 mg of linagliptin or a pharmaceutically acceptable salt thereof may be administered in 24 hours. In embodiments, about 8 mg of linagliptin or a pharmaceutically acceptable salt thereof may be administered in 24 hours. In embodiments, about 9 mg of linagliptin or a pharmaceutically acceptable salt thereof may be administered in 24 hours. In embodiments, about 10 mg of linagliptin or a pharmaceutically acceptable salt thereof may be administered in 24 hours. In embodiments, the linagliptin or a pharmaceutically acceptable salt thereof may be administered in divided doses over 24 hours. In embodiments, linagliptin may be administered once a day.

In embodiments, pharmaceutical compositions include 0.1 mg to 5 mg, 0.5 mg to 5 mg, 0.75 mg to 5 mg, 1.0 mg to 5 mg, 1.25 mg to 5 mg, 1.5 mg to 5 mg, 1.75 mg to 5 mg, 2.0 mg to 5 mg, 2.5 mg to 5 mg, 2.75 to 5 mg, 3 mg to 5 mg, 3.5 mg to 5 mg, 4 mg to 5 mg, 4.5 mg, to 5 mg, 0.1 mg to 2.5 mg, 0.5 mg to 2.5 mg, 0.75 mg to 2.5 mg, 1.0 mg to 2.5 mg, 1.25 mg to 2.5 mg, 1.5 mg to 2.5 mg, 1.75 mg to 2.5 mg, 2.0 mg to 2.5 mg of linagliptin or a pharmaceutically acceptable salt thereof. In embodiments, the compositions include 0.1 mg, 0.5 mg, 0.75 mg, 1 mg, 1.25 mg, 1.5 mg, 1.75 mg, 2 mg, 2.25 mg, 2.5 mg, 2.75 mg, 3 mg, 3.25 mg, 3.5 mg, 3.75 mg, 4 mg, 4.25 mg, 4.5 mg, 4.75 mg, 5 mg, 7.5 mg, or 10 mg linagliptin or a pharmaceutically acceptable salt thereof.

In embodiments, methods of treating a metabolic disorder such as type 1 diabetes, type 2 diabetes or pre-diabetes include, in addition to gaboxadol or a pharmaceutically acceptable salt thereof, administering to a patient in need thereof about 10 mg to about 300 mg gemigliptin or a pharmaceutically acceptable salt thereof. In embodiments, methods of treating a metabolic disorder such as type 1 diabetes, type 2 diabetes or pre-diabetes herein include administering gaboxadol or a pharmaceutically acceptable salt thereof, in combination with gemigliptin or a pharmaceutically acceptable salt thereof.

In embodiments, about 10 mg to about 300 mg of gemigliptin or a pharmaceutically acceptable salt thereof may be administered in 24 hours. In embodiments, about 10 mg to about 275 mg of gemigliptin or a pharmaceutically acceptable salt thereof may be administered in 24 hours. In embodiments, about 15 mg to about 250 mg of gemigliptin or a pharmaceutically acceptable salt thereof may be administered in 24 hours. In embodiments, about 20 mg to about 250 mg of gemigliptin or a pharmaceutically acceptable salt thereof may be administered in 24 hours. In embodiments, about 25 mg to about 250 mg of gemigliptin or a pharmaceutically acceptable salt thereof may be administered in 24 hours. In embodiments, about 30 mg to about 225 mg of gemigliptin or a pharmaceutically acceptable salt thereof may be administered in 24 hours. In embodiments, about 35 mg to about 200 mg of gemigliptin or a pharmaceutically acceptable salt thereof may be administered in 24 hours. In embodiments, about 40 mg to about 200 mg of gemigliptin or a pharmaceutically acceptable salt thereof may be administered in 24 hours. In embodiments, about 45 mg to about 200 mg of gemigliptin or a pharmaceutically acceptable salt thereof may be administered in 24 hours. In embodiments, about 50 mg to about 200 mg of gemigliptin or a pharmaceutically acceptable salt thereof may be administered in 24 hours. In embodiments, the gemigliptin or a pharmaceutically acceptable salt thereof may be administered in divided doses over 24 hours. In embodiments, gemigliptin may be administered once a day.

In embodiments, the patient is administered 10 mg to 15 mg, 15 mg to 20 mg, 20 mg to 25 mg, 25 mg to 30 mg, 30 mg to 35 mg, 35 mg to 40 mg, 40 mg to 45 mg, 45 mg to 50 mg, 50 mg to 55 mg, 55 mg to 60 mg, 60 mg to 75 mg, 75 mg, to 80 mg, 80 mg to 85 mg, 85 mg to 90 mg, 90 mg to 95 mg, 95 mg to 100 mg, 100 mg to 110 mg, 110 mg to 115 mg, 115 mg to 120 mg, 125 mg to 130 mg, 130 mg to 135 mg, 135 mg to 140 mg, 140 mg to 145 mg, 145 mg to 150 mg, 150 mg to 155 mg, 155 mg to 160 mg, 160 mg, to 165 mg, 165 mg to 170 mg, 175 mg to 180 mg, 180 mg to 185 mg, 185 mg to 190 mg, 190 mg to 195 mg, 195 to 200 mg, 200 mg to 225 mg, 225 mg to 250 mg, 250 mg to 275 mg, or 275 mg to 300 mg, gemigliptin or a pharmaceutically acceptable salt thereof.

In embodiments, the patient is administered 10 mg, 15 mg, 20 mg, 25 mg, 30 mg, 35 mg, 40 mg, 45 mg, 50 mg, 55 mg, 60 mg, 75 mg, 80 mg, 85 mg, 90 mg, 95 mg, 100 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 225 mg, 250 mg, 275 mg, or 300 mg, gemigliptin or a pharmaceutically acceptable salt thereof.

In embodiments methods of treating a metabolic disorder such as type 1 diabetes, type 2 diabetes or pre-diabetes include administering to a patient in need thereof a pharmaceutical composition including gaboxadol or a pharmaceutically acceptable salt thereof, in combination with about 10 mg to about 300 mg gemigliptin or a pharmaceutically acceptable salt thereof.

In embodiments, the compositions include 10 mg to 15 mg, 15 mg to 20 mg, 20 mg to 25 mg, 25 mg to 30 mg, 30 mg to 35 mg, 35 mg to 40 mg, 40 mg to 45 mg, 45 mg to 50 mg, 50 mg to 55 mg, 55 mg to 60 mg, 60 mg to 75 mg, 75 mg, to 80 mg, 80 mg to 85 mg, 85 mg to 90 mg, 90 mg to 95 mg, 95 mg to 100 mg, 100 mg to 110 mg, 110 mg to 115 mg, 115 mg to 120 mg, 125 mg to 130 mg, 130 mg to 135 mg, 135 mg to 140 mg, 140 mg to 145 mg, 145 mg to 150 mg, 150 mg to 155 mg, 155 mg to 160 mg, 160 mg, to 165 mg, 165 mg to 170 mg, 175 mg to 180 mg, 180 mg to 185 mg, 185 mg to 190 mg, 190 mg to 195 mg, 195 to 200 mg, 200 mg to 225 mg, 225 mg to 250 mg, 250 mg to 275 mg, or 275 mg to 300 mg, gemigliptin or a pharmaceutically acceptable salt thereof.

In embodiments, the compositions include 10 mg, 15 mg, 20 mg, 25 mg, 30 mg, 35 mg, 40 mg, 45 mg, 50 mg, 55 mg, 60 mg, 75 mg, 80 mg, 85 mg, 90 mg, 95 mg, 100 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 225 mg, 250 mg, 275 mg, or 300 mg, gemigliptin or a pharmaceutically acceptable salt thereof.

In embodiments, methods of treating a metabolic disorder such as type 1 diabetes, type 2 diabetes or pre-diabetes include in addition to gaboxadol or a pharmaceutically acceptable salt thereof, administering to a patient in need thereof about 10 mg to about 500 mg anagliptin or a pharmaceutically acceptable salt thereof. In embodiments, methods of treating a metabolic disorder such as type 1 diabetes, type 2 diabetes or pre-diabetes herein include administering gaboxadol or a pharmaceutically acceptable salt thereof, in combination with anagliptin or a pharmaceutically acceptable salt thereof.

In embodiments, about 10 mg to about 500 mg of anagliptin or a pharmaceutically acceptable salt thereof may be administered in 24 hours. In embodiments, about 50 mg to about 500 mg of anagliptin or a pharmaceutically acceptable salt thereof may be administered in 24 hours. In embodiments, about 75 mg to about 500 mg of anagliptin or a pharmaceutically acceptable salt thereof may be administered in 24 hours. In embodiments, about 100 mg to about 475 mg of anagliptin or a pharmaceutically acceptable salt thereof may be administered in 24 hours. In embodiments, about 125 mg to about 450 mg of anagliptin or a pharmaceutically acceptable salt thereof may be administered in 24 hours. In embodiments, about 150 mg to about 425 mg of anagliptin or a pharmaceutically acceptable salt thereof may be administered in 24 hours. In embodiments, about 200 mg to about 400 mg of anagliptin or a pharmaceutically acceptable salt thereof may be administered in 24 hours. In embodiments, about 200 mg of anagliptin or a pharmaceutically acceptable salt thereof may be administered in 24 hours. In embodiments, about 250 mg of anagliptin or a pharmaceutically acceptable salt thereof may be administered in 24 hours. In embodiments, about 300 mg of anagliptin or a pharmaceutically acceptable salt thereof may be administered in 24 hours. In embodiments, about 350 mg of anagliptin or a pharmaceutically acceptable salt thereof may be administered in 24 hours. In embodiments, about 375 mg of anagliptin or a pharmaceutically acceptable salt thereof may be administered in 24 hours. In embodiments, about 400 mg of anagliptin or a pharmaceutically acceptable salt thereof may be administered in 24 hours. In embodiments, the anagliptin or a pharmaceutically acceptable salt thereof may be administered in divided doses over 24 hours, e.g., 100 mg twice daily. In embodiments, anagliptin may be administered once a day.

In embodiments, the patient is administered 10 mg to 15 mg, 15 mg to 20 mg, 20 mg to 25 mg, 25 mg to 30 mg, 30 mg to 35 mg, 35 mg to 40 mg, 40 mg to 45 mg, 45 mg to 50 mg, 50 mg to 55 mg, 55 mg to 60 mg, 60 mg to 75 mg, 75 mg, to 80 mg, 80 mg to 85 mg, 85 mg to 90 mg, 90 mg to 95 mg, 95 mg to 100 mg, 100 mg to 110 mg, 110 mg to 115 mg, 115 mg to 120 mg, 125 mg to 130 mg, 130 mg to 135 mg, 135 mg to 140 mg, 140 mg to 145 mg, 145 mg to 150 mg, 150 mg to 155 mg, 155 mg to 160 mg, 160 mg, to 165 mg, 165 mg to 170 mg, 175 mg to 180 mg, 180 mg to 185 mg, 185 mg to 190 mg, 190 mg to 195 mg, 195 to 200 mg, 200 mg to 225 mg, 225 mg to 250 mg, 250 mg to 275 mg, 275 mg to 300 mg, 300 mg to 325 mg, 325 mg to 350 mg, 350 mg to 375 mg, 375 mg to 400 mg, 400 mg to 425 mg, 425 mg to 450 mg, 450 mg to 475 mg, or 475 mg to 500 mg, anagliptin or a pharmaceutically acceptable salt thereof.

In embodiments, the patient is administered 10 mg, 15 mg, 20 mg, 25 mg, 30 mg, 35 mg, 40 mg, 45 mg, 50 mg, 55 mg, 60 mg, 75 mg, 80 mg, 85 mg, 90 mg, 95 mg, 100 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 225 mg, 250 mg, 275 mg, 300 mg, 325 mg, 350 mg, 375 mg, 400 mg, 425 mg, 450 mg, 475 mg, or 500 mg, anagliptin or a pharmaceutically acceptable salt thereof.

In embodiments methods of treating a metabolic disorder such as type 1 diabetes, type 2 diabetes or pre-diabetes include administering to a patient in need thereof a pharmaceutical composition including gaboxadol or a pharmaceutically acceptable salt thereof, in combination with about 10 mg to about 500 mg anagliptin or a pharmaceutically acceptable salt thereof.

In embodiments, the compositions include 10 mg to 15 mg, 15 mg to 20 mg, 20 mg to 25 mg, 25 mg to 30 mg, 30 mg to 35 mg, 35 mg to 40 mg, 40 mg to 45 mg, 45 mg to 50 mg, 50 mg to 55 mg, 55 mg to 60 mg, 60 mg to 75 mg, 75 mg, to 80 mg, 80 mg to 85 mg, 85 mg to 90 mg, 90 mg to 95 mg, 95 mg to 100 mg, 100 mg to 110 mg, 110 mg to 115 mg, 115 mg to 120 mg, 125 mg to 130 mg, 130 mg to 135 mg, 135 mg to 140 mg, 140 mg to 145 mg, 145 mg to 150 mg, 150 mg to 155 mg, 155 mg to 160 mg, 160 mg, to 165 mg, 165 mg to 170 mg, 175 mg to 180 mg, 180 mg to 185 mg, 185 mg to 190 mg, 190 mg to 195 mg, 195 to 200 mg, 200 mg to 225 mg, 225 mg to 250 mg, 250 mg to 275 mg, 275 mg to 300 mg, 300 mg to 325 mg, 325 mg to 350 mg, 350 mg to 375 mg, 375 mg to 400 mg, 400 mg to 425 mg, 425 mg to 450 mg, 450 mg to 475 mg, or 475 mg to 500 mg, anagliptin or a pharmaceutically acceptable salt thereof.

In embodiments, the compositions include 10 mg, 15 mg, 20 mg, 25 mg, 30 mg, 35 mg, 40 mg, 45 mg, 50 mg, 55 mg, 60 mg, 75 mg, 80 mg, 85 mg, 90 mg, 95 mg, 100 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 225 mg, 250 mg, 275 mg, 300 mg, 325 mg, 350 mg, 375 mg, 400 mg, 425 mg, 450 mg, 475 mg, or 500 mg, anagliptin or a pharmaceutically acceptable salt thereof.

In embodiments, methods of treating a metabolic disorder such as type 1 diabetes, type 2 diabetes or pre-diabetes include, in addition to gaboxadol or a pharmaceutically acceptable salt thereof, administering to a patient in need thereof about 1 mg to about 100 mg teneligliptin or a pharmaceutically acceptable salt thereof. In embodiments, methods of treating a metabolic disorder such as type 1 diabetes, type 2 diabetes or pre-diabetes herein include administering gaboxadol or a pharmaceutically acceptable salt thereof, in combination with teneligliptin or a pharmaceutically acceptable salt thereof.

In embodiments, about 1 mg to about 100 mg of teneligliptin or a pharmaceutically acceptable salt thereof may be administered in 24 hours. In embodiments, about 5 mg to about 90 mg of teneligliptin or a pharmaceutically acceptable salt thereof may be administered in 24 hours. In embodiments, about 7.5 mg to about 85 mg of teneligliptin or a pharmaceutically acceptable salt thereof may be administered in 24 hours. In embodiments, about 10 mg to about 80 mg of teneligliptin or a pharmaceutically acceptable salt thereof may be administered in 24 hours. In embodiments, about 12.5 mg to about 75 mg of teneligliptin or a pharmaceutically acceptable salt thereof may be administered in 24 hours. In embodiments, about 15 mg to about 70 mg of teneligliptin or a pharmaceutically acceptable salt thereof may be administered in 24 hours. In embodiments, about 17.5 mg to about 65 mg of teneligliptin or a pharmaceutically acceptable salt thereof may be administered in 24 hours. In embodiments, about 20 mg to about 60 mg of teneligliptin or a pharmaceutically acceptable salt thereof may be administered in 24 hours. In embodiments, about 25 mg to about 55 mg of teneligliptin or a pharmaceutically acceptable salt thereof may be administered in 24 hours. In embodiments, about 30 mg to about 50 mg of teneligliptin or a pharmaceutically acceptable salt thereof may be administered in 24 hours. In embodiments, about 35 mg to about 45 mg of teneligliptin or a pharmaceutically acceptable salt thereof may be administered in 24 hours. In embodiments, about 20 mg of teneligliptin or a pharmaceutically acceptable salt thereof may be administered in 24 hours. In embodiments, about 40 mg of teneligliptin or a pharmaceutically acceptable salt thereof may be administered in 24 hours. In embodiments, the teneligliptin or a pharmaceutically acceptable salt thereof may be administered in divided doses over 24 hours. In embodiments, teneligliptin may be administered once a day.

In embodiments, the patient is administered 1.0 mg to 10 mg, 1.0 mg to 15 mg, 1.0 mg to 20 mg, 5 mg to 20 mg, 10 mg to 20 mg, 15 mg to 20 mg, 20 mg to 25 mg, 25 mg to 30 mg, 30 mg to 35 mg, 35 mg to 40 mg, 40 mg to 45 mg, 45 mg to 50 mg, 50 mg to 55 mg, 55 mg to 60 mg, 60 mg to 75 mg, 75 mg, to 80 mg, 80 mg to 85 mg, 85 mg to 90 mg, 90 mg to 95 mg, or 95 mg to 100 mg, teneligliptin or a pharmaceutically acceptable salt thereof.

In embodiments, the patient is administered 1 mg, 5 mg, 10 mg, 15 mg, 20 mg, 25 mg, 30 mg, 35 mg, 40 mg, 45 mg, 50 mg, 55 mg, 60 mg, 75 mg, 80 mg, 85 mg, 90 mg, 95 mg, or 100 mg, teneligliptin or a pharmaceutically acceptable salt thereof.

In embodiments methods of treating a metabolic disorder such as type 1 diabetes, type 2 diabetes or pre-diabetes include administering to a patient in need thereof a pharmaceutical composition including gaboxadol or a pharmaceutically acceptable salt thereof, in combination with about 1 mg to about 100 mg teneligliptin or a pharmaceutically acceptable salt thereof.

In embodiments, the compositions include 1 mg to 5 mg, 5 mg to 10 mg, 10 mg to 15 mg, 15 mg to 20 mg, 20 mg to 25 mg, 25 mg to 30 mg, 30 mg to 35 mg, 35 mg to 40 mg, 40 mg to 45 mg, 45 mg to 50 mg, 50 mg to 55 mg, 55 mg to 60 mg, 60 mg to 75 mg, 75 mg, to 80 mg, 80 mg to 85 mg, 85 mg to 90 mg, 90 mg to 95 mg, or 95 mg to 100 mg, teneligliptin or a pharmaceutically acceptable salt thereof.

In embodiments, the compositions include 1 mg, 5 mg, 10 mg, 15 mg, 20 mg, 25 mg, 30 mg, 35 mg, 40 mg, 45 mg, 50 mg, 55 mg, 60 mg, 75 mg, 80 mg, 85 mg, 90 mg, 95 mg, or 100 mg, teneligliptin or a pharmaceutically acceptable salt thereof.

In embodiments, methods of treating a metabolic disorder such as type 1 diabetes, type 2 diabetes or pre-diabetes include, in addition to gaboxadol or a pharmaceutically acceptable salt thereof, administering to a patient in need thereof about 1 mg to about 50 mg alogliptin or a pharmaceutically acceptable salt thereof. In embodiments, methods of treating a metabolic disorder such as type 1 diabetes, type 2 diabetes or pre-diabetes herein include administering gaboxadol or a pharmaceutically acceptable salt thereof, in combination with alogliptin or a pharmaceutically acceptable salt thereof.

In embodiments, about 1 mg to about 50 mg of alogliptin or a pharmaceutically acceptable salt thereof may be administered in 24 hours. In embodiments, about 2 mg to about 50 mg of alogliptin or a pharmaceutically acceptable salt thereof may be administered in 24 hours. In embodiments, about 3 mg to about 50 mg of alogliptin or a pharmaceutically acceptable salt thereof may be administered in 24 hours. In embodiments, about 4 mg to about 45 mg of alogliptin or a pharmaceutically acceptable salt thereof may be administered in 24 hours. In embodiments, about 5 mg to about 40 mg of alogliptin or a pharmaceutically acceptable salt thereof may be administered in 24 hours. In embodiments, about 6 mg to about 35 mg of alogliptin or a pharmaceutically acceptable salt thereof may be administered in 24 hours. In embodiments, about 6.25 mg to about 30 mg of alogliptin or a pharmaceutically acceptable salt thereof may be administered in 24 hours. In embodiments, about 7.0 mg to about 25 mg of alogliptin or a pharmaceutically acceptable salt thereof may be administered in 24 hours. In embodiments, about 8 mg to about 20 mg of alogliptin or a pharmaceutically acceptable salt thereof may be administered in 24 hours. In embodiments, about 10 mg to about 15 mg of alogliptin or a pharmaceutically acceptable salt thereof may be administered in 24 hours. In embodiments, about 12.5 mg to about 25 mg of alogliptin or a pharmaceutically acceptable salt thereof may be administered in 24 hours. In embodiments, about 6.25 mg of alogliptin or a pharmaceutically acceptable salt thereof may be administered in 24 hours. In embodiments, about 12.5 mg of alogliptin or a pharmaceutically acceptable salt thereof may be administered in 24 hours. In embodiments, about 25 mg of alogliptin or a pharmaceutically acceptable salt thereof may be administered in 24 hours. In embodiments, the alogliptin or a pharmaceutically acceptable salt thereof may be administered in divided doses over 24 hours. In embodiments, alogliptin may be administered once a day.

In embodiments, the patient is administered 1.0 mg to 10 mg, 1.0 mg to 15 mg, 1.0 mg to 25 mg, 5 mg to 10 mg, 5 mg to 25 mg, 6.25 mg to 12.5 mg, 6.25 mg to 25 mg, 12.5 mg to 25 mg, 15 mg to 25 mg, 20 mg to 25 mg, 25 mg to 30 mg, 30 mg to 35 mg, 35 mg to 40 mg, 40 mg to 45 mg, or 45 mg to 50 mg, alogliptin or a pharmaceutically acceptable salt thereof.

In embodiments, the patient is administered 1 mg, 5 mg, 6.25 mg, 10 mg, 12.5 mg, 15 mg, 20 mg, 25 mg, 30 mg, 35 mg, 40 mg, 45 mg, or 50 mg alogliptin or a pharmaceutically acceptable salt thereof.

In embodiments methods of treating a metabolic disorder such as type 1 diabetes, type 2 diabetes or pre-diabetes include administering to a patient in need thereof a pharmaceutical composition including gaboxadol or a pharmaceutically acceptable salt thereof, in combination with about 1 mg to about 50 mg alogliptin or a pharmaceutically acceptable salt thereof.

In embodiments, the compositions include 1.0 mg to 10 mg, 1.0 mg to 15 mg, 1.0 mg to 25 mg, 5 mg to 10 mg, 5 mg to 25 mg, 6.25 mg to 12.5 mg, 6.25 mg to 25 mg, 12.5 mg to 25 mg, 15 mg to 25 mg, 20 mg to 25 mg, 25 mg to 30 mg, 30 mg to 35 mg, 35 mg to 40 mg, 40 mg to 45 mg, or 45 mg to 50 mg, alogliptin or a pharmaceutically acceptable salt thereof.

In embodiments, the compositions include 1 mg, 5 mg, 6.25 mg, 10 mg, 12.5 mg, 15 mg, 20 mg, 25 mg, 30 mg, 35 mg, 40 mg, 45 mg, or 50 mg, alogliptin or a pharmaceutically acceptable salt thereof.

In embodiments, methods of treating a metabolic disorder such as type 1 diabetes, type 2 diabetes or pre-diabetes include, in addition to gaboxadol or a pharmaceutically acceptable salt thereof, administering to a patient in need thereof about 10 mg to about 200 mg trelagliptin or a pharmaceutically acceptable salt thereof. In embodiments, methods of treating a metabolic disorder such as type 1 diabetes, type 2 diabetes or pre-diabetes herein include administering gaboxadol or a pharmaceutically acceptable salt thereof, in combination with trelagliptin or a pharmaceutically acceptable salt thereof.

In embodiments, about 10 mg to about 200 mg of trelagliptin or a pharmaceutically acceptable salt thereof may be administered in 24 hours. In embodiments, about 15 mg to about 150 mg of trelagliptin or a pharmaceutically acceptable salt thereof may be administered in 24 hours. In embodiments, about 20 mg to about 200 mg of trelagliptin or a pharmaceutically acceptable salt thereof may be administered in 24 hours. In embodiments, about 25 mg to about 150 mg of trelagliptin or a pharmaceutically acceptable salt thereof may be administered in 24 hours. In embodiments, about 25 mg to about 150 mg of trelagliptin or a pharmaceutically acceptable salt thereof may be administered in 24 hours. In embodiments, about 25 mg to about 100 mg of trelagliptin or a pharmaceutically acceptable salt thereof may be administered in 24 hours. In embodiments, about 25 mg to about 200 mg of trelagliptin or a pharmaceutically acceptable salt thereof may be administered in 24 hours In embodiments, about 15 mg of trelagliptin or a pharmaceutically acceptable salt thereof may be administered in 24 hours. In embodiments, about 20 mg of trelagliptin or a pharmaceutically acceptable salt thereof may be administered in 24 hours. In embodiments, about 30 mg of trelagliptin or a pharmaceutically acceptable salt thereof may be administered in 24 hours. In embodiments, about 35 mg of trelagliptin or a pharmaceutically acceptable salt thereof may be administered in 24 hours. In embodiments, about 40 mg of trelagliptin or a pharmaceutically acceptable salt thereof may be administered in 24 hours. In embodiments, about 45 mg of trelagliptin or a pharmaceutically acceptable salt thereof may be administered in 24 hours. In embodiments, about 50 mg of trelagliptin or a pharmaceutically acceptable salt thereof may be administered in 24 hours. In embodiments, about 75 mg of trelagliptin or a pharmaceutically acceptable salt thereof may be administered in 24 hours. In embodiments, about 100 mg of trelagliptin or a pharmaceutically acceptable salt thereof may be administered in 24 hours. In embodiments, the trelagliptin or a pharmaceutically acceptable salt thereof may be administered once a week. In embodiments, trelagliptin may be administered once a week, e.g., with an evening meal.

In embodiments methods of treating a metabolic disorder such as type 1 diabetes, type 2 diabetes or pre-diabetes include administering to a patient in need thereof a pharmaceutical composition including gaboxadol or a pharmaceutically acceptable salt thereof, in combination with about 10 mg to about 200 mg trelagliptin or a pharmaceutically acceptable salt thereof.

In embodiments, the compositions include 10 mg to 15 mg, 15 mg to 20 mg, 20 mg to 25 mg, 25 mg to 30 mg, 30 mg to 35 mg, 35 mg to 40 mg, 40 mg to 45 mg, 45 mg to 50 mg, 50 mg to 55 mg, 55 mg to 60 mg, 60 mg to 75 mg, 75 mg, to 80 mg, 80 mg to 85 mg, 85 mg to 90 mg, 90 mg to 95 mg, 95 mg to 100 mg, 100 mg to 110 mg, 110 mg to 115 mg, 115 mg to 120 mg, 125 mg to 130 mg, 130 mg to 135 mg, 135 mg to 140 mg, 140 mg to 145 mg, 145 mg to 150 mg, 150 mg to 155 mg, 155 mg to 160 mg, 160 mg, to 165 mg, 165 mg to 170 mg, 175 mg to 180 mg, 180 mg to 185 mg, 185 mg to 190 mg, 190 mg to 195 mg, or 195 to 200 mg of trelagliptin or a pharmaceutically acceptable salt thereof. In embodiments, the compositions include 5 mg, 10 mg, 15 mg, 20 mg, 25 mg, 30 mg, 35 mg, 40 mg, 45 mg, 50 mg, 55 mg, 60 mg, 75 mg, 80 mg, 85 mg, 90 mg, 95 mg, 100 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, or 200 mg, trelagliptin or a pharmaceutically acceptable salt thereof.

In embodiments, methods of treating a metabolic disorder such as type 1 diabetes, type 2 diabetes or pre-diabetes include, in addition to gaboxadol or a pharmaceutically acceptable salt thereof, administering to a patient in need thereof about 10 mg to about 200 mg omarigliptin or a pharmaceutically acceptable salt thereof. In embodiments, methods of treating a metabolic disorder such as type 1 diabetes, type 2 diabetes or pre-diabetes herein include administering gaboxadol or a pharmaceutically acceptable salt thereof, in combination with omarigliptin or a pharmaceutically acceptable salt thereof.

In embodiments, about 10 mg to about 200 mg of omarigliptin or a pharmaceutically acceptable salt thereof may be administered in 24 hours. In embodiments, about 15 mg to about 150 mg of omarigliptin or a pharmaceutically acceptable salt thereof may be administered in 24 hours. In embodiments, about 20 mg to about 200 mg of omarigliptin or a pharmaceutically acceptable salt thereof may be administered in 24 hours. In embodiments, about 25 mg to about 150 mg of omarigliptin or a pharmaceutically acceptable salt thereof may be administered in 24 hours. In embodiments, about 25 mg to about 150 mg of omarigliptin or a pharmaceutically acceptable salt thereof may be administered in 24 hours. In embodiments, about 25 mg to about 100 mg of omarigliptin or a pharmaceutically acceptable salt thereof may be administered in 24 hours. In embodiments, about 25 mg to about 200 mg of omarigliptin or a pharmaceutically acceptable salt thereof may be administered in 24 hours In embodiments, about 15 mg of omarigliptin or a pharmaceutically acceptable salt thereof may be administered in 24 hours. In embodiments, about 20 mg of omarigliptin or a pharmaceutically acceptable salt thereof may be administered in 24 hours. In embodiments, about 30 mg of omarigliptin or a pharmaceutically acceptable salt thereof may be administered in 24 hours. In embodiments, about 35 mg of omarigliptin or a pharmaceutically acceptable salt thereof may be administered in 24 hours. In embodiments, about 40 mg of omarigliptin or a pharmaceutically acceptable salt thereof may be administered in 24 hours. In embodiments, about 45 mg of omarigliptin or a pharmaceutically acceptable salt thereof may be administered in 24 hours. In embodiments, about 50 mg of omarigliptin or a pharmaceutically acceptable salt thereof may be administered in 24 hours. In embodiments, about 75 mg of omarigliptin or a pharmaceutically acceptable salt thereof may be administered in 24 hours. In embodiments, about 100 mg of omarigliptin or a pharmaceutically acceptable salt thereof may be administered in 24 hours. In embodiments, the omarigliptin or a pharmaceutically acceptable salt thereof may be administered once a week. In embodiments, omarigliptin may be administered once a week, e.g., with an evening meal.

In embodiments methods of treating a metabolic disorder such as type 1 diabetes, type 2 diabetes or pre-diabetes include administering to a patient in need thereof a pharmaceutical composition including gaboxadol or a pharmaceutically acceptable salt thereof, in combination with about 10 mg to about 200 mg omarigliptin or a pharmaceutically acceptable salt thereof.

In embodiments, the compositions include 10 mg to 15 mg, 15 mg to 20 mg, 20 mg to 25 mg, 25 mg to 30 mg, 30 mg to 35 mg, 35 mg to 40 mg, 40 mg to 45 mg, 45 mg to 50 mg, 50 mg to 55 mg, 55 mg to 60 mg, 60 mg to 75 mg, 75 mg, to 80 mg, 80 mg to 85 mg, 85 mg to 90 mg, 90 mg to 95 mg, 95 mg to 100 mg, 100 mg to 110 mg, 110 mg to 115 mg, 115 mg to 120 mg, 125 mg to 130 mg, 130 mg to 135 mg, 135 mg to 140 mg, 140 mg to 145 mg, 145 mg to 150 mg, 150 mg to 155 mg, 155 mg to 160 mg, 160 mg, to 165 mg, 165 mg to 170 mg, 175 mg to 180 mg, 180 mg to 185 mg, 185 mg to 190 mg, 190 mg to 195 mg, or 195 to 200 mg of omarigliptin or a pharmaceutically acceptable salt thereof. In embodiments, the compositions include 5 mg, 10 mg, 15 mg, 20 mg, 25 mg, 30 mg, 35 mg, 40 mg, 45 mg, 50 mg, 55 mg, 60 mg, 75 mg, 80 mg, 85 mg, 90 mg, 95 mg, 100 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, or 200 mg, omarigliptin or a pharmaceutically acceptable salt thereof.

In embodiments, methods of treating a metabolic disorder such as type 1 diabetes, type 2 diabetes or pre-diabetes include, in addition to gaboxadol or a pharmaceutically acceptable salt thereof, administering to a patient in need thereof about 1 mg to about 50 mg evogliptin or a pharmaceutically acceptable salt thereof. In embodiments, methods of treating a metabolic disorder such as type 1 diabetes, type 2 diabetes or pre-diabetes herein include administering gaboxadol or a pharmaceutically acceptable salt thereof, in combination with evogliptin or a pharmaceutically acceptable salt thereof.

In embodiments, about 1 mg to about 50 mg of evogliptin or a pharmaceutically acceptable salt thereof may be administered in 24 hours. In embodiments, about 2 mg to about 50 mg of evogliptin or a pharmaceutically acceptable salt thereof may be administered in 24 hours. In embodiments, about 3 mg to about 50 mg of evogliptin or a pharmaceutically acceptable salt thereof may be administered in 24 hours. In embodiments, about 4 mg to about 45 mg of evogliptin or a pharmaceutically acceptable salt thereof may be administered in 24 hours. In embodiments, about 5 mg to about 40 mg of evogliptin or a pharmaceutically acceptable salt thereof may be administered in 24 hours. In embodiments, about 6 mg to about 35 mg of evogliptin or a pharmaceutically acceptable salt thereof may be administered in 24 hours. In embodiments, about 7.0 mg to about 25 mg of evogliptin or a pharmaceutically acceptable salt thereof may be administered in 24 hours. In embodiments, about 8 mg to about 20 mg of evogliptin or a pharmaceutically acceptable salt thereof may be administered in 24 hours. In embodiments, about 10 mg to about 15 mg of evogliptin or a pharmaceutically acceptable salt thereof may be administered in 24 hours. In embodiments, about 15 mg to about 20 mg of evogliptin or a pharmaceutically acceptable salt thereof may be administered in 24 hours. In embodiments, about 5 mg of evogliptin or a pharmaceutically acceptable salt thereof may be administered in 24 hours. In embodiments, about 10 mg of evogliptin or a pharmaceutically acceptable salt thereof may be administered in 24 hours. In embodiments, about 15 mg of evogliptin or a pharmaceutically acceptable salt thereof may be administered in 24 hours. In embodiments, about 20 mg of evogliptin or a pharmaceutically acceptable salt thereof may be administered in 24 hours. In embodiments, about 25 mg of evogliptin or a pharmaceutically acceptable salt thereof may be administered in 24 hours. In embodiments, the evogliptin or a pharmaceutically acceptable salt thereof may be administered in divided doses over 24 hours. In embodiments, evogliptin may be administered once a day.

In embodiments, the patient is administered 1.0 mg to 10 mg, 1.0 mg to 15 mg, 1.0 mg to 20 mg, 1.0 mg to 25 mg, 5 mg to 10 mg, 5 mg to 25 mg, 5 mg to 20 mg, 10 mg to 15 mg, 10 mg to 20 mg, 10 mg to 25 mg, 15 mg to 20 mg, 15 mg to 25 mg, 20 mg to 25 mg, 25 mg to 30 mg, 30 mg to 35 mg, 35 mg to 40 mg, 40 mg to 45 mg, or 45 mg to 50 mg, evogliptin or a pharmaceutically acceptable salt thereof.

In embodiments, the patient is administered 1 mg, 5 mg, 10 mg, 12 mg, 15 mg, 20 mg, 25 mg, 30 mg, 35 mg, 40 mg, 45 mg, or 50 mg evogliptin or a pharmaceutically acceptable salt thereof.

In embodiments methods of treating a metabolic disorder such as type 1 diabetes, type 2 diabetes or pre-diabetes include administering to a patient in need thereof a pharmaceutical composition including gaboxadol or a pharmaceutically acceptable salt thereof, in combination with about 1 mg to about 50 mg evogliptin or a pharmaceutically acceptable salt thereof.

In embodiments, the compositions include 1.0 mg to 10 mg, 1.0 mg to 15 mg, 1.0 mg to 25 mg, 1 mg to 30 mg, 5 mg to 10 mg, 5 mg to 20 mg, 5 mg to 25 mg, 10 mg to 15 mg, 15 mg to 20 mg, 20 mg to 25 mg, 25 mg to 30 mg, 30 mg to 35 mg, 35 mg to 40 mg, 40 mg to 45 mg, or 45 mg to 50 mg, evogliptin or a pharmaceutically acceptable salt thereof.

In embodiments, the compositions include 1 mg, 5 mg, 10 mg, 15 mg, 20 mg, 25 mg, 30 mg, 35 mg, 40 mg, 45 mg, or 50 mg, evogliptin or a pharmaceutically acceptable salt thereof.

In embodiments, methods of treating a metabolic disorder such as type 1 diabetes, type 2 diabetes or pre-diabetes include in addition to gaboxadol or a pharmaceutically acceptable salt thereof, administering to a patient in need thereof in combination with about 10 mg to about 500 mg dutogliptin or a pharmaceutically acceptable salt thereof. In embodiments, methods of treating a metabolic disorder such as type 1 diabetes, type 2 diabetes or pre-diabetes herein include administering gaboxadol or a pharmaceutically acceptable salt thereof, in combination with dutogliptin or a pharmaceutically acceptable salt thereof.

In embodiments, about 10 mg to about 500 mg of dutogliptin or a pharmaceutically acceptable salt thereof may be administered in 24 hours. In embodiments, about 50 mg to about 500 mg of dutogliptin or a pharmaceutically acceptable salt thereof may be administered in 24 hours. In embodiments, about 75 mg to about 500 mg of dutogliptin or a pharmaceutically acceptable salt thereof may be administered in 24 hours. In embodiments, about 100 mg to about 475 mg of dutogliptin or a pharmaceutically acceptable salt thereof may be administered in 24 hours. In embodiments, about 125 mg to about 450 mg of dutogliptin or a pharmaceutically acceptable salt thereof may be administered in 24 hours. In embodiments, about 150 mg to about 425 mg of dutogliptin or a pharmaceutically acceptable salt thereof may be administered in 24 hours. In embodiments, about 200 mg to about 400 mg of dutogliptin or a pharmaceutically acceptable salt thereof may be administered in 24 hours. In embodiments, about 200 mg of dutogliptin or a pharmaceutically acceptable salt thereof may be administered in 24 hours. In embodiments, about 250 mg of dutogliptin or a pharmaceutically acceptable salt thereof may be administered in 24 hours. In embodiments, about 300 mg of dutogliptin or a pharmaceutically acceptable salt thereof may be administered in 24 hours. In embodiments, about 350 mg of dutogliptin or a pharmaceutically acceptable salt thereof may be administered in 24 hours. In embodiments, about 375 mg of dutogliptin or a pharmaceutically acceptable salt thereof may be administered in 24 hours. In embodiments, about 100 mg of dutogliptin or a pharmaceutically acceptable salt thereof may be administered in 24 hours. In embodiments, about 200 mg of dutogliptin or a pharmaceutically acceptable salt thereof may be administered in 24 hours. In embodiments, about 300 mg of dutogliptin or a pharmaceutically acceptable salt thereof may be administered in 24 hours. In embodiments, about 400 mg of dutogliptin or a pharmaceutically acceptable salt thereof may be administered in 24 hours. In embodiments, the dutogliptin or a pharmaceutically acceptable salt thereof may be administered in divided doses over 24 hours, e.g., 100 mg twice daily. In embodiments, dutogliptin may be administered once a day, e.g. 400 mg.

In embodiments, the patient is administered 10 mg to 15 mg, 15 mg to 20 mg, 20 mg to 25 mg, 25 mg to 30 mg, 30 mg to 35 mg, 35 mg to 40 mg, 40 mg to 45 mg, 45 mg to 50 mg, 50 mg to 55 mg, 55 mg to 60 mg, 60 mg to 75 mg, 75 mg to 80 mg, 80 mg to 85 mg, 85 mg to 90 mg, 90 mg to 95 mg, 95 mg to 100 mg, 100 mg to 110 mg, 110 mg to 115 mg, 115 mg to 120 mg, 125 mg to 130 mg, 130 mg to 135 mg, 135 mg to 140 mg, 140 mg to 145 mg, 145 mg to 150 mg, 150 mg to 155 mg, 155 mg to 160 mg, 160 mg to 165 mg, 165 mg to 170 mg, 170 mg to 175 mg, 175 mg to 180 mg, 180 mg to 185 mg, 185 mg to 190 mg, 190 mg to 195 mg, 195 to 200 mg, 200 mg to 225 mg, 225 mg to 250 mg, 250 mg to 275 mg, 275 mg to 300 mg, 300 mg to 325 mg, 325 mg to 350 mg, 350 mg to 375 mg, 375 mg to 400 mg, 400 mg to 425 mg, 425 mg to 450 mg, 450 mg to 475 mg, or 475 mg to 500 mg, dutogliptin or a pharmaceutically acceptable salt thereof.

In embodiments, the patient is administered 10 mg, 15 mg, 20 mg, 25 mg, 30 mg, 35 mg, 40 mg, 45 mg, 50 mg, 55 mg, 60 mg, 75 mg, 80 mg, 85 mg, 90 mg, 95 mg, 100 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 225 mg, 250 mg, 275 mg, 300 mg, 325 mg, 350 mg, 375 mg, 400 mg, 425 mg, 450 mg, 475 mg, or 500 mg, dutogliptin or a pharmaceutically acceptable salt thereof.

In embodiments methods of treating a metabolic disorder such as type 1 diabetes, type 2 diabetes or pre-diabetes include administering to a patient in need thereof a pharmaceutical composition including gaboxadol or a pharmaceutically acceptable salt thereof, in combination with about 10 mg to about 500 mg dutogliptin or a pharmaceutically acceptable salt thereof.

In embodiments, the compositions include 10 mg to 15 mg, 15 mg to 20 mg, 20 mg to 25 mg, 25 mg to 30 mg, 30 mg to 35 mg, 35 mg to 40 mg, 40 mg to 45 mg, 45 mg to 50 mg, 50 mg to 55 mg, 55 mg to 60 mg, 60 mg to 75 mg, 75 mg to 80 mg, 80 mg to 85 mg, 85 mg to 90 mg, 90 mg to 95 mg, 95 mg to 100 mg, 100 mg to 110 mg, 110 mg to 115 mg, 115 mg to 120 mg, 125 mg to 130 mg, 130 mg to 135 mg, 135 mg to 140 mg, 140 mg to 145 mg, 145 mg to 150 mg, 150 mg to 155 mg, 155 mg to 160 mg, 160 mg to 165 mg, 165 mg to 170 mg, 170 mg to 180 mg, 175 mg to 180 mg, 180 mg to 185 mg, 185 mg to 190 mg, 190 mg to 195 mg, 195 to 200 mg, 200 mg to 225 mg, 225 mg to 250 mg, 250 mg to 275 mg, 275 mg to 300 mg, 300 mg to 325 mg, 325 mg to 350 mg, 350 mg to 375 mg, 375 mg to 400 mg, 400 mg to 425 mg, 425 mg to 450 mg, 450 mg to 475 mg, or 475 mg to 500 mg, dutogliptin or a pharmaceutically acceptable salt thereof.

In embodiments, the compositions include 10 mg, 15 mg, 20 mg, 25 mg, 30 mg, 35 mg, 40 mg, 45 mg, 50 mg, 55 mg, 60 mg, 75 mg, 80 mg, 85 mg, 90 mg, 95 mg, 100 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 225 mg, 250 mg, 275 mg, 300 mg, 325 mg, 350 mg, 375 mg, 400 mg, 425 mg, 450 mg, 475 mg, or 500 mg, dutogliptin or a pharmaceutically acceptable salt thereof.

In embodiments, methods of treating a metabolic disorder such as type 1 diabetes, type 2 diabetes or pre-diabetes herein include, in addition to gaboxadol or a pharmaceutically acceptable salt thereof, administering to a patient in need thereof about 50 mg to about 3000 mg berberine or a pharmaceutically acceptable salt thereof. In embodiments, methods of treating a metabolic disorder such as type 1 diabetes, type 2 diabetes or pre-diabetes herein include administering gaboxadol or a pharmaceutically acceptable salt thereof, in combination with berberine or a pharmaceutically acceptable salt thereof.

In embodiments, about 50 mg to about 3000 mg of berberine or a pharmaceutically acceptable salt thereof may be administered in 24 hours. In embodiments, the berberine or a pharmaceutically acceptable salt thereof may be administered in divided doses over 24 hours. In embodiments, berberine may be administered once a day, e.g., with an evening meal. In embodiments, berberine may be administered three times daily, e.g., with meals. In embodiments, berberine can be given in doses varying from about 500 mg to 2000 mg up to 2500 mg or 3000 mg per day using various dosing regimens from about 100 mg to 500 mg or 200 mg to 850 mg (1-3 times a day), or about 300 mg to 1000 mg once or twice a day.

In embodiments, the patient is administered 50 mg to 75 mg, 75 mg to 100 mg, 100 mg to 125 mg, 125 mg to 150 mg, 150 mg to 175 mg, 175 mg to 200 mg, 200 mg to 225 mg, 225 mg to 250 mg, 250 mg to 275 mg, 275 mg to 300 mg, 300 mg, to 325 mg, 325 mg to 350 mg, 350 mg to 375 mg, 375 mg to 400 mg, 400 mg to 425 mg, 425 mg to 450 mg, 450 mg to 475 mg, 475 mg to 500 mg, 500 mg to 525 mg, 525 mg to 550 mg, 550 mg to 575 mg, 575 mg to 600 mg, 600 mg to 625 mg, 625 mg to 650 mg, 650 mg to 675 mg, 675 mg to 700 mg, 700 mg to 725 mg, 725 mg to 750 mg, 750 mg to 775 mg, 775 mg to 800 mg, 800 mg to 825 mg, 825 mg to 850 mg, 850 mg to 875 mg, 875 mg to 900 mg, 900 mg to 925 mg, 925 mg to 950 mg, 950 mg to 975 mg, 975 mg to 1000 mg, 1000 mg to 1025 mg, 1025 mg to 1050 mg, 1050 mg to 1075 mg, 1075 mg to 1100 mg, 1100 mg to 1125 mg, 1125 mg to 1150 mg, 1150 mg to 1175 mg, 1175 mg to 1200 mg, 1200 mg to 1225 mg, 1225 mg to 1250 mg, 1250 mg to 1275 mg, 1275 mg to 1300 mg, 1300 mg to 1325 mg, 1325 mg to 1350 mg, 1350 mg to 1375 mg, 1375 mg to 1400 mg, 1400 mg to 1425 mg, 1425 mg to 1450 mg, 1450 mg to 1475 mg, 1475 mg to 1500 mg, 1500 mg to 1525 mg, 1525 mg to 1550 mg, 1550 mg to 1575 mg, 1575 mg to 1600 mg, 1600 mg to 1625 mg, 1625 mg to 1650 mg, 1650 mg to 1675 mg, 1675 mg to 1700 mg, 1700 mg to 1725 mg, 1725 mg to 1750 mg, 1750 mg to 1775 mg, 1775 mg to 1800 mg, 1800 mg to 1825 mg, 1825 mg to 1850 mg, 1850 mg to 1875 mg, 1875 mg to 1900 mg, 1900 mg to 1925 mg, 1925 mg to 1950 mg, 1950 mg to 1975 mg, 1975 mg to 2000 mg, 2000 mg to 2025 mg, 2025 mg to 2050 mg, 2050 mg to 2075 mg, 2075 mg to 2100 mg, 2100 mg to 2125 mg, 2125 mg to 2150 mg, 2150 mg to 2175 mg, 2175 mg to 2200 mg, 2200 mg to 2225 mg, 2225 mg to 2250 mg, 2250 mg to 2275 mg, 2275 mg to 2300 mg, 2300 mg to 2325 mg, 2325 mg to 2350 mg, 2350 mg to 2375 mg, 2375 mg to 2400 mg, 2400 mg to 2425 mg, 2425 mg to 2450 mg, 2450 mg to 2475 mg, 2475 mg to 2500 mg, 2500 mg to 2525 mg, 2525 mg to 2550 mg, 2550 mg to 2575 mg, 2575 mg to 2600 mg, 2600 mg to 2625 mg, 2625 mg to 2650 mg, 2650 mg to 2675 mg, 2675 mg to 2700 mg, 2700 mg to 2725 mg, 2725 mg to 2750 mg, 2750 mg to 2775 mg, 2775 mg to 2800 mg, 2800 mg to 2825 mg, 2825 mg to 2850 mg, 2850 mg to 2875 mg, 2875 mg to 2900 mg, 2900 mg to 2925 mg, 2925 mg to 2950 mg, 2950 mg to 2975 mg, or 2975 mg to 3000 mg, berberine or a pharmaceutically acceptable salt thereof.

In embodiments, the patient is administered 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1225 mg, 1250 mg, 1275 mg, 1300 mg, 1325 mg, 1350 mg, 1375 mg, 1400 mg, 1425 mg, 1450 mg, 1475 mg, 1500 mg, 1525 mg, 1550 mg, 1575 mg, 1600 mg, 1625 mg, 1650 mg, 1675 mg, 1700 mg, 1725 mg, 1750 mg, 1775 mg, 1800 mg, 1825 mg, 1850 mg, 1875 mg, 1900 mg, 1925 mg, 1950 mg, 1975 mg, 2000 mg, 2025 mg, 2250 mg, 2275 mg, 2300 mg, 2325 mg, 2350 mg, 2375 mg, 2400 mg, 2425 mg, 2450 mg, 2475 mg, 2500 mg, 2525 mg, 2550 mg, 2575 mg, 2600 mg, 2625 mg, 2650 mg, 2675 mg, 2700 mg, 2725 mg, 2750 mg, 2775 mg, 2800 mg, 2825 mg, 2850 mg, 2875 mg, 2900 mg, 2925 mg, 2950 mg, 2975 mg, or 3000 mg, berberine or a pharmaceutically acceptable salt thereof.

In embodiments methods of treating a metabolic disorder such as type 1 diabetes, type 2 diabetes or pre-diabetes include administering to a patient in need thereof a pharmaceutical composition including gaboxadol or a pharmaceutically acceptable salt thereof in combination with about 50 mg to about 3000 mg berberine or a pharmaceutically acceptable salt thereof.

In embodiments, the pharmaceutical compositions herein include 50 mg to 75 mg, 75 mg to 100 mg, 100 mg to 125 mg, 125 mg to 150 mg, 150 mg to 175 mg, 175 mg to 200 mg, 200 mg to 225 mg, 225 mg to 250 mg, 250 mg to 275 mg, 275 mg to 300 mg, 300 mg to 325 mg, 325 mg to 350 mg, 350 mg to 375 mg, 375 mg to 400 mg, 400 mg to 425 mg, 425 mg to 450 mg, 450 mg to 475 mg, 475 mg to 500 mg, 500 mg to 525 mg, 525 mg to 550 mg, 550 mg to 575 mg, 575 mg to 600 mg, 600 mg to 625 mg, 625 mg to 650 mg, 650 mg to 675 mg, 675 mg to 700 mg, 700 mg to 725 mg, 725 mg to 750 mg, 750 mg to 775 mg, 775 mg to 800 mg, 800 mg to 825 mg, 825 mg to 850 mg, 850 mg to 875 mg, 875 mg to 900 mg, 900 mg to 925 mg, 925 mg to 950 mg, 950 mg to 975 mg, 975 mg to 1000 mg, 1000 mg to 1025 mg, 1025 mg to 1050 mg, 1050 mg to 1075 mg, 1075 mg to 1100 mg, 1100 mg to 1125 mg, 1125 mg to 1150 mg, 1150 mg to 1175 mg, 1175 mg to 1200 mg, 1200 mg to 1225 mg, 1225 mg to 1250 mg, 1250 mg to 1275 mg, 1275 mg to 1300 mg, 1300 mg to 1325 mg, 1325 mg to 1350 mg, 1350 mg to 1375 mg, 1375 mg to 1400 mg, 1400 mg to 1425 mg, 1425 mg to 1450 mg, 1450 mg to 1475 mg, 1475 mg to 1500 mg, 1500 mg to 1525 mg, 1525 mg to 1550 mg, 1550 mg to 1575 mg, 1575 mg to 1600 mg, 1600 mg to 1625 mg, 1625 mg to 1650 mg, 1650 mg to 1675 mg, 1675 mg to 1700 mg, 1700 mg to 1725 mg, 1725 mg to 1750 mg, 1750 mg to 1775 mg, 1775 mg to 1800 mg, 1800 mg to 1825 mg, 1825 mg to 1850 mg, 1850 mg to 1875 mg, 1875 mg to 1900 mg, 1900 mg to 1925 mg, 1925 mg to 1950 mg, 1950 mg to 1975 mg, 1975 mg to 2000 mg, 2000 mg to 2025 mg, 2025 mg to 2050 mg, 2050 mg to 2075 mg, 2075 mg to 2100 mg, 2100 mg to 2125 mg, 2125 mg to 2150 mg, 2150 mg to 2175 mg, 2175 mg to 2200 mg, 2200 mg to 2225 mg, 2225 mg to 2250 mg, 2250 mg to 2275 mg, 2275 mg to 2300 mg, 2300 mg to 2325 mg, 2325 mg to 2350 mg, 2350 mg to 2375 mg, 2375 mg to 2400 mg, 2400 mg to 2425 mg, 2425 mg to 2450 mg, 2450 mg to 2475 mg, 2475 mg to 2500 mg, 2500 mg to 2525 mg, 2525 mg to 2550 mg, 2550 mg to 2575 mg, 2575 mg to 2600 mg, 2600 mg to 2625 mg, 2625 mg to 2650 mg, 2650 mg to 2675 mg, 2675 mg to 2700 mg, 2700 mg to 2725 mg, 2725 mg to 2750 mg, 2750 mg to 2775 mg, 2775 mg to 2800 mg, 2800 mg to 2825 mg, 2825 mg to 2850 mg, 2850 mg to 2875 mg, 2875 mg to 2900 mg, 2900 mg to 2925 mg, 2925 mg to 2950 mg, 2950 mg to 2975 mg, 2975 mg to 3000 mg, berberine or a pharmaceutically acceptable salt thereof.

In embodiments, the pharmaceutical compositions include 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1225 mg, 1250 mg, 1275 mg, 1300 mg, 1325 mg, 1350 mg, 1375 mg, 1400 mg, 1425 mg, 1450 mg, 1475 mg, 1500 mg, 1525 mg, 1550 mg, 1575 mg, 1600 mg, 1625 mg, 1650 mg, 1675 mg, 1700 mg, 1725 mg, 1750 mg, 1775 mg, 1800 mg, 1825 mg, 1850 mg, 1875 mg, 1900 mg, 1925 mg, 1950 mg, 1975 mg, 2000 mg, 2025 mg, 2250 mg, 2275 mg, 2300 mg, 2325 mg, 2350 mg, 2375 mg, 2400 mg, 2425 mg, 2450 mg, 2475 mg, 2500 mg, 2525 mg, 2550 mg, 2575 mg, 2600 mg, 2625 mg, 2650 mg, 2675 mg, 2700 mg, 2725 mg, 2750 mg, 2775 mg, 2800 mg, 2825 mg, 2850 mg, 2875 mg, 2900 mg, 2925 mg, 2950 mg, 2975 mg, 3000 mg, berberine or a pharmaceutically acceptable salt thereof.

In embodiments, a patient in need thereof is administered gaboxadol or a pharmaceutically acceptable salt thereof in combination with a glucagon-like peptide-1 (GLP-1) receptor agonist or a pharmaceutically acceptable salt thereof. In embodiments a patient in need thereof is administered a pharmaceutical composition including gaboxadol or a pharmaceutically acceptable salt thereof in combination with a GLP-1 receptor agonist or a pharmaceutically acceptable salt thereof. Examples of GLP-1 receptor agonists include GLP-1, exenatide, liraglutide, lixisenatide, albiglutide, dulaglutide, taspoglutide and semaglutide.

In embodiments, methods of treating a metabolic disorder such as type 1 diabetes, type 2 diabetes or pre-diabetes herein include, in addition to gaboxadol or a pharmaceutically acceptable salt thereof, administering to a patient in need thereof about 0.1 mg to about 10 mg exenatide or a pharmaceutically acceptable salt thereof in a sustained release injectable dosage form. In embodiments, methods of treating a metabolic disorder such as type 1 diabetes, type 2 diabetes or pre-diabetes herein include administering gaboxadol or a pharmaceutically acceptable salt thereof, in combination with exenatide or a pharmaceutically acceptable salt thereof.

In embodiments, exenatide or a pharmaceutically acceptable salt thereof is administered in an amount between 5 micrograms and 10 micrograms twice daily as an injectable dosage form. In embodiments, about 5 mcg to about 20 mcg of exenatide or a pharmaceutically acceptable salt thereof may be administered in 24 hours. In embodiments, about 0.5 mg to about 5 mg of sustained release exenatide or a pharmaceutically acceptable salt thereof may be administered once weekly. In embodiments, about 1.0 mg to about 5 mg of sustained release exenatide or a pharmaceutically acceptable salt thereof may be administered once weekly. In embodiments, about 1.25 mg to about 5 mg of sustained release exenatide or a pharmaceutically acceptable salt thereof may be administered once weekly. In embodiments, about 1.5 mg to about 5.5 mg of sustained release exenatide or a pharmaceutically acceptable salt thereof may be administered once weekly. In embodiments, about 2 mg to about 3 mg of sustained release exenatide or a pharmaceutically acceptable salt thereof may be administered once weekly. In embodiments, about 2.25 mg to about 4 mg of sustained release exenatide or a pharmaceutically acceptable salt thereof may be administered once weekly. In embodiments, about 2.75 mg to about 3 mg of sustained release exenatide or a pharmaceutically acceptable salt thereof may be administered once weekly. In embodiments, about 5 mcg of exenatide or a pharmaceutically acceptable salt thereof may be administered in 24 hours. In embodiments, about 10 mcg of exenatide or a pharmaceutically acceptable salt thereof may be administered in 24 hours. In embodiments, about 15 mcg of exenatide or a pharmaceutically acceptable salt thereof may be administered in 24 hours. In embodiments, about 20 mcg of exenatide or a pharmaceutically acceptable salt thereof may be administered in 24 hours. In embodiments, about 1 mg of sustained release exenatide or a pharmaceutically acceptable salt thereof may be administered once weekly. In embodiments, about 1.5 mg of sustained release exenatide or a pharmaceutically acceptable salt thereof may be administered once weekly. In embodiments, about 2 mg of sustained release exenatide or a pharmaceutically acceptable salt thereof may be administered once weekly. In embodiments, about 2.25 mg of sustained release exenatide or a pharmaceutically acceptable salt thereof may be administered once weekly. In embodiments, about 2.5 mg of sustained release exenatide or a pharmaceutically acceptable salt thereof may be administered once weekly. In embodiments, about 3 mg of sustained release exenatide or a pharmaceutically acceptable salt thereof may be administered once weekly. In embodiments, sustained release exenatide or a pharmaceutically acceptable salt thereof may be administered once weekly. In embodiments, exenatide may be administered once or twice a day. In embodiments, exenatide may be administered parenterally. In embodiments, exenatide may be administered subcutaneously.

In embodiments methods of treating a metabolic disorder such as type 1 diabetes, type 2 diabetes or pre-diabetes include administering to a patient in need thereof a pharmaceutical composition including gaboxadol or a pharmaceutically acceptable salt thereof in combination with about 0.1 mg to about 10 mg exenatide or a pharmaceutically acceptable salt thereof.

In embodiments, the compositions include 0.1 mcg to 5 mcg, 0.5 mcg to 5 mcg, 0.75 mcg to 5 mcg, 1.0 mcg to 5 mcg, 1.25 mcg to 5 mcg, 1.5 mcg to 5 mcg, 1.75 mcg to 5 mcg, 2.0 mcg to 5 mcg, 2.5 mcg to 5 mcg, 2.75 mcg to 5 mcg, 3 mcg to 5 mcg, 5 mcg to 10 mcg, 10 mcg to 15 mcg, 1 mg to 5 mg, 1.5 mg to 5 mg, 2 mg to 2.5 mg, 2.5 mg to 3 mg, 0.75 mg to 2.5 mg, 1.0 mg to 2.5 mg, 1.25 mg to 2.5 mg, 1.5 mg to 2.5 mg, 1.75 mg to 2.5 mg, 2.0 mg to 2.5 mg of exenatide or a pharmaceutically acceptable salt thereof. In embodiments, the compositions include 2.5 mcg, 5 mcg, 7.5 mcg, 10 mcg, 20 mcg, 0.1 mg, 0.5 mg, 0.75 mg, 1 mg, 1.25 mg, 1.5 mg, 1.75 mg, 2 mg, 2.25 mg, 2.5 mg, 2.75 mg, 3 mg, 3.25 mg, 3.5 mg, 3.75 mg, 4 mg, 4.25 mg, 4.5 mg, 4.75 mg, 5 mg, 7.5 mg, or 10 mg exenatide or a pharmaceutically acceptable salt thereof. Microgram amounts of exenatide refer to instant release formulations. Milligram amounts of exenatide refer to sustained release formulations.

In embodiments, methods of treating a metabolic disorder such as type 1 diabetes, type 2 diabetes or pre-diabetes herein include, in addition to gaboxadol or a pharmaceutically acceptable salt thereof, administering to a patient in need thereof about 0.1 mg to about 5 mg liraglutide or a pharmaceutically acceptable salt thereof. In embodiments, methods of treating a metabolic disorder such as type 1 diabetes, type 2 diabetes or pre-diabetes herein include administering gaboxadol or a pharmaceutically acceptable salt thereof, in combination with liraglutide or a pharmaceutically acceptable salt thereof.

In embodiments, about 0.2 mg to about 4 mg of liraglutide or a pharmaceutically acceptable salt thereof may be administered in 24 hours. In embodiments, about 0.3 mg to about 3 mg of liraglutide or a pharmaceutically acceptable salt thereof may be administered in 24 hours. In embodiments, about 0.4 mg to about 3 mg of liraglutide or a pharmaceutically acceptable salt thereof may be administered in 24 hours. In embodiments, about 0.5 mg to about 2 mg of liraglutide or a pharmaceutically acceptable salt thereof may be administered in 24 hours. In embodiments, about 0.6 mg to about 1.9 mg of liraglutide or a pharmaceutically acceptable salt thereof may be administered in 24 hours. In embodiments, about 0.6 mg to about 1.8 mg of liraglutide or a pharmaceutically acceptable salt thereof may be administered in 24 hours. In embodiments, about 0.7 mg to about 1.7 mg of liraglutide or a pharmaceutically acceptable salt thereof may be administered in 24 hours. In embodiments, about 0.8 mg to about 1.6 mg of liraglutide or a pharmaceutically acceptable salt thereof may be administered in 24 hours. In embodiments, about 0.6 mg to about 1.2 mg of liraglutide or a pharmaceutically acceptable salt thereof may be administered in 24 hours. In embodiments, about 1.2 mg to about 1.8 mg of liraglutide or a pharmaceutically acceptable salt thereof may be administered in 24 hours. In embodiments, about 0.6 mg to about 1.8 mg of liraglutide or a pharmaceutically acceptable salt thereof may be administered in 24 hours. In embodiments, about 0.6 mg of liraglutide or a pharmaceutically acceptable salt thereof may be administered in 24 hours. In embodiments, about 1.2 mg of liraglutide or a pharmaceutically acceptable salt thereof may be administered in 24 hours. In embodiments, about 1.8 mg of liraglutide or a pharmaceutically acceptable salt thereof may be administered in 24 hours. In embodiments, the liraglutide or a pharmaceutically acceptable salt thereof may be administered in divided doses over 24 hours. In embodiments, liraglutide may be administered once a day. In embodiments, the liraglutide or a pharmaceutically acceptable salt thereof may be administered parenterally. In embodiments, the liraglutide or a pharmaceutically acceptable salt thereof may be administered subcutaneously.

In embodiments methods of treating a metabolic disorder such as type 1 diabetes, type 2 diabetes or pre-diabetes include administering to a patient in need thereof a pharmaceutical composition including gaboxadol or a pharmaceutically acceptable salt thereof in combination with about 0.1 mg to about 5 mg liraglutide or a pharmaceutically acceptable salt thereof.

In embodiments, the compositions include 0.1 mg to 5 mg, 0.2 mg to 4 mg, 0.3 mg to 3 mg, 0.4 mg to 2 mg, 0.5 mg to 1.9 mg, 0.6 mg to 1.8 mg, 0.7 mg to 1.7 mg, 0.8 mg to 1.6 mg, 0.9 mg to 1.5 mg, 1 to 1.4 mg, 1.1 mg to 1.3 mg, 1.2 mg to 2 mg, 1.3 mg to 2 mg, 1.4 mg, to 2 mg, 1.5 mg to 2 mg, 1.2 mg to 1.8 mg, 0.6 mg to 1.2 mg, or 1.0 mg to 2.0 mg of liraglutide or a pharmaceutically acceptable salt thereof. In embodiments, the compositions include 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, or 2 mg liraglutide or a pharmaceutically acceptable salt thereof.

In embodiments, methods of treating a metabolic disorder such as type 1 diabetes, type 2 diabetes or pre-diabetes include, in addition to gaboxadol or a pharmaceutically acceptable salt thereof, administering to a patient in need thereof about 1 mcg to about 30 mcg lixisenatide or a pharmaceutically acceptable salt thereof. In embodiments, methods of treating a metabolic disorder such as type 1 diabetes, type 2 diabetes or pre-diabetes herein include administering gaboxadol or a pharmaceutically acceptable salt thereof, in combination with lixisenatide or a pharmaceutically acceptable salt thereof.

In embodiments, about 1 mcg to about 30 mcg of lixisenatide or a pharmaceutically acceptable salt thereof may be administered in 24 hours. In embodiments, about 2 mcg to about 30 mcg of lixisenatide or a pharmaceutically acceptable salt thereof may be administered in 24 hours. In embodiments, about 3 mcg to about 30 mg of lixisenatide or a pharmaceutically acceptable salt thereof may be administered in 24 hours. In embodiments, about 4 mcg to about 27 mcg of lixisenatide or a pharmaceutically acceptable salt thereof may be administered in 24 hours. In embodiments, about 5 mcg to about 25 mcg of lixisenatide or a pharmaceutically acceptable salt thereof may be administered in 24 hours. In embodiments, about 6 mcg to about 25 mg of lixisenatide or a pharmaceutically acceptable salt thereof may be administered in 24 hours. In embodiments, about 7.0 mcg to about 25 mcg of lixisenatide or a pharmaceutically acceptable salt thereof may be administered in 24 hours. In embodiments, about 8 mcg to about 20 mcg of lixisenatide or a pharmaceutically acceptable salt thereof may be administered in 24 hours. In embodiments, about 10 mcg to about 15 mcg of lixisenatide or a pharmaceutically acceptable salt thereof may be administered in 24 hours. In embodiments, about 15 mcg to about 20 mcg of lixisenatide or a pharmaceutically acceptable salt thereof may be administered in 24 hours. In embodiments, about 5 mcg of lixisenatide or a pharmaceutically acceptable salt thereof may be administered in 24 hours. In embodiments, about 10 mcg of lixisenatide or a pharmaceutically acceptable salt thereof may be administered in 24 hours. In embodiments, about 15 mcg of lixisenatide or a pharmaceutically acceptable salt thereof may be administered in 24 hours. In embodiments, about 20 mcg of lixisenatide or a pharmaceutically acceptable salt thereof may be administered in 24 hours. In embodiments, about 25 mcg of lixisenatide or a pharmaceutically acceptable salt thereof may be administered in 24 hours. In embodiments, the lixisenatide or a pharmaceutically acceptable salt thereof may be administered in divided doses over 24 hours. In embodiments, lixisenatide may be administered once a day. In embodiments, the lixisenatide or a pharmaceutically acceptable salt thereof may be administered parenterally. In embodiments, the lixisenatide or a pharmaceutically acceptable salt thereof may be administered subcutaneously.

In embodiments, the patient is administered 1.0 mcg to 10 mcg, 1.0 mcg to 15 mcg, 1.0 mcg to 20 mcg, 1.0 mcg to 25 mcg, 5 mcg to 10 mcg, 5 mcg to 25 mcg, 5 mcg to 20 mcg, 10 mcg to 15 mcg, 10 mcg to 20 mcg, 10 mcg to 25 mcg, 15 mcg to 20 mcg, 15 mcg to 25 mcg, 20 mcg to 25 mcg, or 25 mcg to 30 mcg, lixisenatide or a pharmaceutically acceptable salt thereof.

In embodiments, the patient is administered 1 mcg, 5 mcg, 10 mcg, 12 mcg, 15 mcg, 20 mcg, 25 mcg, or 30 mcg, lixisenatide or a pharmaceutically acceptable salt thereof.

In embodiments methods of treating a metabolic disorder such as type 1 diabetes, type 2 diabetes or pre-diabetes include administering to a patient in need thereof a pharmaceutical composition including gaboxadol or a pharmaceutically acceptable salt thereof in combination with about 1 mcg to about 30 mcg lixisenatide or a pharmaceutically acceptable salt thereof.

In embodiments, the compositions include 1.0 mcg to 10 mcg, 1.0 mcg to 15 mcg, 1.0 mcg to 25 mcg, 1 mcg to 30 mcg, 5 mcg to 10 mcg, 5 mcg to 20 mcg, 5 mcg to 25 mcg, 10 mcg to 15 mcg, 15 mcg to 20 mcg, 20 mcg to 25 mcg, or 25 mcg to 30 mcg, lixisenatide or a pharmaceutically acceptable salt thereof.

In embodiments, the compositions include 1 mcg, 5 mcg, 10 mcg, 15 mcg, 20 mcg, 25 mcg, or 30 mcg, lixisenatide or a pharmaceutically acceptable salt thereof.

In embodiments, methods of treating a metabolic disorder such as type 1 diabetes, type 2 diabetes or pre-diabetes include, in addition to gaboxadol or a pharmaceutically acceptable salt thereof, administering to a patient in need thereof about 10 mg to about 60 mg albiglutide or a pharmaceutically acceptable salt thereof. In embodiments, methods of treating a metabolic disorder such as type 1 diabetes, type 2 diabetes or pre-diabetes herein include administering gaboxadol or a pharmaceutically acceptable salt thereof, in combination with albiglutide or a pharmaceutically acceptable salt thereof.

In embodiments, about 1 mg to about 60 mg of albiglutide or a pharmaceutically acceptable salt thereof may be administered once weekly. In embodiments, about 2 mg to about 60 mg of albiglutide or a pharmaceutically acceptable salt thereof may be administered once weekly. In embodiments, about 3 mg to about 60 mg of albiglutide or a pharmaceutically acceptable salt thereof may be administered once weekly. In embodiments, about 4 mg to about 55 mg of albiglutide or a pharmaceutically acceptable salt thereof may be administered once weekly. In embodiments, about 5 mg to about 50 mg of albiglutide or a pharmaceutically acceptable salt thereof may be administered once weekly. In embodiments, about 6 mg to about 45 mg of albiglutide or a pharmaceutically acceptable salt thereof may be administered once weekly. In embodiments, about 7.0 mg to about 40 mg of albiglutide or a pharmaceutically acceptable salt thereof may be administered once weekly. In embodiments, about 8 mg to about 35 mg of albiglutide or a pharmaceutically acceptable salt thereof may be administered once weekly. In embodiments, about 10 mg to about 30 mg of albiglutide or a pharmaceutically acceptable salt thereof may be administered once weekly. In embodiments, about 10 mg to about 25 mg of albiglutide or a pharmaceutically acceptable salt thereof may be administered once weekly. In embodiments, about 10 mg to about 20 mg of albiglutide or a pharmaceutically acceptable salt thereof may be administered once weekly. In embodiments, about 10 mg to about 15 mg of albiglutide or a pharmaceutically acceptable salt thereof may be administered once weekly. In embodiments, about 15 mg to about 30 mg of albiglutide or a pharmaceutically acceptable salt thereof may be administered once weekly. In embodiments, about 15 mg to about 30 mg of albiglutide or a pharmaceutically acceptable salt thereof may be administered once weekly. In embodiments, about 10 mg of albiglutide or a pharmaceutically acceptable salt thereof may be administered once weekly. In embodiments, about 15 mg of albiglutide or a pharmaceutically acceptable salt thereof may be administered once weekly. In embodiments, about 20 mg of albiglutide or a pharmaceutically acceptable salt thereof may be administered once weekly. In embodiments, about 25 mg of albiglutide or a pharmaceutically acceptable salt thereof may be administered once weekly. In embodiments, about 30 mg of albiglutide or a pharmaceutically acceptable salt thereof may be administered once weekly. In embodiments, about 35 mg of albiglutide or a pharmaceutically acceptable salt thereof may be administered once weekly. In embodiments, about 40 mg of albiglutide or a pharmaceutically acceptable salt thereof may be administered once weekly. In embodiments, about 45 mg of albiglutide or a pharmaceutically acceptable salt thereof may be administered once weekly. In embodiments, about 50 mg of albiglutide or a pharmaceutically acceptable salt thereof may be administered once weekly. In embodiments, about 55 mg of albiglutide or a pharmaceutically acceptable salt thereof may be administered once weekly. In embodiments, about 60 mg of albiglutide or a pharmaceutically acceptable salt thereof may be administered once weekly. In embodiments, the albiglutide or a pharmaceutically acceptable salt thereof may be administered parenterally. In embodiments, the albiglutide or a pharmaceutically acceptable salt thereof may be administered subcutaneously.

In embodiments, the patient is administered 1.0 mg to 25 mg, 5 mg to 10 mg, 5 mg to 25 mg, 5 mg to 20 mg, 10 mg to 15 mg, 10 mg to 20 mg, 10 mg to 25 mg, 15 mg to 20 mg, 15 mg to 25 mg, 20 mg to 25 mg, or 25 mg to 30 mg, 30 mg to 35 mg, 35 mg to 40 mg, 45 mg to 50 mg, or 55 mg to 60 mg, albiglutide or a pharmaceutically acceptable salt thereof.

In embodiments, the patient is administered 1 mg, 5 mg, 10 mg, 12 mg, 15 mg, 17 mg, 20 mg, 25 mg, 30 mg, 35 mg, 40 mg, 45 mg, 50 mg, 55 mg, or 60 mg albiglutide or a pharmaceutically acceptable salt thereof.

In embodiments methods of treating a metabolic disorder such as type 1 diabetes, type 2 diabetes or pre-diabetes include administering to a patient in need thereof a pharmaceutical composition including gaboxadol or a pharmaceutically acceptable salt thereof in combination with about 1 mg to about 60 mg albiglutide or a pharmaceutically acceptable salt thereof.

In embodiments, the compositions include 1.0 mg to 10 mg, 1.0 mg to 15 mg, 1.0 mg to 25 mg, 1 mg to 30 mg, 1.0 mg to 35 mg, 1.0 mg to 40 mg, 1.0 mg to 45 mg, 1.0 mg to 50 mg, 1.0 mg to 55 mg, 1.0 mg to 60 mg, 5 mg to 10 mg, 5 mg to 20 mg, 5 mg to 25 mg, 5 mg to 30 mg, 5 mg to 35 mg, 5 mg to 40 mg, 5 mg to 45 mg, 5 mg to 50 mg, 5 mg to 55 mg, 5 mg to 60 mg, 10 mg to 15 mg, 15 mg to 20 mg, 20 mg to 25 mg, 25 mg to 30 mg, 25 mg to 35 mg, 25 mg to 40 mg, 25 mg to 45 mg, 25 mg to 50 mg, 25 mg to 55 mg, 30 mg to 35 mg, 30 mg to 40 mg, 35 mg to 45 mg, 35 mg to 40 mg, 35 mg to 45 mg, 35 mg to 50 mg, 35 mg to 55 mg, 35 mg to 60 mg, 40 mg to 45 mg, 40 mg to 50 mg, 40 mg to 55 mg, 40 mg to 60 mg, 45 mg to 50 mg, 45 mg to 55 mg, 45 mg to 60 mg, 50 mg to 55 mg, 50 mg to 60 mg, or 55 mg to 60 mg, albiglutide or a pharmaceutically acceptable salt thereof.

In embodiments, the compositions include 5 mg, 10 mg, 15 mg, 20 mg, 25 mg, 30 mg, 35 mg, 40 mg, 45 mg, 50 mg, 55 mg, or 60 mg albiglutide or a pharmaceutically acceptable salt thereof.

In embodiments, methods of treating a metabolic disorder such as type 1 diabetes, type 2 diabetes or pre-diabetes herein include, in addition to gaboxadol or a pharmaceutically acceptable salt thereof, administering to a patient in need thereof about 0.1 mg to about 5 mg dulaglutide or a pharmaceutically acceptable salt thereof. In embodiments, methods of treating a metabolic disorder such as type 1 diabetes, type 2 diabetes or pre-diabetes herein include administering gaboxadol or a pharmaceutically acceptable salt thereof, in combination with dulaglutide or a pharmaceutically acceptable salt thereof.

In embodiments, about 0.2 mg to about 4 mg of dulaglutide or a pharmaceutically acceptable salt thereof may be administered once weekly. In embodiments, about 0.3 mg to about 3 mg of dulaglutide or a pharmaceutically acceptable salt thereof may be administered once weekly. In embodiments, about 0.4 mg to about 3 mg of dulaglutide or a pharmaceutically acceptable salt thereof may be administered once weekly. In embodiments, about 0.5 mg to about 2 mg of dulaglutide or a pharmaceutically acceptable salt thereof may be administered once weekly. In embodiments, about 0.6 mg to about 1.9 mg of dulaglutide or a pharmaceutically acceptable salt thereof may be administered once weekly. In embodiments, about 0.6 mg to about 1.8 mg of dulaglutide or a pharmaceutically acceptable salt thereof may be administered once weekly. In embodiments, about 0.7 mg to about 1.7 mg of dulaglutide or a pharmaceutically acceptable salt thereof may be administered once weekly. In embodiments, about 0.75 mg to about 1.5 mg of dulaglutide or a pharmaceutically acceptable salt thereof may be administered once weekly. In embodiments, about 0.8 mg to about 1.6 mg of dulaglutide or a pharmaceutically acceptable salt thereof may be administered once weekly. In embodiments, about 0.75 mg to about 1.2 mg of dulaglutide or a pharmaceutically acceptable salt thereof may be administered once weekly. In embodiments, about 1.2 mg to about 1.8 mg of dulaglutide or a pharmaceutically acceptable salt thereof may be administered once weekly. In embodiments, about 0.6 mg to about 1.8 mg of dulaglutide or a pharmaceutically acceptable salt thereof may be administered once weekly. In embodiments, about 0.6 mg of dulaglutide or a pharmaceutically acceptable salt thereof may be administered once weekly. In embodiments, about 0.75 mg of dulaglutide or a pharmaceutically acceptable salt thereof may be administered once weekly. In embodiments, about 1.2 mg of dulaglutide or a pharmaceutically acceptable salt thereof may be administered once weekly. In embodiments, about 1.5 mg of dulaglutide or a pharmaceutically acceptable salt thereof may be administered once weekly. In embodiments, the dulaglutide or a pharmaceutically acceptable salt thereof may be administered in divided doses over 24 hours. In embodiments, dulaglutide may be administered once a week. In embodiments, the dulaglutide or a pharmaceutically acceptable salt thereof may be administered parenterally. In embodiments, the dulaglutide or a pharmaceutically acceptable salt thereof may be administered subcutaneously.

In embodiments methods of treating a metabolic disorder such as type 1 diabetes, type 2 diabetes or pre-diabetes include administering to a patient in need thereof a pharmaceutical composition including gaboxadol or a pharmaceutically acceptable salt thereof in combination with about 0.1 mg to about 5 mg dulaglutide or a pharmaceutically acceptable salt thereof.

In embodiments, the compositions include 0.1 mg to 5 mg, 0.2 mg to 4 mg, 0.3 mg to 3 mg, 0.4 mg to 2 mg, 0.5 mg to 1.9 mg, 0.6 mg to 1.8 mg, 0.7 mg to 1.7 mg, 0.75 mg to 1.5 mg, 0.75 mg, 0.8 mg to 1.6 mg, 0.9 mg to 1.5 mg, 1 to 1.4 mg, 1.1 mg to 1.3 mg, 1.2 mg to 2 mg, 1.3 mg to 2 mg, 1.4 mg, to 2 mg, 1.5 mg to 2 mg, 1.2 mg to 1.8 mg, 0.6 mg to 1.2 mg, or 1.0 mg to 2.0 mg of dulaglutide or a pharmaceutically acceptable salt thereof. In embodiments, the compositions include 0.1 mg, 0.2 mg, 0.3 mg, 0.4 mg, 0.5 mg, 0.6 mg, 0.7 mg, 0.75 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, or 2 mg dulaglutide or a pharmaceutically acceptable salt thereof.

In embodiments, methods of treating a metabolic disorder such as type 1 diabetes, type 2 diabetes or pre-diabetes include, in addition to gaboxadol or a pharmaceutically acceptable salt thereof, administering to a patient in need thereof about 1 mg to about 40 mg taspoglutide or a pharmaceutically acceptable salt thereof. In embodiments, methods of treating a metabolic disorder such as type 1 diabetes, type 2 diabetes or pre-diabetes herein include administering gaboxadol or a pharmaceutically acceptable salt thereof, in combination with taspoglutide or a pharmaceutically acceptable salt thereof.

In embodiments, about 1 mg to about 40 mg of taspoglutide or a pharmaceutically acceptable salt thereof may be administered once weekly. In embodiments, about 2 mg to about 40 mg of taspoglutide or a pharmaceutically acceptable salt thereof may be administered once weekly. In embodiments, about 3 mg to about 40 mg of taspoglutide or a pharmaceutically acceptable salt thereof may be administered once weekly. In embodiments, about 4 mg to about 35 mg of taspoglutide or a pharmaceutically acceptable salt thereof may be administered once weekly. In embodiments, about 5 mg to about 30 mg of taspoglutide or a pharmaceutically acceptable salt thereof may be administered once weekly. In embodiments, about 6 mg to about 45 mg of taspoglutide or a pharmaceutically acceptable salt thereof may be administered once weekly. In embodiments, about 7.0 mg to about 40 mg of taspoglutide or a pharmaceutically acceptable salt thereof may be administered once weekly. In embodiments, about 8 mg to about 35 mg of taspoglutide or a pharmaceutically acceptable salt thereof may be administered once weekly. In embodiments, about 10 mg to about 30 mg of taspoglutide or a pharmaceutically acceptable salt thereof may be administered once weekly. In embodiments, about 5 mg to about 10 mg of taspoglutide or a pharmaceutically acceptable salt thereof may be administered once weekly. In embodiments, about 5 mg to about 15 mg of taspoglutide or a pharmaceutically acceptable salt thereof may be administered once weekly. In embodiments, about 5 mg to about 20 mg of taspoglutide or a pharmaceutically acceptable salt thereof may be administered once weekly. In embodiments, about 10 mg to about 25 mg of taspoglutide or a pharmaceutically acceptable salt thereof may be administered once weekly. In embodiments, about 10 mg to about 20 mg of taspoglutide or a pharmaceutically acceptable salt thereof may be administered once weekly. In embodiments, about 10 mg to about 15 mg of taspoglutide or a pharmaceutically acceptable salt thereof may be administered once weekly. In embodiments, about 15 mg to about 30 mg of taspoglutide or a pharmaceutically acceptable salt thereof may be administered once weekly. In embodiments, about 15 mg to about 25 mg of taspoglutide or a pharmaceutically acceptable salt thereof may be administered once weekly. In embodiments, about 15 mg to about 20 mg of taspoglutide or a pharmaceutically acceptable salt thereof may be administered once weekly. In embodiments, about 5 mg of taspoglutide or a pharmaceutically acceptable salt thereof may be administered once weekly. In embodiments, about 10 mg of taspoglutide or a pharmaceutically acceptable salt thereof may be administered once weekly. In embodiments, about 15 mg of taspoglutide or a pharmaceutically acceptable salt thereof may be administered once weekly. In embodiments, about 20 mg of taspoglutide or a pharmaceutically acceptable salt thereof may be administered once weekly. In embodiments, about 25 mg of taspoglutide or a pharmaceutically acceptable salt thereof may be administered once weekly. In embodiments, about 30 mg of taspoglutide or a pharmaceutically acceptable salt thereof may be administered once weekly. In embodiments, about 35 mg of taspoglutide or a pharmaceutically acceptable salt thereof may be administered once weekly. In embodiments, about 40 mg of taspoglutide or a pharmaceutically acceptable salt thereof may be administered once weekly. In embodiments, the taspoglutide or a pharmaceutically acceptable salt thereof may be administered parenterally. In embodiments, the taspoglutide or a pharmaceutically acceptable salt thereof may be administered subcutaneously.

In embodiments, the patient is administered 1.0 mg to 25 mg, 5 mg to 10 mg, 5 mg to 15 mg, 5 mg to 20 mg, 10 mg to 15 mg, 10 mg to 20 mg, 10 mg to 25 mg, 15 mg to 20 mg, 15 mg to 25 mg, 20 mg to 25 mg, or 25 mg to 30 mg, 30 mg to 35 mg, or 35 mg to 40 mg, taspoglutide or a pharmaceutically acceptable salt thereof.

In embodiments, the patient is administered 1 mg, 5 mg, 10 mg, 12 mg, 15 mg, 17 mg, 20 mg, 25 mg, 30 mg, 35 mg, or 40 mg, taspoglutide or a pharmaceutically acceptable salt thereof.

In embodiments methods of treating a metabolic disorder such as type 1 diabetes, type 2 diabetes or pre-diabetes include administering to a patient in need thereof a pharmaceutical composition including gaboxadol or a pharmaceutically acceptable salt thereof in combination with about 1 mg to about 40 mg taspoglutide or a pharmaceutically acceptable salt thereof.

In embodiments, the compositions include 1.0 mg to 10 mg, 1.0 mg to 15 mg, 1.0 mg to 25 mg, 1 mg to 30 mg, 1.0 mg to 35 mg, 1.0 mg to 40 mg, 5 mg to 10 mg, 5 mg to 20 mg, 5 mg to 25 mg, 5 mg to 30 mg, 5 mg to 35 mg, 5 mg to 40 mg, 10 mg to 15 mg, 15 mg to 20 mg, 20 mg to 25 mg, 20 mg to 30 mg, 20 mg to 35 mg, 20 mg to 40 mg, 25 mg to 30 mg, 25 mg to 35 mg, 25 mg to 40 mg, 30 mg to 35 mg, 30 mg to 40 mg, 35 mg to 40 mg, taspoglutide or a pharmaceutically acceptable salt thereof.

In embodiments, the compositions include 5 mg, 10 mg, 15 mg, 20 mg, 25 mg, 30 mg, 35 mg, or 40 mg, taspoglutide or a pharmaceutically acceptable salt thereof.

In embodiments, methods of treating a metabolic disorder such as type 1 diabetes, type 2 diabetes or pre-diabetes herein include, in addition to gaboxadol or a pharmaceutically acceptable salt thereof, administering to a patient in need thereof about 0.1 mg to about 4 mg semaglutide or a pharmaceutically acceptable salt thereof. In embodiments, methods of treating a metabolic disorder such as type 1 diabetes, type 2 diabetes or pre-diabetes herein include administering gaboxadol or a pharmaceutically acceptable salt thereof, in combination with semaglutide or a pharmaceutically acceptable salt thereof.

In embodiments, about 0.2 mg to about 3 mg of semaglutide or a pharmaceutically acceptable salt thereof may be administered once weekly. In embodiments, about 0.3 mg to about 2 mg of semaglutide or a pharmaceutically acceptable salt thereof may be administered once weekly. In embodiments, about 0.4 mg to about 2 mg of semaglutide or a pharmaceutically acceptable salt thereof may be administered once weekly. In embodiments, about 0.5 mg to about 1 mg of semaglutide or a pharmaceutically acceptable salt thereof may be administered once weekly. In embodiments, about 0.6 mg to about 1.5 mg of semaglutide or a pharmaceutically acceptable salt thereof may be administered once weekly. In embodiments, about 0.5 mg to about 0.8 mg of semaglutide or a pharmaceutically acceptable salt thereof may be administered once weekly. In embodiments, about 0.4 mg to about 0.7 mg of semaglutide or a pharmaceutically acceptable salt thereof may be administered once weekly. In embodiments, about 0.75 mg to about 1.5 mg of semaglutide or a pharmaceutically acceptable salt thereof may be administered once weekly. In embodiments, about 0.3 mg to about 0.5 mg of semaglutide or a pharmaceutically acceptable salt thereof may be administered once weekly. In embodiments, about 0.5 mg to about 0.9 mg of semaglutide or a pharmaceutically acceptable salt thereof may be administered once weekly. In embodiments, about 1.0 mg to about 1.5 mg of semaglutide or a pharmaceutically acceptable salt thereof may be administered once weekly. In embodiments, about 0.2 mg to about 0.5 mg of semaglutide or a pharmaceutically acceptable salt thereof may be administered once weekly. In embodiments, about 0.1 mg of semaglutide or a pharmaceutically acceptable salt thereof may be administered once weekly. In embodiments, about 0.2 mg of semaglutide or a pharmaceutically acceptable salt thereof may be administered once weekly. In embodiments, about 0.3 mg of semaglutide or a pharmaceutically acceptable salt thereof may be administered once weekly. In embodiments, about 0.4 mg of semaglutide or a pharmaceutically acceptable salt thereof may be administered once weekly. In embodiments, about 0.5 mg of semaglutide or a pharmaceutically acceptable salt thereof may be administered once weekly. In embodiments, about 0.6 mg of semaglutide or a pharmaceutically acceptable salt thereof may be administered once weekly. In embodiments, about 0.7 mg of semaglutide or a pharmaceutically acceptable salt thereof may be administered once weekly. In embodiments, about 0.8 mg of semaglutide or a pharmaceutically acceptable salt thereof may be administered once weekly. In embodiments, about 0.9 mg of semaglutide or a pharmaceutically acceptable salt thereof may be administered once weekly. In embodiments, about 1.0 mg of semaglutide or a pharmaceutically acceptable salt thereof may be administered once weekly. In embodiments, about 1.1 mg of semaglutide or a pharmaceutically acceptable salt thereof may be administered once weekly. In embodiments, about 1.2 mg of semaglutide or a pharmaceutically acceptable salt thereof may be administered once weekly. In embodiments, the dulaglutide or a pharmaceutically acceptable salt thereof may be administered in divided doses over 24 hours. In embodiments, semaglutide may be administered once a week. In embodiments, the semaglutide or a pharmaceutically acceptable salt thereof may be administered parenterally. In embodiments, the semaglutide or a pharmaceutically acceptable salt thereof may be administered subcutaneously.

In embodiments methods of treating a metabolic disorder such as type 1 diabetes, type 2 diabetes or pre-diabetes include administering to a patient in need thereof a pharmaceutical composition including gaboxadol or a pharmaceutically acceptable salt thereof in combination with about 0.1 mg to about 4 mg semaglutide or a pharmaceutically acceptable salt thereof.

In embodiments, the compositions include 0.1 mg to 4 mg, 0.2 mg to 4 mg, 0.3 mg to 3 mg, 0.4 mg to 2 mg, 0.5 mg to 2 mg, 0.1 mg to 1 mg, 0.2 mg to 1 mg, 0.3 mg to 1 mg, 0.4 mg to 1 mg, 0.5 mg to 1 mg, 0.6 mg to 1 mg, 0.7 mg to 1 mg, 0.8 mg to 1 mg, 0.9 mg to 1 mg, 0.6 mg to 1.5 mg, 0.7 mg to 1.7 mg, 0.75 mg to 1.5 mg, 0.75 mg, 0.8 mg to 1.6 mg, 0.9 mg to 1.5 mg, 1 to 1.4 mg, 1.1 mg to 1.3 mg, 1.2 mg to 2 mg, 1.3 mg to 2 mg, 1.4 mg, to 2 mg, 1.5 mg to 2 mg, 1.2 mg to 1.8 mg, 0.6 mg to 1.2 mg, or 1.0 mg to 2.0 mg of semaglutide or a pharmaceutically acceptable salt thereof. In embodiments, the compositions include 0.1 mg, 0.2 mg, 0.3 mg, 0.4 mg, 0.5 mg, 0.6 mg, 0.7 mg, 0.75 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2 mg, 3 mg, or 4 mg semaglutide or a pharmaceutically acceptable salt thereof.

In embodiments, a patient in need thereof is administered gaboxadol or a pharmaceutically acceptable salt thereof in combination with a sulfonylurea or a pharmaceutically acceptable salt thereof. In embodiments a patient in need thereof is administered a pharmaceutical composition including gaboxadol or a pharmaceutically acceptable salt thereof in combination with a sulfonylurea or a pharmaceutically acceptable salt thereof. Examples of sulfonylureas include acetohexamide, carbutamide, chlorpropamide, glycyclamide, metahexamide, tolazamide, glibornuride, gliclazide, glipizide, gliquidone, glisoxepide, glyclopyramide and glimepiride.

In embodiments, methods of treating a metabolic disorder such as type 1 diabetes, type 2 diabetes or pre-diabetes herein include, in addition to gaboxadol or a pharmaceutically acceptable salt thereof, administering to a patient in need thereof about 50 mg to about 1000 mg acetohexamide or a pharmaceutically acceptable salt thereof. In embodiments, methods of treating a metabolic disorder such as type 1 diabetes, type 2 diabetes or pre-diabetes herein include administering gaboxadol or a pharmaceutically acceptable salt thereof, in combination with acetohexamide or a pharmaceutically acceptable salt thereof.

In embodiments, about 250 mg to about 500 mg of acetohexamide or a pharmaceutically acceptable salt thereof may be administered in 24 hours. In embodiments, about 200 mg to about 400 mg of acetohexamide or a pharmaceutically acceptable salt thereof may be administered in 24 hours. In embodiments, the acetohexamide or a pharmaceutically acceptable salt thereof may be administered in divided doses over 24 hours. In embodiments, acetohexamide or a pharmaceutically acceptable salt thereof may be administered once a day, e.g., with a morning meal. In embodiments, acetohexamide or a pharmaceutically acceptable salt thereof can be given in doses varying from about 50 mg to 1000 mg per day using various dosing regimens from about 100 mg to 500 mg or 200 mg to 850 mg (1-3 times a day), or about 300 mg to 1000 mg once or twice a day. Particular dosage strengths may be 100, 150, 200, 250, 300, 350, 400, 450, 500, 625, 750, 850 and 1000 mg of acetohexamide.

In embodiments, the patient is administered 50 mg to 75 mg, 75 mg to 100 mg, 100 mg to 125 mg, 125 mg to 150 mg, 150 mg to 175 mg, 175 mg to 200 mg, 200 mg to 225 mg, 225 mg to 250 mg, 250 mg to 275 mg, 275 mg to 300 mg, 300 mg, to 325 mg, 325 mg to 350 mg, 350 mg to 375 mg, 375 mg to 400 mg, 400 mg to 425 mg, 425 mg to 450 mg, 450 mg to 475 mg, 475 mg to 500 mg, 500 mg to 525 mg, 525 mg to 550 mg, 550 mg to 575 mg, 575 mg to 600 mg, 600 mg to 625 mg, 625 mg to 650 mg, 650 mg to 675 mg, 675 mg to 700 mg, 700 mg to 725 mg, 725 mg to 750 mg, 750 mg to 775 mg, 775 mg to 800 mg, 800 mg to 825 mg, 825 mg to 850 mg, 850 mg to 875 mg, 875 mg to 900 mg, 900 mg to 925 mg, 925 mg to 950 mg, 950 mg to 975 mg, or 975 mg to 1000 mg, acetohexamide or a pharmaceutically acceptable salt thereof.

In embodiments, the patient is administered 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, or 1000 mg, acetohexamide or a pharmaceutically acceptable salt thereof.

In embodiments methods of treating a metabolic disorder such as type 1 diabetes, type 2 diabetes or pre-diabetes include administering to a patient in need thereof a pharmaceutical composition including gaboxadol or a pharmaceutically acceptable salt thereof in combination with about 50 mg to about 1000 mg acetohexamide or a pharmaceutically acceptable salt thereof.

In embodiments, the pharmaceutical compositions include 50 mg to 75 mg, 75 mg to 100 mg, 100 mg to 125 mg, 125 mg to 150 mg, 150 mg to 175 mg, 175 mg to 200 mg, 200 mg to 225 mg, 225 mg to 250 mg, 250 mg to 275 mg, 275 mg to 300 mg, 300 mg to 325 mg, 325 mg to 350 mg, 350 mg to 375 mg, 375 mg to 400 mg, 400 mg to 425 mg, 425 mg to 450 mg, 450 mg to 475 mg, 475 mg to 500 mg, 500 mg to 525 mg, 525 mg to 550 mg, 550 mg to 575 mg, 575 mg to 600 mg, 600 mg to 625 mg, 625 mg to 650 mg, 650 mg to 675 mg, 675 mg to 700 mg, 700 mg to 725 mg, 725 mg to 750 mg, 750 mg to 775 mg, 775 mg to 800 mg, 800 mg to 825 mg, 825 mg to 850 mg, 850 mg to 875 mg, 875 mg to 900 mg, 900 mg to 925 mg, 925 mg to 950 mg, 950 mg to 975 mg, or 975 mg to 1000 mg, acetohexamide or a pharmaceutically acceptable salt thereof.

In embodiments, the pharmaceutical compositions include 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, or 1000 mg, acetohexamide or a pharmaceutically acceptable salt thereof.

In embodiments, methods of treating a metabolic disorder such as type 1 diabetes, type 2 diabetes or pre-diabetes herein include, in addition to gaboxadol or a pharmaceutically acceptable salt thereof, administering to a patient in need thereof about 10 mg to about 750 mg chlorpropamide or a pharmaceutically acceptable salt thereof. In embodiments, methods of treating a metabolic disorder such as type 1 diabetes, type 2 diabetes or pre-diabetes herein include administering gaboxadol or a pharmaceutically acceptable salt thereof, in combination with chlorpropamide or a pharmaceutically acceptable salt thereof.

In embodiments, about 100 mg to about 500 mg of chlorpropamide or a pharmaceutically acceptable salt thereof may be administered in 24 hours. In embodiments, about 250 mg to about 500 mg of chlorpropamide or a pharmaceutically acceptable salt thereof may be administered in 24 hours. In embodiments, the chlorpropamide or a pharmaceutically acceptable salt thereof may be administered in divided doses over 24 hours. In embodiments, chlorpropamide or a pharmaceutically acceptable salt thereof may be administered once a day, e.g., with a meal. In embodiments, chlorpropamide or a pharmaceutically acceptable salt thereof can be given in doses varying from about 50 mg to 750 mg per day using various dosing regimens from about 100 mg to 500 mg or 200 mg to 700 mg (1-3 times a day), or about 250 mg to 500 mg once or twice a day. Particular dosage strengths may be 50, 100, 150, 200, 250, 300, 350, 400, 450, 500, 550, 600, 625, or 750 mg of chlorpropamide.

In embodiments, the patient is administered 50 mg to 75 mg, 75 mg to 100 mg, 100 mg to 125 mg, 125 mg to 150 mg, 150 mg to 175 mg, 175 mg to 200 mg, 200 mg to 225 mg, 225 mg to 250 mg, 250 mg to 275 mg, 275 mg to 300 mg, 300 mg, to 325 mg, 325 mg to 350 mg, 350 mg to 375 mg, 375 mg to 400 mg, 400 mg to 425 mg, 425 mg to 450 mg, 450 mg to 475 mg, 475 mg to 500 mg, 500 mg to 525 mg, 525 mg to 550 mg, 550 mg to 575 mg, 575 mg to 600 mg, 600 mg to 625 mg, 625 mg to 650 mg, 650 mg to 675 mg, 675 mg to 700 mg, 700 mg to 725 mg, or 725 mg to 750 mg, chlorpropamide or a pharmaceutically acceptable salt thereof.

In embodiments, the patient is administered 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, or 750 mg, chlorpropamide or a pharmaceutically acceptable salt thereof.

In embodiments methods of treating a metabolic disorder such as type 1 diabetes, type 2 diabetes or pre-diabetes include administering to a patient in need thereof a pharmaceutical composition including gaboxadol or a pharmaceutically acceptable salt thereof in combination with about 50 mg to about 750 mg acetohexamide or a pharmaceutically acceptable salt thereof.

In embodiments, the pharmaceutical compositions herein include 50 mg to 75 mg, 75 mg to 100 mg, 100 mg to 125 mg, 125 mg to 150 mg, 150 mg to 175 mg, 175 mg to 200 mg, 200 mg to 225 mg, 225 mg to 250 mg, 250 mg to 275 mg, 275 mg to 300 mg, 300 mg to 325 mg, 325 mg to 350 mg, 350 mg to 375 mg, 375 mg to 400 mg, 400 mg to 425 mg, 425 mg to 450 mg, 450 mg to 475 mg, 475 mg to 500 mg, 500 mg to 525 mg, 525 mg to 550 mg, 550 mg to 575 mg, 575 mg to 600 mg, 600 mg to 625 mg, 625 mg to 650 mg, 650 mg to 675 mg, 675 mg to 700 mg, 700 mg to 725 mg, or 725 mg to 750 mg, chlorpropamide or a pharmaceutically acceptable salt thereof.

In embodiments, the pharmaceutical compositions include 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, or 750 mg, chlorpropamide or a pharmaceutically acceptable salt thereof.

In embodiments, methods of treating a metabolic disorder such as type 1 diabetes, type 2 diabetes or pre-diabetes herein include, in addition to gaboxadol or a pharmaceutically acceptable salt thereof, administering to a patient in need thereof about 50 mg to about 1000 mg tolazamide or a pharmaceutically acceptable salt thereof. In embodiments, methods of treating a metabolic disorder such as type 1 diabetes, type 2 diabetes or pre-diabetes herein include administering gaboxadol or a pharmaceutically acceptable salt thereof, in combination with tolazamide or a pharmaceutically acceptable salt thereof.

In embodiments, about 100 mg to about 1000 mg of tolazamide or a pharmaceutically acceptable salt thereof may be administered in 24 hours. In embodiments, about 200 mg to about 750 mg of tolazamide or a pharmaceutically acceptable salt thereof may be administered in 24 hours. In embodiments, the tolazamide or a pharmaceutically acceptable salt thereof may be administered in divided doses over 24 hours. In embodiments, tolazamide or a pharmaceutically acceptable salt thereof may be administered once a day, e.g., with a morning meal. In embodiments, tolazamide or a pharmaceutically acceptable salt thereof can be given in doses varying from about 50 mg to 1000 mg per day using various dosing regimens from about 50 mg to 500 mg, or 200 mg to 700 mg (1-3 times a day), or about 50 mg to 500, 75 mg to 100 mg, 100 mg to 150 mg, 150 mg to 200 mg, 200 mg to 250 mg, 300 mg to 350 mg, 350 mg to 400 mg, 450 mg to 500 mg, 550 mg to 600 mg, 650 mg to 700 mg, 750 mg to 800 mg, 850 mg to 900 mg, or 950 mg to 1000 mg, once or twice a day. Particular dosage strengths may be 50, 100, 125, 150, 175, 200, 225, 250, 275, 300, 325, 350, 375, 400, 425, 450, 475, 500, 525, 550, 575, 600, 625, 650, 675, 700, 725, or 750 mg of tolazamide or a pharmaceutically acceptable salt thereof.

In embodiments, the patient is administered 50 mg to 75 mg, 75 mg to 100 mg, 100 mg to 125 mg, 125 mg to 150 mg, 150 mg to 175 mg, 175 mg to 200 mg, 200 mg to 225 mg, 225 mg to 250 mg, 250 mg to 275 mg, 275 mg to 300 mg, 300 mg, to 325 mg, 325 mg to 350 mg, 350 mg to 375 mg, 375 mg to 400 mg, 400 mg to 425 mg, 425 mg to 450 mg, 450 mg to 475 mg, 475 mg to 500 mg, 500 mg to 525 mg, 525 mg to 550 mg, 550 mg to 575 mg, 575 mg to 600 mg, 600 mg to 625 mg, 625 mg to 650 mg, 650 mg to 675 mg, 675 mg to 700 mg, 700 mg to 725 mg, or 725 mg to 750 mg, tolazamide or a pharmaceutically acceptable salt thereof.

In embodiments, the patient is administered 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, or 750 mg, tolazamide or a pharmaceutically acceptable salt thereof.

In embodiments methods of treating a metabolic disorder such as type 1 diabetes, type 2 diabetes or pre-diabetes include administering to a patient in need thereof a pharmaceutical composition including gaboxadol or a pharmaceutically acceptable salt thereof in combination with about 50 mg to about 1000 mg tolazamide or a pharmaceutically acceptable salt thereof.

In embodiments, the pharmaceutical compositions herein include 50 mg to 75 mg, 75 mg to 100 mg, 100 mg to 125 mg, 125 mg to 150 mg, 150 mg to 175 mg, 175 mg to 200 mg, 200 mg to 225 mg, 225 mg to 250 mg, 250 mg to 275 mg, 275 mg to 300 mg, 300 mg to 325 mg, 325 mg to 350 mg, 350 mg to 375 mg, 375 mg to 400 mg, 400 mg to 425 mg, 425 mg to 450 mg, 450 mg to 475 mg, 475 mg to 500 mg, 500 mg to 525 mg, 525 mg to 550 mg, 550 mg to 575 mg, 575 mg to 600 mg, 600 mg to 625 mg, 625 mg to 650 mg, 650 mg to 675 mg, 675 mg to 700 mg, 700 mg to 725 mg, or 725 mg to 750 mg, tolazamide or a pharmaceutically acceptable salt thereof.

In embodiments, the pharmaceutical compositions include 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, or 750 mg, tolazamide or a pharmaceutically acceptable salt thereof.

In embodiments, methods of treating a metabolic disorder such as type 1 diabetes, type 2 diabetes or pre-diabetes herein include, in addition to gaboxadol or a pharmaceutically acceptable salt thereof, administering to a patient in need thereof about 50 mg to about 3000 mg tolbutamide or a pharmaceutically acceptable salt thereof. In embodiments, methods of treating a metabolic disorder such as type 1 diabetes, type 2 diabetes or pre-diabetes herein include administering gaboxadol or a pharmaceutically acceptable salt thereof, in combination with tolbutamide or a pharmaceutically acceptable salt thereof.

In embodiments, about 50 mg to about 3000 mg of tolbutamide or a pharmaceutically acceptable salt thereof may be administered in 24 hours. In embodiments, the tolbutamide or a pharmaceutically acceptable salt thereof may be administered in divided doses over 24 hours. In embodiments, tolbutamide may be administered once a day, e.g., with a morning meal. In embodiments, tolbutamide may be administered two or three times daily, e.g., with meals. In embodiments, tolbutamide can be given in doses varying from about 500 mg to 2000 mg up to 2500 mg or 3000 mg per day using various dosing regimens from about 100 mg to 500 mg or 200 mg to 850 mg (1-3 times a day), or about 300 mg to 1000 mg once or twice a day.

In embodiments, the patient is administered 50 mg to 75 mg, 75 mg to 100 mg, 100 mg to 125 mg, 125 mg to 150 mg, 150 mg to 175 mg, 175 mg to 200 mg, 200 mg to 225 mg, 225 mg to 250 mg, 250 mg to 275 mg, 275 mg to 300 mg, 300 mg, to 325 mg, 325 mg to 350 mg, 350 mg to 375 mg, 375 mg to 400 mg, 400 mg to 425 mg, 425 mg to 450 mg, 450 mg to 475 mg, 475 mg to 500 mg, 500 mg to 525 mg, 525 mg to 550 mg, 550 mg to 575 mg, 575 mg to 600 mg, 600 mg to 625 mg, 625 mg to 650 mg, 650 mg to 675 mg, 675 mg to 700 mg, 700 mg to 725 mg, 725 mg to 750 mg, 750 mg to 775 mg, 775 mg to 800 mg, 800 mg to 825 mg, 825 mg to 850 mg, 850 mg to 875 mg, 875 mg to 900 mg, 900 mg to 925 mg, 925 mg to 950 mg, 950 mg to 975 mg, 975 mg to 1000 mg, 1000 mg to 1025 mg, 1025 mg to 1050 mg, 1050 mg to 1075 mg, 1075 mg to 1100 mg, 1100 mg to 1125 mg, 1125 mg to 1150 mg, 1150 mg to 1175 mg, 1175 mg to 1200 mg, 1200 mg to 1225 mg, 1225 mg to 1250 mg, 1250 mg to 1275 mg, 1275 mg to 1300 mg, 1300 mg to 1325 mg, 1325 mg to 1350 mg, 1350 mg to 1375 mg, 1375 mg to 1400 mg, 1400 mg to 1425 mg, 1425 mg to 1450 mg, 1450 mg to 1475 mg, 1475 mg to 1500 mg, 1500 mg to 1525 mg, 1525 mg to 1550 mg, 1550 mg to 1575 mg, 1575 mg to 1600 mg, 1600 mg to 1625 mg, 1625 mg to 1650 mg, 1650 mg to 1675 mg, 1675 mg to 1700 mg, 1700 mg to 1725 mg, 1725 mg to 1750 mg, 1750 mg to 1775 mg, 1775 mg to 1800 mg, 1800 mg to 1825 mg, 1825 mg to 1850 mg, 1850 mg to 1875 mg, 1875 mg to 1900 mg, 1900 mg to 1925 mg, 1925 mg to 1950 mg, 1950 mg to 1975 mg, 1975 mg to 2000 mg, 2000 mg to 2025 mg, 2025 mg to 2050 mg, 2050 mg to 2075 mg, 2075 mg to 2100 mg, 2100 mg to 2125 mg, 2125 mg to 2150 mg, 2150 mg to 2175 mg, 2175 mg to 2200 mg, 2200 mg to 2225 mg, 2225 mg to 2250 mg, 2250 mg to 2275 mg, 2275 mg to 2300 mg, 2300 mg to 2325 mg, 2325 mg to 2350 mg, 2350 mg to 2375 mg, 2375 mg to 2400 mg, 2400 mg to 2425 mg, 2425 mg to 2450 mg, 2450 mg to 2475 mg, 2475 mg to 2500 mg, 2500 mg to 2525 mg, 2525 mg to 2550 mg, 2550 mg to 2575 mg, 2575 mg to 2600 mg, 2600 mg to 2625 mg, 2625 mg to 2650 mg, 2650 mg to 2675 mg, 2675 mg to 2700 mg, 2700 mg to 2725 mg, 2725 mg to 2750 mg, 2750 mg to 2775 mg, 2775 mg to 2800 mg, 2800 mg to 2825 mg, 2825 mg to 2850 mg, 2850 mg to 2875 mg, 2875 mg to 2900 mg, 2900 mg to 2925 mg, 2925 mg to 2950 mg, 2950 mg to 2975 mg, or 2975 mg to 3000 mg, tolbutamide or a pharmaceutically acceptable salt thereof.

In embodiments, the patient is administered 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1225 mg, 1250 mg, 1275 mg, 1300 mg, 1325 mg, 1350 mg, 1375 mg, 1400 mg, 1425 mg, 1450 mg, 1475 mg, 1500 mg, 1525 mg, 1550 mg, 1575 mg, 1600 mg, 1625 mg, 1650 mg, 1675 mg, 1700 mg, 1725 mg, 1750 mg, 1775 mg, 1800 mg, 1825 mg, 1850 mg, 1875 mg, 1900 mg, 1925 mg, 1950 mg, 1975 mg, 2000 mg, 2025 mg, 2250 mg, 2275 mg, 2300 mg, 2325 mg, 2350 mg, 2375 mg, 2400 mg, 2425 mg, 2450 mg, 2475 mg, 2500 mg, 2525 mg, 2550 mg, 2575 mg, 2600 mg, 2625 mg, 2650 mg, 2675 mg, 2700 mg, 2725 mg, 2750 mg, 2775 mg, 2800 mg, 2825 mg, 2850 mg, 2875 mg, 2900 mg, 2925 mg, 2950 mg, 2975 mg, or 3000 mg, tolbutamide or a pharmaceutically acceptable salt thereof.

In embodiments methods of treating a metabolic disorder such as type 1 diabetes, type 2 diabetes or pre-diabetes include administering to a patient in need thereof a pharmaceutical composition including gaboxadol or a pharmaceutically acceptable salt thereof in combination with about 50 mg to about 3000 mg tolbutamide or a pharmaceutically acceptable salt thereof.

In embodiments, the pharmaceutical compositions include 50 mg to 75 mg, 75 mg to 100 mg, 100 mg to 125 mg, 125 mg to 150 mg, 150 mg to 175 mg, 175 mg to 200 mg, 200 mg to 225 mg, 225 mg to 250 mg, 250 mg to 275 mg, 275 mg to 300 mg, 300 mg to 325 mg, 325 mg to 350 mg, 350 mg to 375 mg, 375 mg to 400 mg, 400 mg to 425 mg, 425 mg to 450 mg, 450 mg to 475 mg, 475 mg to 500 mg, 500 mg to 525 mg, 525 mg to 550 mg, 550 mg to 575 mg, 575 mg to 600 mg, 600 mg to 625 mg, 625 mg to 650 mg, 650 mg to 675 mg, 675 mg to 700 mg, 700 mg to 725 mg, 725 mg to 750 mg, 750 mg to 775 mg, 775 mg to 800 mg, 800 mg to 825 mg, 825 mg to 850 mg, 850 mg to 875 mg, 875 mg to 900 mg, 900 mg to 925 mg, 925 mg to 950 mg, 950 mg to 975 mg, 975 mg to 1000 mg, 1000 mg to 1025 mg, 1025 mg to 1050 mg, 1050 mg to 1075 mg, 1075 mg to 1100 mg, 1100 mg to 1125 mg, 1125 mg to 1150 mg, 1150 mg to 1175 mg, 1175 mg to 1200 mg, 1200 mg to 1225 mg, 1225 mg to 1250 mg, 1250 mg to 1275 mg, 1275 mg to 1300 mg, 1300 mg to 1325 mg, 1325 mg to 1350 mg, 1350 mg to 1375 mg, 1375 mg to 1400 mg, 1400 mg to 1425 mg, 1425 mg to 1450 mg, 1450 mg to 1475 mg, 1475 mg to 1500 mg, 1500 mg to 1525 mg, 1525 mg to 1550 mg, 1550 mg to 1575 mg, 1575 mg to 1600 mg, 1600 mg to 1625 mg, 1625 mg to 1650 mg, 1650 mg to 1675 mg, 1675 mg to 1700 mg, 1700 mg to 1725 mg, 1725 mg to 1750 mg, 1750 mg to 1775 mg, 1775 mg to 1800 mg, 1800 mg to 1825 mg, 1825 mg to 1850 mg, 1850 mg to 1875 mg, 1875 mg to 1900 mg, 1900 mg to 1925 mg, 1925 mg to 1950 mg, 1950 mg to 1975 mg, 1975 mg to 2000 mg, 2000 mg to 2025 mg, 2025 mg to 2050 mg, 2050 mg to 2075 mg, 2075 mg to 2100 mg, 2100 mg to 2125 mg, 2125 mg to 2150 mg, 2150 mg to 2175 mg, 2175 mg to 2200 mg, 2200 mg to 2225 mg, 2225 mg to 2250 mg, 2250 mg to 2275 mg, 2275 mg to 2300 mg, 2300 mg to 2325 mg, 2325 mg to 2350 mg, 2350 mg to 2375 mg, 2375 mg to 2400 mg, 2400 mg to 2425 mg, 2425 mg to 2450 mg, 2450 mg to 2475 mg, 2475 mg to 2500 mg, 2500 mg to 2525 mg, 2525 mg to 2550 mg, 2550 mg to 2575 mg, 2575 mg to 2600 mg, 2600 mg to 2625 mg, 2625 mg to 2650 mg, 2650 mg to 2675 mg, 2675 mg to 2700 mg, 2700 mg to 2725 mg, 2725 mg to 2750 mg, 2750 mg to 2775 mg, 2775 mg to 2800 mg, 2800 mg to 2825 mg, 2825 mg to 2850 mg, 2850 mg to 2875 mg, 2875 mg to 2900 mg, 2900 mg to 2925 mg, 2925 mg to 2950 mg, 2950 mg to 2975 mg, 2975 mg to 3000 mg, tolbutamide or a pharmaceutically acceptable salt thereof.

In embodiments, the pharmaceutical compositions include 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1225 mg, 1250 mg, 1275 mg, 1300 mg, 1325 mg, 1350 mg, 1375 mg, 1400 mg, 1425 mg, 1450 mg, 1475 mg, 1500 mg, 1525 mg, 1550 mg, 1575 mg, 1600 mg, 1625 mg, 1650 mg, 1675 mg, 1700 mg, 1725 mg, 1750 mg, 1775 mg, 1800 mg, 1825 mg, 1850 mg, 1875 mg, 1900 mg, 1925 mg, 1950 mg, 1975 mg, 2000 mg, 2025 mg, 2250 mg, 2275 mg, 2300 mg, 2325 mg, 2350 mg, 2375 mg, 2400 mg, 2425 mg, 2450 mg, 2475 mg, 2500 mg, 2525 mg, 2550 mg, 2575 mg, 2600 mg, 2625 mg, 2650 mg, 2675 mg, 2700 mg, 2725 mg, 2750 mg, 2775 mg, 2800 mg, 2825 mg, 2850 mg, 2875 mg, 2900 mg, 2925 mg, 2950 mg, 2975 mg, 3000 mg, tolbutamide or a pharmaceutically acceptable salt thereof.

In embodiments, methods of treating a metabolic disorder such as type 1 diabetes, type 2 diabetes or pre-diabetes include, in addition to gaboxadol or a pharmaceutically acceptable salt thereof, administering to a patient in need thereof about 1 mg to about 100 mg glibornuride or a pharmaceutically acceptable salt thereof. In embodiments, methods of treating a metabolic disorder such as type 1 diabetes, type 2 diabetes or pre-diabetes herein include administering gaboxadol or a pharmaceutically acceptable salt thereof, in combination with glibornuride or a pharmaceutically acceptable salt thereof.

In embodiments, about 1 mg to about 100 mg of glibornuride or a pharmaceutically acceptable salt thereof may be administered once daily. In embodiments, about 2 mg to about 100 mg of glibornuride or a pharmaceutically acceptable salt thereof may be administered once daily. In embodiments, about 3 mg to about 80 mg of glibornuride or a pharmaceutically acceptable salt thereof may be administered once daily. In embodiments, about 5 mg to about 75 mg of glibornuride or a pharmaceutically acceptable salt thereof may be administered once daily. In embodiments, about 10 mg to about 75 mg of glibornuride or a pharmaceutically acceptable salt thereof may be administered once daily. In embodiments, about 12.5 mg to about 75 mg of glibornuride or a pharmaceutically acceptable salt thereof may be administered once daily. In embodiments, about 7.0 mg to about 70 mg of glibornuride or a pharmaceutically acceptable salt thereof may be administered once daily. In embodiments, about 8 mg to about 25 mg of glibornuride or a pharmaceutically acceptable salt thereof may be administered once daily. In embodiments, about 10 mg to about 30 mg of glibornuride or a pharmaceutically acceptable salt thereof may be administered once daily. In embodiments, about 10 mg to about 35 mg of glibornuride or a pharmaceutically acceptable salt thereof may be administered once daily. In embodiments, about 10 mg to about 20 mg of glibornuride or a pharmaceutically acceptable salt thereof may be administered once daily. In embodiments, about 10 mg to about 15 mg of glibornuride or a pharmaceutically acceptable salt thereof may be administered once daily. In embodiments, about 15 mg to about 30 mg of glibornuride or a pharmaceutically acceptable salt thereof may be administered once daily. In embodiments, about 15 mg to about 30 mg of glibornuride or a pharmaceutically acceptable salt thereof may be administered once daily. In embodiments, about 10 mg of glibornuride or a pharmaceutically acceptable salt thereof may be administered once daily. In embodiments, about 7.5 mg of glibornuride or a pharmaceutically acceptable salt thereof may be administered once daily. In embodiments, about 10 mg of glibornuride or a pharmaceutically acceptable salt thereof may be administered once daily. In embodiments, about 12.5 mg of glibornuride or a pharmaceutically acceptable salt thereof may be administered once daily. In embodiments, about 15 mg of glibornuride or a pharmaceutically acceptable salt thereof may be administered once daily. In embodiments, about 20 mg of glibornuride or a pharmaceutically acceptable salt thereof may be administered once daily. In embodiments, about 25 mg of glibornuride or a pharmaceutically acceptable salt thereof may be administered once daily. In embodiments, about 30 mg of glibornuride or a pharmaceutically acceptable salt thereof may be administered once daily. In embodiments, about 35 mg of glibornuride or a pharmaceutically acceptable salt thereof may be administered once daily. In embodiments, about 40 mg of glibornuride or a pharmaceutically acceptable salt thereof may be administered once daily. In embodiments, about 45 mg of glibornuride or a pharmaceutically acceptable salt thereof may be administered once daily. In embodiments, about 50 mg of glibornuride or a pharmaceutically acceptable salt thereof may be administered once daily. In embodiments, about 55 mg of glibornuride or a pharmaceutically acceptable salt thereof may be administered once daily. In embodiments, about 60 mg of glibornuride or a pharmaceutically acceptable salt thereof may be administered once daily. In embodiments, about 65 mg of glibornuride or a pharmaceutically acceptable salt thereof may be administered once daily. In embodiments, about 70 mg of glibornuride or a pharmaceutically acceptable salt thereof may be administered once daily. In embodiments, about 75 mg of glibornuride or a pharmaceutically acceptable salt thereof may be administered once daily.

In embodiments, the patient is administered 1.0 mg to 25 mg, 5 mg to 10 mg, 5 mg to 25 mg, 5 mg to 20 mg, 10 mg to 15 mg, 10 mg to 20 mg, 10 mg to 25 mg, 12.5 mg to 15 mg, 12.5 mg to 20 mg, 12.5 mg to 25 mg, 12.5 mg to 30 mg, 12.5 mg to 35 mg, 15 mg to 20 mg, 15 mg to 25 mg, 20 mg to 25 mg, or 25 mg to 30 mg, 30 mg to 35 mg, 35 mg to 40 mg, 45 mg to 50 mg, or 55 mg to 60 mg, or 70 mg to 75 mg glibornuride or a pharmaceutically acceptable salt thereof.

In embodiments, the patient is administered 1 mg, 5 mg, 10 mg, 12 mg, 12.5 mg, 15 mg, 17 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg glibornuride or a pharmaceutically acceptable salt thereof.

In embodiments methods of treating a metabolic disorder such as type 1 diabetes, type 2 diabetes or pre-diabetes include administering to a patient in need thereof a pharmaceutical composition including gaboxadol or a pharmaceutically acceptable salt thereof in combination with about 1 mg to about 75 mg glibornuride or a pharmaceutically acceptable salt thereof. In embodiments methods of treating a metabolic disorder such as type 1 diabetes, type 2 diabetes or pre-diabetes include administering to a patient in need thereof a pharmaceutical composition including gaboxadol or a pharmaceutically acceptable salt thereof in combination with about 12.5 mg to about 75 mg glibornuride or a pharmaceutically acceptable salt thereof.

In embodiments, the compositions include 1.0 mg to 10 mg, 1 mg to 12.5 mg, 1.0 mg to 15 mg, 1.0 mg to 25 mg, 1 mg to 30 mg, 1.0 mg to 35 mg, 1.0 mg to 40 mg, 1.0 mg to 45 mg, 1.0 mg to 50 mg, 1.0 mg to 55 mg, 1.0 mg to 60 mg, 5 mg to 10 mg, 5 mg to 20 mg, 5 mg to 25 mg, 5 mg to 30 mg, 5 mg to 35 mg, 5 mg to 40 mg, 5 mg to 45 mg, 5 mg to 50 mg, 5 mg to 55 mg, 5 mg to 60 mg, 10 mg to 15 mg, 15 mg to 20 mg, 20 mg to 25 mg, 25 mg to 30 mg, 25 mg to 35 mg, 25 mg to 40 mg, 25 mg to 45 mg, 25 mg to 50 mg, 25 mg to 55 mg, 30 mg to 35 mg, 30 mg to 40 mg, 35 mg to 45 mg, 35 mg to 40 mg, 35 mg to 45 mg, 35 mg to 50 mg, 35 mg to 55 mg, 35 mg to 60 mg, 40 mg to 45 mg, 40 mg to 50 mg, 40 mg to 55 mg, 40 mg to 60 mg, 45 mg to 50 mg, 45 mg to 55 mg, 45 mg to 60 mg, 50 mg to 55 mg, 50 mg to 60 mg, 55 mg to 60 mg, 65 mg to 70 mg, 70 mg to 75 mg, glibornuride or a pharmaceutically acceptable salt thereof.

In embodiments, the compositions include 5 mg, 10 mg, 12.5 mg, 15 mg, 20 mg, 25 mg, 30 mg, 35 mg, 40 mg, 45 mg, 50 mg, 55 mg, or 60 mg glibornuride or a pharmaceutically acceptable salt thereof.

In embodiments, methods of treating a metabolic disorder such as type 1 diabetes, type 2 diabetes or pre-diabetes include, administering to a patient in need thereof gaboxadol or a pharmaceutically acceptable salt thereof in combination with about 10 mg to about 400 mg gliclazide or a pharmaceutically acceptable salt thereof.

In embodiments, about 10 mg to about 400 mg of gliclazide or a pharmaceutically acceptable salt thereof may be administered in 24 hours. In embodiments, about 50 mg to about 500 mg of gliclazide or a pharmaceutically acceptable salt thereof may be administered in 24 hours. In embodiments, about 75 mg to about 400 mg of gliclazide or a pharmaceutically acceptable salt thereof may be administered in 24 hours. In embodiments, about 100 mg to about 375 mg of gliclazide or a pharmaceutically acceptable salt thereof may be administered in 24 hours. In embodiments, about 125 mg to about 350 mg of gliclazide or a pharmaceutically acceptable salt thereof may be administered in 24 hours. In embodiments, about 150 mg to about 325 mg of gliclazide or a pharmaceutically acceptable salt thereof may be administered in 24 hours. In embodiments, about 200 mg to about 300 mg of gliclazide or a pharmaceutically acceptable salt thereof may be administered in 24 hours.

In embodiments, the total daily dose may vary from 10 to 320 mg. The dose should be adjusted according to the individual's response, commencing with 10 to 80 mg daily and increasing until adequate control is achieved. A single dose should not exceed 160 mg. When higher doses are required, gliclazide should be taken twice daily and according to the main meals of the day.

In embodiments, about 10 mg, 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, or 320 mg of gliclazide or a pharmaceutically acceptable salt thereof may be administered in 24 hours. In embodiments, about 40 mg of gliclazide or a pharmaceutically acceptable salt thereof may be administered in 24 hours. In embodiments, about 80 mg of gliclazide or a pharmaceutically acceptable salt thereof may be administered in 24 hours. In embodiments, about 60 mg of gliclazide or a pharmaceutically acceptable salt thereof may be administered in 24 hours. In embodiments, about 120 mg of gliclazide or a pharmaceutically acceptable salt thereof may be administered in 24 hours. In embodiments, about 100 mg of gliclazide or a pharmaceutically acceptable salt thereof may be administered in 24 hours. In embodiments, about 30 mg of gliclazide or a pharmaceutically acceptable salt thereof may be administered in 24 hours. In embodiments, about 160 mg of gliclazide or a pharmaceutically acceptable salt thereof may be administered in 24 hours. In embodiments, about 240 mg of gliclazide or a pharmaceutically acceptable salt thereof may be administered in 24 hours. In embodiments, the gliclazide or a pharmaceutically acceptable salt thereof may be administered in divided doses over 24 hours, e.g., 160 mg twice daily. In embodiments, gliclazide may be administered once a day, e.g. 160 mg.

In embodiments, the patient is administered 10 mg to 15 mg, 15 mg to 20 mg, 20 mg to 25 mg, 25 mg to 30 mg, 30 mg to 35 mg, 35 mg to 40 mg, 40 mg to 45 mg, 45 mg to 50 mg, 50 mg to 55 mg, 55 mg to 60 mg, 60 mg to 75 mg, 75 mg, to 80 mg, 80 mg to 85 mg, 85 mg to 90 mg, 90 mg to 95 mg, 95 mg to 100 mg, 100 mg to 110 mg, 110 mg to 115 mg, 115 mg to 120 mg, 125 mg to 130 mg, 130 mg to 135 mg, 135 mg to 140 mg, 140 mg to 145 mg, 145 mg to 150 mg, 150 mg to 155 mg, 155 mg to 160 mg, 160 mg, to 165 mg, 165 mg to 170 mg, 175 mg to 180 mg, 180 mg to 185 mg, 185 mg to 190 mg, 190 mg to 195 mg, 195 to 200 mg, 200 mg to 225 mg, 225 mg to 250 mg, 250 mg to 275 mg, 275 mg to 300 mg, or 300 mg to 325 mg, gliclazide or a pharmaceutically acceptable salt thereof.

In embodiments, the patient is administered 10 mg, 15 mg, 20 mg, 25 mg, 30 mg, 35 mg, 40 mg, 45 mg, 50 mg, 55 mg, 60 mg, 75 mg, 80 mg, 85 mg, 90 mg, 95 mg, 100 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 225 mg, 250 mg, 275 mg, 300 mg, or 325 mg, gliclazide or a pharmaceutically acceptable salt thereof.

In embodiments methods of treating a metabolic disorder such as type 1 diabetes, type 2 diabetes or pre-diabetes include administering to a patient in need thereof a pharmaceutical composition including gaboxadol or a pharmaceutically acceptable salt thereof in combination with gliclazide or a pharmaceutically acceptable salt thereof. In embodiments methods of treating a metabolic disorder such as type 1 diabetes, type 2 diabetes or pre-diabetes include administering to a patient in need thereof a pharmaceutical composition including, in addition to gaboxadol or a pharmaceutically acceptable salt thereof, about 10 mg to about 160 mg gliclazide or a pharmaceutically acceptable salt thereof. In embodiments, conventional release pharmaceutical compositions containing 40 to 80 mg gliclazide are provided. In embodiments, extended release pharmaceutical compositions containing 30 to 60 mg gliclazide are provided.

In embodiments, the compositions include 10 mg to 15 mg, 15 mg to 20 mg, 20 mg to 25 mg, 25 mg to 30 mg, 30 mg to 35 mg, 35 mg to 40 mg, 40 mg to 45 mg, 45 mg to 50 mg, 50 mg to 55 mg, 55 mg to 60 mg, 60 mg to 75 mg, 75 mg, to 80 mg, 80 mg to 85 mg, 85 mg to 90 mg, 90 mg to 95 mg, 95 mg to 100 mg, 100 mg to 110 mg, 110 mg to 115 mg, 115 mg to 120 mg, 125 mg to 130 mg, 130 mg to 135 mg, 135 mg to 140 mg, 140 mg to 145 mg, 145 mg to 150 mg, 150 mg to 155 mg, or 155 mg to 160 mg, gliclazide or a pharmaceutically acceptable salt thereof.

In embodiments, the compositions include 10 mg, 15 mg, 20 mg, 25 mg, 30 mg, 35 mg, 40 mg, 45 mg, 50 mg, 55 mg, 60 mg, 75 mg, 80 mg, 85 mg, 90 mg, 95 mg, 100 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, or 200 mg, gliclazide or a pharmaceutically acceptable salt thereof.

In embodiments, methods of treating a metabolic disorder such as type 1 diabetes, type 2 diabetes or pre-diabetes include, in addition to gaboxadol or a pharmaceutically acceptable salt thereof, administering to a patient in need thereof about 1 mg to about 40 mg glipizide or a pharmaceutically acceptable salt thereof. In embodiments, methods of treating a metabolic disorder such as type 1 diabetes, type 2 diabetes or pre-diabetes include administering to a patient in need thereof gaboxadol or a pharmaceutically acceptable salt thereof in combination with about 1 mg to about 40 mg glipizide or a pharmaceutically acceptable salt thereof.

In embodiments, about 1 mg to about 40 mg of glipizide or a pharmaceutically acceptable salt thereof may be administered once daily. In embodiments, about 2 mg to about 40 mg of glipizide or a pharmaceutically acceptable salt thereof may be administered once daily. In embodiments, about 3 mg to about 40 mg of glipizide or a pharmaceutically acceptable salt thereof may be administered once daily. In embodiments, about 4 mg to about 35 mg of glipizide or a pharmaceutically acceptable salt thereof may be administered once daily. In embodiments, about 5 mg to about 30 mg of glipizide or a pharmaceutically acceptable salt thereof may be administered once daily. In embodiments, about 6 mg to about 45 mg of glipizide or a pharmaceutically acceptable salt thereof may be administered once daily. In embodiments, about 7.0 mg to about 40 mg of glipizide or a pharmaceutically acceptable salt thereof may be administered once daily. In embodiments, about 8 mg to about 35 mg of glipizide or a pharmaceutically acceptable salt thereof may be administered once daily. In embodiments, about 10 mg to about 30 mg of glipizide or a pharmaceutically acceptable salt thereof may be administered once daily. In embodiments, about 5 mg to about 10 mg of glipizide or a pharmaceutically acceptable salt thereof may be administered once daily. In embodiments, about 5 mg to about 15 mg of glipizide or a pharmaceutically acceptable salt thereof may be administered once daily. In embodiments, about 5 mg to about 20 mg of glipizide or a pharmaceutically acceptable salt thereof may be administered once daily. In embodiments, about 10 mg to about 25 mg of glipizide or a pharmaceutically acceptable salt thereof may be administered once daily. In embodiments, about 10 mg to about 20 mg of glipizide or a pharmaceutically acceptable salt thereof may be administered once daily. In embodiments, about 10 mg to about 15 mg of glipizide or a pharmaceutically acceptable salt thereof may be administered once daily. In embodiments, about 15 mg to about 30 mg of glipizide or a pharmaceutically acceptable salt thereof may be administered once daily. In embodiments, about 15 mg to about 25 mg of glipizide or a pharmaceutically acceptable salt thereof may be administered once daily. In embodiments, about 15 mg to about 20 mg of taspoglutide or a pharmaceutically acceptable salt thereof may be administered once daily. In embodiments, about 5 mg of glipizide or a pharmaceutically acceptable salt thereof may be administered once daily. In embodiments, about 10 mg of glipizide or a pharmaceutically acceptable salt thereof may be administered once daily. In embodiments, about 15 mg of glipizide or a pharmaceutically acceptable salt thereof may be administered once daily. In embodiments, about 20 mg of glipizide or a pharmaceutically acceptable salt thereof may be administered once daily. In embodiments, about 25 mg of glipizide or a pharmaceutically acceptable salt thereof may be administered once daily. In embodiments, about 30 mg of glipizide or a pharmaceutically acceptable salt thereof may be administered once daily. In embodiments, about 35 mg of glipizide or a pharmaceutically acceptable salt thereof may be administered once daily. In embodiments, about 40 mg of glipizide or a pharmaceutically acceptable salt thereof may be administered once daily.

In embodiments, the patient is administered 1.0 mg to 25 mg, 5 mg to 10 mg, 5 mg to 15 mg, 5 mg to 20 mg, 10 mg to 15 mg, 10 mg to 20 mg, 10 mg to 25 mg, 15 mg to 20 mg, 15 mg to 25 mg, 20 mg to 25 mg, or 25 mg to 30 mg, 30 mg to 35 mg, or 35 mg to 40 mg, glipizide or a pharmaceutically acceptable salt thereof.

In embodiments, the patient is administered 1 mg, 2.5 mg, 5 mg, 10 mg, 12.5 mg, 15 mg, 17 mg, 20 mg, 25 mg, 30 mg, 35 mg, or 40 mg, glipizide or a pharmaceutically acceptable salt thereof.

In embodiments methods of treating a metabolic disorder such as type 1 diabetes, type 2 diabetes or pre-diabetes include, administering gaboxadol or a pharmaceutically acceptable salt thereof, to a patient in need thereof in combination with a pharmaceutical composition including about 1 mg to about 40 mg glipizide or a pharmaceutically acceptable salt thereof.

In embodiments, the compositions include 1.0 mg to 10 mg, 1.0 mg to 15 mg, 1.0 mg to 25 mg, 1 mg to 30 mg, 1.0 mg to 35 mg, 1.0 mg to 40 mg, 5 mg to 10 mg, 5 mg to 20 mg, 5 mg to 25 mg, 5 mg to 30 mg, 5 mg to 35 mg, 5 mg to 40 mg, 10 mg to 15 mg, 15 mg to 20 mg, 20 mg to 25 mg, 20 mg to 30 mg, 20 mg to 35 mg, 20 mg to 40 mg, 25 mg to 30 mg, 25 mg to 35 mg, 25 mg to 40 mg, 30 mg to 35 mg, 30 mg to 40 mg, 35 mg to 40 mg, glipizide or a pharmaceutically acceptable salt thereof.

In embodiments, the compositions include 2.5 mg, 5 mg, 10 mg, 15 mg, 20 mg, 25 mg, 30 mg, 35 mg, or 40 mg, glipizide or a pharmaceutically acceptable salt thereof. In embodiments, extended release pharmaceutical compositions 2.5 mg, 5 mg and 10 mg, glipizide or a pharmaceutically acceptable salt thereof.

In embodiments, methods of treating a metabolic disorder such as type 1 diabetes, type 2 diabetes or pre-diabetes include in addition to gaboxadol or a pharmaceutically acceptable salt thereof, administering to a patient in need thereof in combination with about 10 mg to about 200 mg gliquidone or a pharmaceutically acceptable salt thereof.

In embodiments, about 10 mg to about 200 mg of gliquidone or a pharmaceutically acceptable salt thereof may be administered in 24 hours. In embodiments, about 45 mg to about 60 mg of gliquidone or a pharmaceutically acceptable salt thereof may be administered in 24 hours. In embodiments, about 15 mg to about 60 mg of gliquidone or a pharmaceutically acceptable salt thereof may be administered in 24 hours. In embodiments, about 45 mg to about 75 mg of gliquidone or a pharmaceutically acceptable salt thereof may be administered in 24 hours. In embodiments, about 30 mg to about 45 mg of gliquidone or a pharmaceutically acceptable salt thereof may be administered in 24 hours. In embodiments, about 100 mg to about 200 mg of gliclazide or a pharmaceutically acceptable salt thereof may be administered in 24 hours. In embodiments, about 60 mg to about 90 mg of gliquidone or a pharmaceutically acceptable salt thereof may be administered in 24 hours. In embodiments, about 90 mg to about 120 mg of gliquidone or a pharmaceutically acceptable salt thereof may be administered in 24 hours. In embodiments, about 150 mg to about 180 mg of gliquidone or a pharmaceutically acceptable salt thereof may be administered in 24 hours.

In embodiments, the total daily dose of gliquidone or a pharmaceutically acceptable salt thereof may vary from 15 to 180 mg. The dose can be adjusted according to the individual's response, commencing, e.g., with 15 mg daily and increasing until adequate control is achieved, e.g., 45-60 mg daily in 2-3 divided doses. A single dose should not exceed 60 mg.

In embodiments, about 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 110 mg, 115 mg, 120 mg, 130 mg, 140 mg, 150 mg, 160 mg, 170 mg, or 180 mg, of gliquidone or a pharmaceutically acceptable salt thereof may be administered in 24 hours. In embodiments, about 15 mg of gliquidone or a pharmaceutically acceptable salt thereof may be administered in 24 hours. In embodiments, about 30 mg of gliquidone or a pharmaceutically acceptable salt thereof may be administered in 24 hours. In embodiments, about 45 mg of gliquidone or a pharmaceutically acceptable salt thereof may be administered in 24 hours. In embodiments, about 60 mg of gliquidone or a pharmaceutically acceptable salt thereof may be administered in 24 hours. In embodiments, about 75 mg of gliquidone or a pharmaceutically acceptable salt thereof may be administered in 24 hours. In embodiments, about 90 mg of gliquidone or a pharmaceutically acceptable salt thereof may be administered in 24 hours. In embodiments, about 120 mg of gliquidone or a pharmaceutically acceptable salt thereof may be administered in 24 hours. In embodiments, about 135 mg of gliquidone or a pharmaceutically acceptable salt thereof may be administered in 24 hours. In embodiments, about 150 mg of gliquidone or a pharmaceutically acceptable salt thereof may be administered in 24 hours. In embodiments, about 165 mg of gliquidone or a pharmaceutically acceptable salt thereof may be administered in 24 hours. In embodiments, about 180 mg of gliquidone or a pharmaceutically acceptable salt thereof may be administered in 24 hours. In embodiments, the gliquidone or a pharmaceutically acceptable salt thereof may be administered in divided doses over 24 hours, e.g., 60 mg twice daily or 30 mg three times daily. In embodiments, gliquidone may be administered once a day, e.g. 45 mg.

In embodiments, the patient is administered 15 mg to 20 mg, 20 mg to 25 mg, 25 mg to 30 mg, 30 mg to 35 mg, 35 mg to 40 mg, 40 mg to 45 mg, 45 mg to 50 mg, 50 mg to 55 mg, 55 mg to 60 mg, 60 mg to 75 mg, 75 mg, to 80 mg, 80 mg to 85 mg, 85 mg to 90 mg, 90 mg to 95 mg, 95 mg to 100 mg, 100 mg to 110 mg, 110 mg to 115 mg, 115 mg to 120 mg, 125 mg to 130 mg, 130 mg to 135 mg, 135 mg to 140 mg, 140 mg to 145 mg, 145 mg to 150 mg, 150 mg to 155 mg, 155 mg to 160 mg, 160 mg, to 165 mg, 165 mg to 170 mg, or 175 mg to 180 mg, gliquidone or a pharmaceutically acceptable salt thereof.

In embodiments, the patient is administered 15 mg, 20 mg, 25 mg, 30 mg, 35 mg, 40 mg, 45 mg, 50 mg, 55 mg, 60 mg, 75 mg, 80 mg, 85 mg, 90 mg, 95 mg, 100 mg, 110 mg, 115 mg, 120 mg, 125 mg, 130 mg, 135 mg, 140 mg, 145 mg, 150 mg, 155 mg, 160 mg, 165 mg, 170 mg, 175 mg, or 180 mg, gliquidone or a pharmaceutically acceptable salt thereof.

In embodiments methods of treating a metabolic disorder such as type 1 diabetes, type 2 diabetes or pre-diabetes include administering to a patient in need thereof gaboxadol or a pharmaceutically acceptable salt thereof, in combination with a pharmaceutical composition including about 15 mg to about 180 mg gliquidone or a pharmaceutically acceptable salt thereof. In embodiments, conventional release pharmaceutical compositions containing 15 mg to 180 mg gliquidone are provided.

In embodiments, the compositions include 15 mg to 20 mg, 20 mg to 25 mg, 25 mg to 30 mg, 30 mg to 35 mg, 35 mg to 40 mg, 40 mg to 45 mg, 45 mg to 50 mg, 50 mg to 55 mg, 55 mg to 60 mg, 60 mg to 75 mg, 75 mg, to 80 mg, 80 mg to 85 mg, 85 mg to 90 mg, 90 mg to 95 mg, 95 mg to 100 mg, 100 mg to 110 mg, 110 mg to 115 mg, 115 mg to 120 mg, 125 mg to 130 mg, 130 mg to 135 mg, 135 mg to 140 mg, 140 mg to 145 mg, 145 mg to 150 mg, 150 mg to 155 mg, or 155 mg to 160 mg, gliquidone or a pharmaceutically acceptable salt thereof.

In embodiments, the compositions include 10 mg, 15 mg, 20 mg, 25 mg, 30 mg, 35 mg, 40 mg, 45 mg, 50 mg, 55 mg, 60 mg, 75 mg, 80 mg, 85 mg, 90 mg, 95 mg, 100 mg, 110 mg, 115 mg, 120 mg, 125 mg, 130 mg, 135 mg, 140 mg, 145 mg, 150 mg, 155 mg, or 160 mg, gliquidone or a pharmaceutically acceptable salt thereof.

In embodiments, methods of treating a metabolic disorder such as type 1 diabetes, type 2 diabetes or pre-diabetes include in addition to gaboxadol or a pharmaceutically acceptable salt thereof, administering to a patient in need thereof in combination with about 1 mg to about 16 mg glisoxepide or a pharmaceutically acceptable salt thereof. In embodiments, methods of treating a metabolic disorder such as type 1 diabetes, type 2 diabetes or pre-diabetes include in addition to gaboxadol or a pharmaceutically acceptable salt thereof, administering to a patient in need thereof in combination with glisoxepide or a pharmaceutically acceptable salt thereof.

In embodiments, about 1 mg to about 16 mg of glisoxepide or a pharmaceutically acceptable salt thereof may be administered in 24 hours. In embodiments, about 1 mg to about 10 mg of glisoxepide or a pharmaceutically acceptable salt thereof may be administered in 24 hours. In embodiments, about 1 mg to about 5 mg of glisoxepide or a pharmaceutically acceptable salt thereof may be administered in 24 hours. In embodiments, about 2 mg to about 10 mg of glisoxepide or a pharmaceutically acceptable salt thereof may be administered in 24 hours. In embodiments, about 3 mg to about 10 mg of glisoxepide or a pharmaceutically acceptable salt thereof may be administered in 24 hours. In embodiments, about 10 mg to about 16 mg of glisoxepide or a pharmaceutically acceptable salt thereof may be administered in 24 hours. In embodiments, about 5 mg to about 10 mg of glisoxepide or a pharmaceutically acceptable salt thereof may be administered in 24 hours.

In embodiments, the glisoxepide or a pharmaceutically acceptable salt thereof may be administered in divided doses over 24 hours, e.g., 5 mg twice daily. In embodiments, glisoxepide may be administered once a day.

In embodiments, the patient is administered 2 mg to 4 mg, 3 mg to 5 mg, 4 mg to 6 mg, 5 mg to 7 mg, 6 mg to 8 mg, 7 mg to 9 mg, 8 mg to 10 mg, 9 mg to 11 mg, 10 mg to 12 mg, 11 mg to 13 mg, 12 mg, to 14 mg, 13 mg to 15 mg, or 14 mg to 16 mg, glisoxepide or a pharmaceutically acceptable salt thereof.

In embodiments, the patient is administered 1 mg, 2 mg, 3 mg, 4 mg, 5 mg, 6 mg, 7 mg, 8 mg, 9 mg, 10 mg, 11 mg, 12 mg, 13 mg, 14 mg, 16 mg, or 16 mg, glisoxepide or a pharmaceutically acceptable salt thereof.

In embodiments methods of treating a metabolic disorder such as type 1 diabetes, type 2 diabetes or pre-diabetes include administering to a patient in need thereof gaboxadol or a pharmaceutically acceptable salt thereof, in combination with a pharmaceutical composition including about 1 mg to about 16 mg glisoxepide or a pharmaceutically acceptable salt thereof.

In embodiments, the compositions include 1 mg to 16 mg, 2 mg to 14 mg, 3 mg to 12 mg, 4 mg to 10 mg, 5 mg to 8 mg, 6 mg to 7 mg, 2 mg to 4 mg, 3 mg to 5 mg, 4 mg to 6 mg, 5 mg to 7 mg, 6 mg to 8 mg, 7 mg to 9 mg, 8 mg to 10 mg, 9 mg to 11 mg, 10 mg to 12 mg, 11 mg to 13 mg, 12 mg, to 14 mg, 13 mg to 15 mg, or 14 mg to 16 mg, glisoxepide or a pharmaceutically acceptable salt thereof.

In embodiments, the compositions include 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, or 16 mg, glisoxepide or a pharmaceutically acceptable salt thereof.

In embodiments, methods of treating a metabolic disorder such as type 1 diabetes, type 2 diabetes or pre-diabetes include administering to a patient in need thereof gaboxadol or a pharmaceutically acceptable salt thereof, in combination with about 0.5 mg to about 10 mg glimepiride or a pharmaceutically acceptable salt thereof.

In embodiments, about 0.5 mg to about 10 mg of glimepiride or a pharmaceutically acceptable salt thereof may be administered in 24 hours. In embodiments, about 0.75 mg to about 9 mg of glimepiride or a pharmaceutically acceptable salt thereof may be administered in 24 hours. In embodiments, about 1 mg to about 8 mg of glimepiride or a pharmaceutically acceptable salt thereof may be administered in 24 hours. In embodiments, about 1.25 mg to about 7 mg of glimepiride or a pharmaceutically acceptable salt thereof may be administered in 24 hours. In embodiments, about 1.5 mg to about 6 mg of glimepiride or a pharmaceutically acceptable salt thereof may be administered in 24 hours. In embodiments, about 1.75 mg to about 8 mg of glimepiride or a pharmaceutically acceptable salt thereof may be administered in 24 hours. In embodiments, about 2 mg to about 8 mg of glimepiride or a pharmaceutically acceptable salt thereof may be administered in 24 hours. In embodiments, about 2.5 mg to about 8 mg of glimepiride or a pharmaceutically acceptable salt thereof may be administered in 24 hours. In embodiments, about 3 mg to about 8 mg of glimepiride or a pharmaceutically acceptable salt thereof may be administered in 24 hours. In embodiments, about 4 mg to about 8 mg of glimepiride or a pharmaceutically acceptable salt thereof may be administered in 24 hours. In embodiments, about 5 mg to about 8 mg of glimepiride or a pharmaceutically acceptable salt thereof may be administered in 24 hours. In embodiments, about 6 mg to about 8 mg of glimepiride or a pharmaceutically acceptable salt thereof may be administered in 24 hours. In embodiments, about 7 mg to about 8 mg of glimepiride or a pharmaceutically acceptable salt thereof may be administered in 24 hours. In embodiments, about 6 mg to about 10 mg of glimepiride or a pharmaceutically acceptable salt thereof may be administered in 24 hours.

In embodiments, the glisoxepide or a pharmaceutically acceptable salt thereof may be administered in divided doses over 24 hours, e.g., 2 or 4 mg twice daily, e.g. before meals. In embodiments, glisoxepide may be administered once a day.

In embodiments, the patient is administered 0.5 mg to 0.75 mg, 0.5 mg to 1 mg, 1 mg to 2 mg, 2 mg to 3 mg, 3 mg to 4 mg, 4 mg to 5 mg, 5 mg to 6 mg, 6 mg 7 mg, 7 mg to 8 mg, 8 mg to 9 mg, or 9 mg to 10 mg, glimepiride or a pharmaceutically acceptable salt thereof.

In embodiments, the patient is administered 0.5 mg, 0.75 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, or 10 mg, glimepiride or a pharmaceutically acceptable salt thereof.

In embodiments methods of treating a metabolic disorder such as type 1 diabetes, type 2 diabetes or pre-diabetes include administering to a patient in need thereof gaboxadol or a pharmaceutically acceptable salt thereof, in combination with a pharmaceutical composition including about 0.5 mg to about 10 mg glimepiride or a pharmaceutically acceptable salt thereof.

In embodiments, the compositions include 0.5 mg to 10 mg, 0.75 mg to 10 mg, 1 mg to 10 mg, 1.5 mg to 8.5 mg, 2 mg to 8 mg, 2.5 mg to 8 mg, 3 mg to 8 mg, 4 mg to 7 mg, 2 mg to 4 mg, 3 mg to 5 mg, 4 mg to 6 mg, 5 mg to 7 mg, 6 mg to 8 mg, 7 mg to 9 mg, 8 mg to 10 mg, or 9 mg to 10 mg, glimepiride or a pharmaceutically acceptable salt thereof.

In embodiments, the compositions include 0.5 mg, 0.75 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, or 10 mg, glimepiride or a pharmaceutically acceptable salt thereof.

In embodiments, a patient in need thereof is administered gaboxadol or a pharmaceutically acceptable salt thereof in combination with a thiazolidinedione (TZD) or a pharmaceutically acceptable salt thereof. In embodiments a patient in need thereof is administered a pharmaceutical composition including gaboxadol or a pharmaceutically acceptable salt thereof in combination with a thiazolidinedione or a pharmaceutically acceptable salt thereof. Examples of thiazolidinediones include pioglitazone, rosiglitazone and lobeglitazone.

In embodiments, methods of treating a metabolic disorder such as type 1 diabetes, type 2 diabetes or pre-diabetes include administering to a patient in need thereof gaboxadol or a pharmaceutically acceptable salt thereof, in combination with about 5 mg to about 60 mg pioglitazone or a pharmaceutically acceptable salt thereof.

In embodiments, about 5 mg to about 60 mg of pioglitazone or a pharmaceutically acceptable salt thereof may be administered once daily. In embodiments, about 10 mg to about 60 mg of pioglitazone or a pharmaceutically acceptable salt thereof may be administered once daily. In embodiments, about 15 mg to about 30 mg of pioglitazone or a pharmaceutically acceptable salt thereof may be administered once daily. In embodiments, about 15 mg to about 45 mg of pioglitazone or a pharmaceutically acceptable salt thereof may be administered once daily. In embodiments, about 15 mg to about 50 mg of pioglitazone or a pharmaceutically acceptable salt thereof may be administered once daily. In embodiments, about 10 mg to about 45 mg of pioglitazone or a pharmaceutically acceptable salt thereof may be administered once daily. In embodiments, about 10 mg to about 40 mg of pioglitazone or a pharmaceutically acceptable salt thereof may be administered once daily. In embodiments, about 15 mg to about 30 mg of pioglitazone or a pharmaceutically acceptable salt thereof may be administered once daily. In embodiments, about 10 mg to about 30 mg of pioglitazone or a pharmaceutically acceptable salt thereof may be administered once daily. In embodiments, about 10 mg to about 25 mg of pioglitazone or a pharmaceutically acceptable salt thereof may be administered once daily. In embodiments, about 10 mg to about 20 mg of pioglitazone or a pharmaceutically acceptable salt thereof may be administered once daily. In embodiments, about 10 mg to about 15 mg of pioglitazone or a pharmaceutically acceptable salt thereof may be administered once daily. In embodiments, about 5 mg to about 30 mg of pioglitazone or a pharmaceutically acceptable salt thereof may be administered once daily. In embodiments, about 5 mg to about 45 mg of pioglitazone or a pharmaceutically acceptable salt thereof may be administered once daily. In embodiments, about 5 mg to about 50 mg of pioglitazone or a pharmaceutically acceptable salt thereof may be administered once daily. In embodiments, about 5 mg to about 30 mg of pioglitazone or a pharmaceutically acceptable salt thereof may be administered once daily. In embodiments, about 5 mg to about 35 mg of pioglitazone or a pharmaceutically acceptable salt thereof may be administered once daily. In embodiments, about 5 mg of pioglitazone or a pharmaceutically acceptable salt thereof may be administered once daily. In embodiments, about 10 mg of pioglitazone or a pharmaceutically acceptable salt thereof may be administered once daily. In embodiments, about 15 mg of pioglitazone or a pharmaceutically acceptable salt thereof may be administered once daily. In embodiments, about 20 mg of pioglitazone or a pharmaceutically acceptable salt thereof may be administered once daily. In embodiments, about 25 mg of pioglitazone or a pharmaceutically acceptable salt thereof may be administered once daily. In embodiments, about 30 mg of pioglitazone or a pharmaceutically acceptable salt thereof may be administered once daily. In embodiments, about 35 mg of pioglitazone or a pharmaceutically acceptable salt thereof may be administered once daily. In embodiments, about 40 mg of pioglitazone or a pharmaceutically acceptable salt thereof may be administered once daily. In embodiments, about 45 mg of pioglitazone or a pharmaceutically acceptable salt thereof may be administered once daily. In embodiments, about 50 mg of pioglitazone or a pharmaceutically acceptable salt thereof may be administered once daily. In embodiments, about 55 mg of pioglitazone or a pharmaceutically acceptable salt thereof may be administered once daily. In embodiments, about 60 mg of pioglitazone or a pharmaceutically acceptable salt thereof may be administered once daily. In embodiments, the pioglitazone or a pharmaceutically acceptable salt thereof may be administered in divided doses over 24 hours, e.g., 15 mg or 30 mg twice daily, e.g. before a meal. In embodiments, pioglitazone may be administered once a day.

In embodiments, the patient is administered 5 mg to 10 mg, 5 mg to 15 mg, 5 mg to 20 mg, 5 mg to 25 mg, 5 mg to 30 mg, 5 mg to 35 mg, 5 mg to 40 mg, 5 mg to 45 mg, 5 mg to 50 mg, 5 mg to 55 mg, 5 mg to 60 mg, 10 mg to 15 mg, 10 mg to 20 mg, 10 mg to 25 mg, 10 mg to 30 mg, 10 mg to 35 mg, 10 mg to 40 mg, 10 mg to 45 mg, 10 mg to 50 mg, 15 mg to 20 mg, 15 mg to 25 mg, 15 mg to 30 mg, 15 mg to 40 mg, 15 mg to 45 mg, 15 mg to 50 mg, 15 mg to 60 mg, 20 mg to 25 mg, 25 mg to 30 mg, 30 mg to 35 mg, 35 mg to 40 mg, 45 mg to 50 mg, or 55 mg to 60 mg, pioglitazone or a pharmaceutically acceptable salt thereof.

In embodiments, the patient is administered 5 mg, 7.5 mg, 10 mg, 12.5 mg, 15 mg, 17.5 mg, 20 mg, 25 mg, 30 mg, 35 mg, 40 mg, 45 mg, 50 mg, 55 mg, or 60 mg pioglitazone or a pharmaceutically acceptable salt thereof.

In embodiments methods of treating a metabolic disorder such as type 1 diabetes, type 2 diabetes or pre-diabetes include administering to a patient in need thereof gaboxadol or a pharmaceutically acceptable salt thereof, in combination with a pharmaceutical composition including about 1 mg to about 60 mg pioglitazone or a pharmaceutically acceptable salt thereof.

In embodiments, the compositions include 5 mg to 10 mg, 5 mg to 15 mg, 5 mg to 20 mg, 5 mg to 25 mg, 5 mg to 30 mg, 5 mg to 35 mg, 5 mg to 40 mg, 5 mg to 45 mg, 5 mg to 50 mg, 5 mg to 55 mg, 5 mg to 60 mg, 10 mg to 15 mg, 10 mg to 20 mg, 10 mg to 25 mg, 10 mg to 30 mg, 10 mg to 35 mg, 10 mg to 40 mg, 10 mg to 45 mg, 10 mg to 50 mg, 15 mg to 20 mg, 15 mg to 25 mg, 15 mg to 30 mg, 15 mg to 40 mg, 15 mg to 45 mg, 15 mg to 50 mg, 15 mg to 60 mg, 20 mg to 25 mg, 25 mg to 30 mg, 30 mg to 35 mg, 35 mg to 40 mg, 45 mg to 50 mg, or 55 mg to 60 mg, pioglitazone or a pharmaceutically acceptable salt thereof.

In embodiments, the compositions include 5 mg, 10 mg, 15 mg, 20 mg, 25 mg, 30 mg, 35 mg, 40 mg, 45 mg, 50 mg, 55 mg, or 60 mg pioglitazone or a pharmaceutically acceptable salt thereof.

In embodiments, methods of treating a metabolic disorder such as type 1 diabetes, type 2 diabetes or pre-diabetes include administering to a patient in need thereof gaboxadol or a pharmaceutically acceptable salt thereof, in combination with about 0.5 mg to about 10 mg rosiglitazone or a pharmaceutically acceptable salt thereof.

In embodiments, about 0.5 mg to about 10 mg of rosiglitazone or a pharmaceutically acceptable salt thereof may be administered in 24 hours. In embodiments, about 0.75 mg to about 9 mg of rosiglitazone or a pharmaceutically acceptable salt thereof may be administered in 24 hours. In embodiments, about 1 mg to about 8 mg of rosiglitazone or a pharmaceutically acceptable salt thereof may be administered in 24 hours. In embodiments, about 1.25 mg to about 7 mg of rosiglitazone or a pharmaceutically acceptable salt thereof may be administered in 24 hours. In embodiments, about 1.5 mg to about 6 mg of rosiglitazone or a pharmaceutically acceptable salt thereof may be administered in 24 hours. In embodiments, about 1.75 mg to about 8 mg of rosiglitazone or a pharmaceutically acceptable salt thereof may be administered in 24 hours. In embodiments, about 2 mg to about 8 mg of rosiglitazone or a pharmaceutically acceptable salt thereof may be administered in 24 hours. In embodiments, about 2.5 mg to about 8 mg of rosiglitazone or a pharmaceutically acceptable salt thereof may be administered in 24 hours. In embodiments, about 3 mg to about 8 mg of rosiglitazone or a pharmaceutically acceptable salt thereof may be administered in 24 hours. In embodiments, about 4 mg to about 8 mg of rosiglitazone or a pharmaceutically acceptable salt thereof may be administered in 24 hours. In embodiments, about 5 mg to about 8 mg of rosiglitazone or a pharmaceutically acceptable salt thereof may be administered in 24 hours. In embodiments, about 6 mg to about 8 mg of rosiglitazone or a pharmaceutically acceptable salt thereof may be administered in 24 hours. In embodiments, about 7 mg to about 8 mg of rosiglitazone or a pharmaceutically acceptable salt thereof may be administered in 24 hours. In embodiments, about 6 mg to about 10 mg of rosiglitazone or a pharmaceutically acceptable salt thereof may be administered in 24 hours.

In embodiments, the rosiglitazone or a pharmaceutically acceptable salt thereof may be administered in divided doses over 24 hours, e.g., 2 or 4 mg twice daily. In embodiments, rosiglitazone may be administered once a day.

In embodiments, the patient is administered 0.5 mg to 0.75 mg, 0.5 mg to 1 mg, 1 mg to 2 mg, 2 mg to 3 mg, 3 mg to 4 mg, 4 mg to 5 mg, 5 mg to 6 mg, 6 mg 7 mg, 7 mg to 8 mg, 8 mg to 9 mg, or 9 mg to 10 mg, rosiglitazone or a pharmaceutically acceptable salt thereof.

In embodiments, the patient is administered 0.5 mg, 0.75 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, or 10 mg, rosiglitazone or a pharmaceutically acceptable salt thereof.

In embodiments methods of treating a metabolic disorder such as type 1 diabetes, type 2 diabetes or pre-diabetes include administering to a patient in need thereof gaboxadol or a pharmaceutically acceptable salt thereof, in combination with a pharmaceutical composition including, about 0.5 mg to about 10 mg rosiglitazone or a pharmaceutically acceptable salt thereof.

In embodiments, the compositions include 0.5 mg to 10 mg, 0.75 mg to 10 mg, 1 mg to 10 mg, 1.5 mg to 8.5 mg, 2 mg to 8 mg, 2.5 mg to 8 mg, 3 mg to 8 mg, 4 mg to 7 mg, 2 mg to 4 mg, 3 mg to 5 mg, 4 mg to 6 mg, 5 mg to 7 mg, 6 mg to 8 mg, 7 mg to 9 mg, 8 mg to 10 mg, or 9 mg to 10 mg, rosiglitazone or a pharmaceutically acceptable salt thereof.

In embodiments, the compositions include 0.5 mg, 0.75 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, or 10 mg, rosiglitazone or a pharmaceutically acceptable salt thereof.

In embodiments, methods of treating a metabolic disorder such as type 1 diabetes, type 2 diabetes or pre-diabetes herein include, in addition to gaboxadol or a pharmaceutically acceptable salt thereof, administering to a patient in need thereof about 0.1 mg to about 5 mg lobeglitazone or a pharmaceutically acceptable salt thereof. In embodiments, methods of treating a metabolic disorder such as type 1 diabetes, type 2 diabetes or pre-diabetes herein include administering to a patient in need thereof gaboxadol or a pharmaceutically acceptable salt thereof, in combination with about 0.1 mg to about 5 mg lobeglitazone or a pharmaceutically acceptable salt thereof.

In embodiments, about 0.2 mg to about 5 mg of lobeglitazone or a pharmaceutically acceptable salt thereof may be administered in 24 hours. In embodiments, about 0.3 mg to about 5 mg of lobeglitazone or a pharmaceutically acceptable salt thereof may be administered in 24 hours. In embodiments, about 0.4 mg to about 5 mg of lobeglitazone or a pharmaceutically acceptable salt thereof may be administered in 24 hours. In embodiments, about 0.5 mg to about 5 mg of lobeglitazone or a pharmaceutically acceptable salt thereof may be administered in 24 hours. In embodiments, about 0.6 mg to about 5 mg of lobeglitazone or a pharmaceutically acceptable salt thereof may be administered in 24 hours. In embodiments, about 0.7 mg to about 5 mg of lobeglitazone or a pharmaceutically acceptable salt thereof may be administered in 24 hours. In embodiments, about 0.8 mg to about 5 mg of lobeglitazone or a pharmaceutically acceptable salt thereof may be administered in 24 hours. In embodiments, about 0.9 mg to about 5 mg of lobeglitazone or a pharmaceutically acceptable salt thereof may be administered in 24 hours. In embodiments, about 1 mg to about 5 mg of lobeglitazone or a pharmaceutically acceptable salt thereof may be administered in 24 hours. In embodiments, about 1.25 mg to about 5 mg of lobeglitazone or a pharmaceutically acceptable salt thereof may be administered in 24 hours. In embodiments, about 1.5 mg to about 5 mg of lobeglitazone or a pharmaceutically acceptable salt thereof may be administered in 24 hours. In embodiments, about 1.75 mg to about 5 mg of lobeglitazone or a pharmaceutically acceptable salt thereof may be administered in 24 hours. In embodiments, about 2 mg to about 5 mg of lobeglitazone or a pharmaceutically acceptable salt thereof may be administered in 24 hours. In embodiments, about 2.25 mg to about 5 mg of lobeglitazone or a pharmaceutically acceptable salt thereof may be administered in 24 hours. In embodiments, about 2.5 mg to about 5 mg of lobeglitazone or a pharmaceutically acceptable salt thereof may be administered in 24 hours. In embodiments, about 2.75 mg to about 5 mg of lobeglitazone or a pharmaceutically acceptable salt thereof may be administered in 24 hours. In embodiments, about 3 mg to about 5 mg of lobeglitazone or a pharmaceutically acceptable salt thereof may be administered in 24 hours. In embodiments, about 3.25 mg to about 5 mg of lobeglitazone or a pharmaceutically acceptable salt thereof may be administered in 24 hours. In embodiments, about 3.5 mg to about 5 mg of lobeglitazone or a pharmaceutically acceptable salt thereof may be administered in 24 hours. In embodiments, about 3.75 mg to about 5 mg of lobeglitazone or a pharmaceutically acceptable salt thereof may be administered in 24 hours. In embodiments, about 4 mg to about 5 mg of lobeglitazone or a pharmaceutically acceptable salt thereof may be administered in 24 hours. In embodiments, about 4.25 mg to about 5 mg of lobeglitazone or a pharmaceutically acceptable salt thereof may be administered in 24 hours. In embodiments, about 4.5 mg to about 5 mg of lobeglitazone or a pharmaceutically acceptable salt thereof may be administered in 24 hours. In embodiments, about 4.75 mg to about 5 mg of lobeglitazone or a pharmaceutically acceptable salt thereof may be administered in 24 hours.

In embodiments, about 0.1 mg, 0.2 mg, 0.3 mg, 0.4 mg, 0.5 mg, 0.6 mg, 0.7 mg, 0.8 mg, 0.9 mg, 1 mg, 1.1 mg, 1.2 mg, 1.3 mg, 1.4 mg, 1.5 mg, 1.6 mg, 1.7 mg, 1.8 mg, 1.9 mg, 2 mg, 2.1 mg, 2.2 mg, 2.3 mg, 2.4 mg, 2.5 mg, 2.6 mg, 2.7 mg, 2.8 mg, 2.9 mg, 3 mg, 3.1 mg, 3.2 mg, 3.3 mg, 3.4 mg, 3.5 mg, 3.6 mg, 3.7 mg, 3.8 mg, 3.9 mg, 4 mg, 4.1 mg, 4.2 mg, 4.3 mg, 4.4 mg, 4.5 mg, 4.6 mg, 4.7 mg, 4.8 mg, 4.9 mg, or 5 mg, of lobeglitazone or a pharmaceutically acceptable salt thereof may be administered in 24 hours. In embodiments, about 0.5 mg of lobeglitazone or a pharmaceutically acceptable salt thereof may be administered in 24 hours. In embodiments, the lobeglitazone or a pharmaceutically acceptable salt thereof may be administered in divided doses over 24 hours, e.g., twice a day. In embodiments, lobeglitazone may be administered once a day.

In embodiments methods of treating a metabolic disorder such as type 1 diabetes, type 2 diabetes or pre-diabetes include administering to a patient in need thereof gaboxadol or a pharmaceutically acceptable salt thereof, in combination with a pharmaceutical composition including, about 0.1 mg to about 5 mg lobeglitazone or a pharmaceutically acceptable salt thereof.

In embodiments, the compositions include 0.1 mg to 5 mg, 0.2 mg to 5 mg, 0.3 mg to 0.5 mg, 0.4 mg to 5 mg, 0.5 mg to 5 mg, 0.6 mg to 5 mg, 0.7 mg to 5 mg, 0.75 mg to 5 mg, 0.8 mg to 5 mg, 0.9 mg to 5 mg, 1.0 mg to 5 mg, 1.1 mg to 5 mg, 1.2 mg to 5 mg, 1.25 mg to 5 mg, 1.3 mg to 5 mg, 1.4 mg to 5 mg, 1.5 mg to 5 mg, 1.6 mg to 5 mg, 1.7 mg to 5 mg, 1.75 mg to 5 mg, 1.8 mg to 5 mg, 1.9 mg to 5 mg, 2.0 mg to 5 mg, 2.25 mg to 5 mg, 2.5 mg to 5 mg, 2.75 to 5 mg, 3 mg to 5 mg, 3.5 mg to 5 mg, 4 mg to 5 mg, 4.5 mg, to 5 mg, 0.1 mg to 2.5 mg, 0.5 mg to 2.5 mg, 0.75 mg to 2.5 mg, 1.0 mg to 2.5 mg, 1.25 mg to 2.5 mg, 1.5 mg to 2.5 mg, 1.75 mg to 2.5 mg, or 2.0 mg to 2.5 mg of lobeglitazone or a pharmaceutically acceptable salt thereof. In embodiments, the compositions include 0.1 mg, 0.5 mg, 0.75 mg, 1 mg, 1.25 mg, 1.5 mg, 1.75 mg, 2 mg, 2.25 mg, 2.5 mg, 2.75 mg, 3 mg, 3.25 mg, 3.5 mg, 3.75 mg, 4 mg, 4.25 mg, 4.5 mg, 4.75 mg, or 5 mg, lobeglitazone or a pharmaceutically acceptable salt thereof.

In embodiments, a patient in need thereof is administered gaboxadol or a pharmaceutically acceptable salt thereof in combination with an alpha-glucosidase inhibitor or a pharmaceutically acceptable salt thereof. In embodiments a patient in need thereof is administered a pharmaceutical composition including gaboxadol or a pharmaceutically acceptable salt thereof in combination with an alpha-glucosidase inhibitor or a pharmaceutically acceptable salt thereof. Examples of alpha-glucosidase inhibitors include acarbose, miglitol and voglibose.

In embodiments, methods of treating a metabolic disorder such as type 1 diabetes, type 2 diabetes or pre-diabetes include in addition to gaboxadol or a pharmaceutically acceptable salt thereof, administering to a patient in need thereof about 5 mg to about 400 mg acarbose or a pharmaceutically acceptable salt thereof. In embodiments, methods of treating a metabolic disorder such as type 1 diabetes, type 2 diabetes or pre-diabetes include administering to a patient in need thereof gaboxadol or a pharmaceutically acceptable salt thereof, in combination with about 5 mg to about 400 mg acarbose or a pharmaceutically acceptable salt thereof.

In embodiments, about 5 mg to about 400 mg of acarbose or a pharmaceutically acceptable salt thereof may be administered in 24 hours. In embodiments, about 25 mg to about 400 mg of acarbose or a pharmaceutically acceptable salt thereof may be administered in 24 hours. In embodiments, about 50 mg to about 400 mg of acarbose or a pharmaceutically acceptable salt thereof may be administered in 24 hours. In embodiments, about 75 mg to about 400 mg of acarbose or a pharmaceutically acceptable salt thereof may be administered in 24 hours. In embodiments, about 100 mg to about 300 mg of acarbose or a pharmaceutically acceptable salt thereof may be administered in 24 hours. In embodiments, about 125 mg to about 300 mg of acarbose or a pharmaceutically acceptable salt thereof may be administered in 24 hours. In embodiments, about 150 mg to about 300 mg of acarbose or a pharmaceutically acceptable salt thereof may be administered in 24 hours. In embodiments, about 175 mg to about 300 mg of acarbose or a pharmaceutically acceptable salt thereof may be administered in 24 hours. In embodiments, about 200 mg to about 300 mg of acarbose or a pharmaceutically acceptable salt thereof may be administered in 24 hours.

In embodiments, the total daily dose may vary from 5 to 400 mg. The dose should be adjusted according to the individual's response, commencing, e.g., with 25 mg given once a day or 3 times daily and increasing until adequate control is achieved. A single dose should not exceed 300 mg. When higher doses are required, acarbose should be taken three times daily and according to the main meals of the day.

In embodiments, about 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 110 mg, 120 mg, 125 mg, 130 mg, 140 mg, 150 mg, 160 mg, 170 mg, 175 mg, 180 mg, 190 mg, 200 mg, 210 mg, 220 mg, 225 mg, 230 mg, 240 mg, 250 mg, 260 mg, 270 mg, 275 mg, 280 mg, 290 mg, 300 mg, 310 mg, 320 mg, 325 mg, 330 mg, 340 mg, mg, 350 mg, 375 mg or 400 mg of acarbose or a pharmaceutically acceptable salt thereof may be administered in 24 hours. In embodiments, about 25 mg of acarbose or a pharmaceutically acceptable salt thereof may be administered in 24 hours. In embodiments, about 50 mg of acarbose or a pharmaceutically acceptable salt thereof may be administered in 24 hours. In embodiments, about 75 mg of acarbose or a pharmaceutically acceptable salt thereof may be administered in 24 hours. In embodiments, about 100 mg of acarbose or a pharmaceutically acceptable salt thereof may be administered in 24 hours. In embodiments, about 125 mg of acarbose or a pharmaceutically acceptable salt thereof may be administered in 24 hours. In embodiments, about 150 mg of acarbose or a pharmaceutically acceptable salt thereof may be administered in 24 hours. In embodiments, about 175 mg of acarbose or a pharmaceutically acceptable salt thereof may be administered in 24 hours. In embodiments, about 200 mg of acarbose or a pharmaceutically acceptable salt thereof may be administered in 24 hours. In embodiments, the acarbose or a pharmaceutically acceptable salt thereof may be administered in divided doses over 24 hours, e.g., 25 mg, 50 mg, 75 mg or 100 mg three times daily. In embodiments, acarbose may be administered once a day, e.g. 100 mg.

In embodiments methods of treating a metabolic disorder such as type 1 diabetes, type 2 diabetes or pre-diabetes include administering to a patient in need thereof gaboxadol or a pharmaceutically acceptable salt thereof, in combination with a pharmaceutical composition including, about 5 mg to about 400 mg acarbose or a pharmaceutically acceptable salt thereof.

In embodiments, the patient is administered a pharmaceutical composition containing 5 mg to 10 mg, 10 mg to 15 mg, 15 mg to 20 mg, 20 mg to 25 mg, 25 mg to 30 mg, 30 mg to 35 mg, 35 mg to 40 mg, 40 mg to 45 mg, 45 mg to 50 mg, 50 mg to 55 mg, 55 mg to 60 mg, 60 mg to 75 mg, 75 mg, to 80 mg, 80 mg to 85 mg, 85 mg to 90 mg, 90 mg to 95 mg, 95 mg to 100 mg, 100 mg to 110 mg, 110 mg to 115 mg, 115 mg to 120 mg, 125 mg to 130 mg, 130 mg to 135 mg, 135 mg to 140 mg, 140 mg to 145 mg, 145 mg to 150 mg, 150 mg to 155 mg, 155 mg to 160 mg, 160 mg, to 165 mg, 165 mg to 170 mg, 175 mg to 180 mg, 180 mg to 185 mg, 185 mg to 190 mg, 190 mg to 195 mg, 195 to 200 mg, 200 mg to 225 mg, 225 mg to 250 mg, 250 mg to 275 mg, 275 mg to 300 mg, or 300 mg to 325 mg, 325 mg to 350 mg, 350 mg, to 375 mg, or 375 mg to 400 mg, acarbose or a pharmaceutically acceptable salt thereof.

In embodiments, the patient is administered a pharmaceutical composition containing 5 mg, 10 mg, 15 mg, 20 mg, 25 mg, 30 mg, 35 mg, 40 mg, 45 mg, 50 mg, 55 mg, 60 mg, 75 mg, 80 mg, 85 mg, 90 mg, 95 mg, 100 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 225 mg, 250 mg, 275 mg, or 300 mg, acarbose or a pharmaceutically acceptable salt thereof.

In embodiments, methods of treating a metabolic disorder such as type 1 diabetes, type 2 diabetes or pre-diabetes include administering to a patient in need thereof gaboxadol or a pharmaceutically acceptable salt thereof, in combination with about 5 mg to about 400 mg miglitol or a pharmaceutically acceptable salt thereof.

In embodiments, about 5 mg to about 400 mg of miglitol or a pharmaceutically acceptable salt thereof may be administered in 24 hours. In embodiments, about 25 mg to about 400 mg of miglitol or a pharmaceutically acceptable salt thereof may be administered in 24 hours. In embodiments, about 50 mg to about 400 mg of miglitol or a pharmaceutically acceptable salt thereof may be administered in 24 hours. In embodiments, about 75 mg to about 400 mg of miglitol or a pharmaceutically acceptable salt thereof may be administered in 24 hours. In embodiments, about 100 mg to about 300 mg of miglitol or a pharmaceutically acceptable salt thereof may be administered in 24 hours. In embodiments, about 125 mg to about 300 mg of miglitol or a pharmaceutically acceptable salt thereof may be administered in 24 hours. In embodiments, about 150 mg to about 300 mg of miglitol or a pharmaceutically acceptable salt thereof may be administered in 24 hours. In embodiments, about 175 mg to about 300 mg of miglitol or a pharmaceutically acceptable salt thereof may be administered in 24 hours. In embodiments, about 200 mg to about 300 mg of miglitol or a pharmaceutically acceptable salt thereof may be administered in 24 hours.

In embodiments, the total daily dose of miglitol or a pharmaceutically acceptable salt thereof may vary from 5 to 400 mg. The dose should be adjusted according to the individual's response, commencing, e.g., with 25 mg given once a day or 3 times daily and increasing until adequate control is achieved. A single dose should not exceed 300 mg. When higher doses are required, miglitol should be taken three times daily and according to the main meals of the day.

In embodiments, about 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 110 mg, 120 mg, 125 mg, 130 mg, 140 mg, 150 mg, 160 mg, 170 mg, 175 mg, 180 mg, 190 mg, 200 mg, 210 mg, 220 mg, 225 mg, 230 mg, 240 mg, 250 mg, 260 mg, 270 mg, 275 mg, 280 mg, 290 mg, 300 mg, 310 mg, 320 mg, 325 mg, 330 mg, 340 mg, mg, 350 mg, 375 mg or 400 mg of miglitol or a pharmaceutically acceptable salt thereof may be administered in 24 hours. In embodiments, about 25 mg of miglitol or a pharmaceutically acceptable salt thereof may be administered in 24 hours. In embodiments, about 50 mg of miglitol or a pharmaceutically acceptable salt thereof may be administered in 24 hours. In embodiments, about 75 mg of miglitol or a pharmaceutically acceptable salt thereof may be administered in 24 hours. In embodiments, about 100 mg of miglitol or a pharmaceutically acceptable salt thereof may be administered in 24 hours. In embodiments, about 125 mg of miglitol or a pharmaceutically acceptable salt thereof may be administered in 24 hours. In embodiments, about 150 mg of miglitol or a pharmaceutically acceptable salt thereof may be administered in 24 hours. In embodiments, about 175 mg of miglitol or a pharmaceutically acceptable salt thereof may be administered in 24 hours. In embodiments, about 200 mg of miglitol or a pharmaceutically acceptable salt thereof may be administered in 24 hours. In embodiments, the miglitol or a pharmaceutically acceptable salt thereof may be administered in divided doses over 24 hours, e.g., 25 mg, 50 mg, 75 mg or 100 mg three times daily. In embodiments, miglitol may be administered once a day, e.g. 100 mg.

In embodiments methods of treating a metabolic disorder such as type 1 diabetes, type 2 diabetes or pre-diabetes include administering to a patient in need thereof gaboxadol or a pharmaceutically acceptable salt thereof, in combination with a pharmaceutical composition including, about 5 mg to about 400 mg or a pharmaceutically acceptable salt thereof.

In embodiments, the patient is administered a pharmaceutical composition containing 5 mg to 10 mg, 10 mg to 15 mg, 15 mg to 20 mg, 20 mg to 25 mg, 25 mg to 30 mg, 30 mg to 35 mg, 35 mg to 40 mg, 40 mg to 45 mg, 45 mg to 50 mg, 50 mg to 55 mg, 55 mg to 60 mg, 60 mg to 75 mg, 75 mg, to 80 mg, 80 mg to 85 mg, 85 mg to 90 mg, 90 mg to 95 mg, 95 mg to 100 mg, 100 mg to 110 mg, 110 mg to 115 mg, 115 mg to 120 mg, 125 mg to 130 mg, 130 mg to 135 mg, 135 mg to 140 mg, 140 mg to 145 mg, 145 mg to 150 mg, 150 mg to 155 mg, 155 mg to 160 mg, 160 mg, to 165 mg, 165 mg to 170 mg, 175 mg to 180 mg, 180 mg to 185 mg, 185 mg to 190 mg, 190 mg to 195 mg, 195 to 200 mg, 200 mg to 225 mg, 225 mg to 250 mg, 250 mg to 275 mg, 275 mg to 300 mg, or 300 mg to 325 mg, 325 mg to 350 mg, 350 mg, to 375 mg, or 375 mg to 400 mg, miglitol or a pharmaceutically acceptable salt thereof.

In embodiments, the patient is administered a pharmaceutical composition containing 5 mg, 10 mg, 15 mg, 20 mg, 25 mg, 30 mg, 35 mg, 40 mg, 45 mg, 50 mg, 55 mg, 60 mg, 75 mg, 80 mg, 85 mg, 90 mg, 95 mg, 100 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 225 mg, 250 mg, 275 mg, or 300 mg, miglitol or a pharmaceutically acceptable salt thereof.

In embodiments, methods of treating a metabolic disorder such as type 1 diabetes, type 2 diabetes or pre-diabetes herein include administering to a patient in need thereof gaboxadol or a pharmaceutically acceptable salt thereof, in combination with about 50 mcg to about 1000 mcg voglibose or a pharmaceutically acceptable salt thereof.

In embodiments, about 100 mcg to about 900 mcg of voglibose or a pharmaceutically acceptable salt thereof may be administered in 24 hours. In embodiments, about 200 mcg to about 300 mcg of voglibose or a pharmaceutically acceptable salt thereof may be administered in 24 hours. In embodiments, voglibose or a pharmaceutically acceptable salt thereof may be administered in divided doses over 24 hours, e.g., 200 mcg three times daily or 300 mcg three times daily. In embodiments, voglibose or a pharmaceutically acceptable salt thereof may be administered once a day, e.g., with a morning meal. In embodiments, voglibose or a pharmaceutically acceptable salt thereof can be given in doses varying from about 50 mcg to 1000 mcg per day using various dosing regimens from, e.g., about 50 mcg to 500 mcg, or 200 mcg to 700 mcg (1-3 times a day), 75 mcg to 100 mcg, 100 mcg to 150 mcg, 150 mcg to 200 mcg, 200 mcg to 250 mcg, 300 mcg to 350 mcg, 350 mcg to 400 mcg, 450 mcg to 500 mcg, 550 mcg to 600 mcg, 650 mcg to 700 mcg, 750 mcg to 800 mcg, 850 mcg to 900 mcg, or 950 mcg to 1000 mcg, once or twice a day. Particular dosage strengths may be, e.g., 50, 75, 100, 125, 150, 175, 200, 225, 250, 275, 300, 325, 350, 375, 400, 425, 450, 475, 500, 525, 550, 575, 600, 625, 650, 675, 700, 725, or 750 mcg of voglibose or a pharmaceutically acceptable salt thereof.

In embodiments, the patient is administered 50 mcg to 75 mcg, 75 mcg to 100 mcg, 100 mcg to 125 mcg, 125 mcg to 150 mcg, 150 mcg to 175 mcg, 175 mcg to 200 mcg, 200 mcg to 225 mcg, 225 mcg to 250 mcg, 250 mcg to 275 mcg, 275 mcg to 300 mcg, 300 mcg, to 325 mcg, 325 mcg to 350 mcg, 350 mcg to 375 mcg, 375 mcg to 400 mcg, 400 mcg to 425 mcg, 425 mcg to 450 mcg, 450 mcg to 475 mcg, 475 mcg to 500 mcg, 500 mcg to 525 mcg, 525 mcg to 550 mcg, 550 mcg to 575 mcg, 575 mcg to 600 mcg, 600 mcg to 625 mcg, 625 mcg to 650 mcg, 650 mcg to 675 mcg, 675 mcg to 700 mcg, 700 mcg to 725 mcg, 725 mcg to 750 mcg, 750 mcg to 775 mcg, 775 mcg to 800 mcg, 800 mcg to 825 mcg, 825 mcg to 850 mcg, 850 mcg to 875 mcg, 875 mcg to 900 mcg, 900 mcg to 925 mcg, 925 mcg to 950 mcg, 950 mcg to 975 mcg, or 975 mcg to 1000 mcg, voglibose or a pharmaceutically acceptable salt thereof.

In embodiments, the patient is administered 50 mcg, 75 mcg, 100 mcg, 125 mcg, 150 mcg, 175 mcg, 200 mcg, 225 mcg, 250 mcg, 275 mcg, 300 mcg, 325 mcg, 350 mcg, 375 mcg, 400 mcg, 425 mcg, 450 mcg, 475 mcg, 500 mcg, 525 mcg, 550 mcg, 575 mcg, 600 mcg, 625 mcg, 650 mcg, 675 mcg, 700 mcg, 725 mcg, 750 mcg, 775 mcg, 800 mcg, 825 mcg, 850 mcg, 875 mcg, 900 mcg, 925 mcg, 950 mcg, 975 mcg, or 1000 mcg, voglibose or a pharmaceutically acceptable salt thereof.

In embodiments methods of treating a metabolic disorder such as type 1 diabetes, type 2 diabetes or pre-diabetes include administering to a patient in need thereof gaboxadol or a pharmaceutically acceptable salt thereof in combination with a pharmaceutical composition including about 50 mcg to about 1000 mcg voglibose or a pharmaceutically acceptable salt thereof.

In embodiments, the pharmaceutical compositions include 50 mcg to 75 mcg, 75 mcg to 100 mcg, 100 mcg to 125 mcg, 125 mcg to 150 mcg, 150 mcg to 175 mcg, 175 mcg to 200 mcg, 200 mcg to 225 mcg, 225 mcg to 250 mcg, 250 mcg to 275 mcg, 275 mcg to 300 mcg, 300 mcg, to 325 mcg, 325 mcg to 350 mcg, 350 mcg to 375 mcg, 375 mcg to 400 mcg, 400 mcg to 425 mcg, 425 mcg to 450 mcg, 450 mcg to 475 mcg, 475 mcg to 500 mcg, 500 mcg to 525 mcg, 525 mcg to 550 mcg, 550 mcg to 575 mcg, 575 mcg to 600 mcg, 600 mcg to 625 mcg, 625 mcg to 650 mcg, 650 mcg to 675 mcg, 675 mcg to 700 mcg, 700 mcg to 725 mcg, 725 mcg to 750 mcg, 750 mcg to 775 mcg, 775 mcg to 800 mcg, 800 mcg to 825 mcg, 825 mcg to 850 mcg, 850 mcg to 875 mcg, 875 mcg to 900 mcg, 900 mcg to 925 mcg, 925 mcg to 950 mcg, 950 mcg to 975 mcg, or 975 mcg to 1000 mcg, voglibose or a pharmaceutically acceptable salt thereof.

In embodiments, the pharmaceutical compositions include 50 mcg, 75 mcg, 100 mcg, 125 mcg, 150 mcg, 175 mcg, 200 mcg, 225 mcg, 250 mcg, 275 mcg, 300 mcg, 325 mcg, 350 mcg, 375 mcg, 400 mcg, 425 mcg, 450 mcg, 475 mcg, 500 mcg, 525 mcg, 550 mcg, 575 mcg, 600 mcg, 625 mcg, 650 mcg, 675 mcg, 700 mcg, 725 mcg, 750 mcg, 775 mcg, 800 mcg, 825 mcg, 850 mcg, 875 mcg, 900 mcg, 925 mcg, 950 mcg, 975 mcg, or 1000 mcg, voglibose or a pharmaceutically acceptable salt thereof.

In embodiments, a patient in need thereof is administered gaboxadol or a pharmaceutically acceptable salt thereof in combination with a meglitinide or a pharmaceutically acceptable salt thereof. In embodiments, a patient in need thereof is administered a pharmaceutical composition including gaboxadol or a pharmaceutically acceptable salt thereof in combination with a meglitinide or a pharmaceutically acceptable salt thereof. Examples of meglitinides (glinides) include repaglinide, nateglinide and mitiglinide.

In embodiments, methods of treating a metabolic disorder such as type 1 diabetes, type 2 diabetes or pre-diabetes herein include administering to a patient in need thereof gaboxadol or a pharmaceutically acceptable salt thereof, in combination with about 0.1 mg to about 20 mg repaglinide or a pharmaceutically acceptable salt thereof.

In embodiments, about 0.2 mg to about 20 mg of repaglinide or a pharmaceutically acceptable salt thereof may be administered in 24 hours. In embodiments, about 0.3 mg to about 20 mg of repaglinide or a pharmaceutically acceptable salt thereof may be administered in 24 hours. In embodiments, about 0.4 mg to about 20 mg of repaglinide or a pharmaceutically acceptable salt thereof may be administered in 24 hours. In embodiments, about 0.5 mg to about 20 mg of repaglinide or a pharmaceutically acceptable salt thereof may be administered in 24 hours. In embodiments, about 0.6 mg to about 20 mg of repaglinide or a pharmaceutically acceptable salt thereof may be administered in 24 hours. In embodiments, about 0.7 mg to about 20 mg of repaglinide or a pharmaceutically acceptable salt thereof may be administered in 24 hours. In embodiments, about 0.8 mg to about 20 mg of repaglinide or a pharmaceutically acceptable salt thereof may be administered in 24 hours. In embodiments, about 0.9 mg to about 20 mg of repaglinide or a pharmaceutically acceptable salt thereof may be administered in 24 hours. In embodiments, about 1 mg to about 20 mg of repaglinide or a pharmaceutically acceptable salt thereof may be administered in 24 hours. In embodiments, about 1.25 mg to about 20 mg of repaglinide or a pharmaceutically acceptable salt thereof may be administered in 24 hours. In embodiments, about 1.5 mg to about 20 mg of repaglinide or a pharmaceutically acceptable salt thereof may be administered in 24 hours. In embodiments, about 1.75 mg to about 20 mg of repaglinide or a pharmaceutically acceptable salt thereof may be administered in 24 hours. In embodiments, about 2 mg to about 20 mg of repaglinide or a pharmaceutically acceptable salt thereof may be administered in 24 hours. In embodiments, about 2.25 mg to about 20 mg of repaglinide or a pharmaceutically acceptable salt thereof may be administered in 24 hours. In embodiments, about 2.5 mg to about 20 mg of repaglinide or a pharmaceutically acceptable salt thereof may be administered in 24 hours. In embodiments, about 2.75 mg to about 20 mg of repaglinide or a pharmaceutically acceptable salt thereof may be administered in 24 hours. In embodiments, about 3 mg to about 3 mg to about 20 mg of repaglinide or a pharmaceutically acceptable salt thereof may be administered in 24 hours. In embodiments, about 3.25 mg to about 20 mg of repaglinide or a pharmaceutically acceptable salt thereof may be administered in 24 hours. In embodiments, about 3.5 mg to about 20 mg of repaglinide or a pharmaceutically acceptable salt thereof may be administered in 24 hours. In embodiments, about 3.75 mg to about 20 mg of repaglinide or a pharmaceutically acceptable salt thereof may be administered in 24 hours. In embodiments, about 4 mg to about 20 mg of repaglinide or a pharmaceutically acceptable salt thereof may be administered in 24 hours. In embodiments, about 4.25 mg to about 20 mg of repaglinide or a pharmaceutically acceptable salt thereof may be administered in 24 hours. In embodiments, about 4.5 mg to about 20 mg of repaglinide or a pharmaceutically acceptable salt thereof may be administered in 24 hours. In embodiments, about 4.75 mg to about 20 mg of repaglinide or a pharmaceutically acceptable salt thereof may be administered in 24 hours. In embodiments, 0.5 mg to about 4 mg may be administered with each meals up to 16 mg in 24 hours.

In embodiments, about 0.1 mg, 0.2 mg, 0.3 mg, 0.4 mg, 0.5 mg, 0.6 mg, 0.7 mg, 0.8 mg, 0.9 mg, 1 mg, 1.1 mg, 1.2 mg, 1.3 mg, 1.4 mg, 1.5 mg, 1.6 mg, 1.7 mg, 1.8 mg, 1.9 mg, 2 mg, 2.1 mg, 2.2 mg, 2.3 mg, 2.4 mg, 2.5 mg, 2.6 mg, 2.7 mg, 2.8 mg, 2.9 mg, 3 mg, 3.1 mg, 3.2 mg, 3.3 mg, 3.4 mg, 3.5 mg, 3.6 mg, 3.7 mg, 3.8 mg, 3.9 mg, 4 mg, 4.1 mg, 4.2 mg, 4.3 mg, 4.4 mg, 4.5 mg, 4.6 mg, 4.7 mg, 4.8 mg, 4.9 mg, 5 mg, 5.25 mg, 5.5 mg, 5.75 mg, 6.0 mg, 6.25 mg, 6.5 mg, 6.75 mg, 7.0 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10.0 mg, 10.25 mg, 10.5 mg, 10.75 mg, 11.0 mg, 11.25 mg, 11.5 mg, 11.75 mg, 12.0 mg, 12.25 mg, 12.5 mg, 12.75 mg, 13.0 mg, 13.25 mg, 13.5 mg, 13.75 mg, 14.0 mg, 14.25 mg, 14.5 mg, 14.75 mg, 15.0 mg, 15.25 mg, 15.5 mg, 15.75 mg, 16.0 mg, 16.25 mg, 16.5 mg, 16.75 mg, 17.0 mg, 17.25 mg, 17.5 mg, 17.75 mg, 18.0 mg, 18.5 mg, 19 mg, 19.5 mg or 20 mg, of repaglinide or a pharmaceutically acceptable salt thereof may be administered in 24 hours. In embodiments, about 0.5 mg of repaglinide or a pharmaceutically acceptable salt thereof may be administered in 24 hours. In embodiments, about 1 mg of repaglinide or a pharmaceutically acceptable salt thereof may be administered in 24 hours. In embodiments, about 2 mg of repaglinide or a pharmaceutically acceptable salt thereof may be administered in 24 hours. In embodiments, about 0.25 mg of repaglinide or a pharmaceutically acceptable salt thereof may be administered three times or four times a day, with meals. In embodiments, about 0.5 mg of repaglinide or a pharmaceutically acceptable salt thereof may be administered three times or four times a day, with meals. In embodiments, about 1 mg of repaglinide or a pharmaceutically acceptable salt thereof may be administered three times or four times a day, with meals. In embodiments, about 2 mg of repaglinide or a pharmaceutically acceptable salt thereof may be administered three or four times a day, with meals. In embodiments, about 3 mg of repaglinide or a pharmaceutically acceptable salt thereof may be administered three or four times a day, with meals. In embodiments, about 4 mg of repaglinide or a pharmaceutically acceptable salt thereof may be administered three or four times a day, with meals. In embodiments, the repaglinide or a pharmaceutically acceptable salt thereof may be administered in divided doses over 24 hours, e. g., twice, three or four times a day. In embodiments, repaglinide may be administered once a day.

In embodiments methods of treating a metabolic disorder such as type 1 diabetes, type 2 diabetes or pre-diabetes include administering to a patient in need thereof gaboxadol or a pharmaceutically acceptable salt thereof in combination with a pharmaceutical composition including about 0.1 mg to about 20 mg repaglinide or a pharmaceutically acceptable salt thereof.

In embodiments, the compositions include 0.1 mg to 1 mg, 0.2 mg to 1 mg, 0.3 mg to 1 mg, 0.4 mg to 1 mg, 0.5 mg to 1 mg, 0.6 mg to 1 mg, 0.7 mg to 1 mg, 0.75 mg to 1 mg, 0.8 mg to 1 mg, 0.9 mg to 1 mg, 0.1 mg to 2 mg, 0.2 mg to 2 mg, 0.3 mg to 2 mg, 0.4 mg to 2 mg, 0.5 mg to 2 mg, 0.6 mg to 2 mg, 0.7 mg to 2 mg, 0.75 mg to 2 mg, 0.8 mg to 2 mg, 0.9 mg to 2 mg, 1.0 mg to 2 mg, 1.1 mg to 2 mg, 1.2 mg to 2 mg, 1.25 mg to 2 mg, 1.3 mg to 2 mg, 1.4 mg to 2 mg, 1.5 mg to 2 mg, 1.6 mg to 2 mg, 1.7 mg to 2 mg, 1.75 mg to 2 mg, 1.8 mg to 2 mg, 1.9 mg to 2 mg, 0.1 mg to 5 mg, 0.2 mg to 5 mg, 0.3 mg to 0.5 mg, 0.4 mg to 5 mg, 0.5 mg to 5 mg, 0.6 mg to 5 mg, 0.7 mg to 5 mg, 0.75 mg to 5 mg, 0.8 mg to 5 mg, 0.9 mg to 5 mg, 1.0 mg to 5 mg, 1.1 mg to 5 mg, 1.2 mg to 5 mg, 1.25 mg to 5 mg, 1.3 mg to 5 mg, 1.4 mg to 5 mg, 1.5 mg to 5 mg, 1.6 mg to 5 mg, 1.7 mg to 5 mg, 1.75 mg to 5 mg, 1.8 mg to 5 mg, 1.9 mg to 5 mg, 2.0 mg to 5 mg, 2.25 mg to 5 mg, 2.5 mg to 5 mg, 2.75 to 5 mg, 3 mg to 5 mg, 3.5 mg to 5 mg, 4 mg to 5 mg, 4.5 mg, to 5 mg, 0.1 mg to 2.0 mg, 0.5 mg to 2.0 mg, 0.75 mg to 2.0 mg, 1.0 mg to 2.0 mg, 1.25 mg to 2.0 mg, 1.5 mg to 2.0 mg, 1.75 mg to 2.0 mg, or 2.0 mg to 2.5 mg 0.1 mg to 2.5 mg, 0.5 mg to 2.5 mg, 0.75 mg to 2.5 mg, 1.0 mg to 2.5 mg, 1.25 mg to 2.5 mg, 1.5 mg to 2.5 mg, 1.75 mg to 2.5 mg, or 2.0 mg to 2.5 mg of repaglinide or a pharmaceutically acceptable salt thereof. In embodiments, the compositions include 0.1 mg, 0.5 mg, 0.75 mg, 1 mg, 1.25 mg, 1.5 mg, 1.75 mg, 2 mg, 2.25 mg, 2.5 mg, 2.75 mg, 3 mg, 3.25 mg, 3.5 mg, 3.75 mg, 4 mg, 4.25 mg, 4.5 mg, 4.75 mg, or 5 mg, repaglinide or a pharmaceutically acceptable salt thereof.

In embodiments, methods of treating a metabolic disorder such as type 1 diabetes, type 2 diabetes or pre-diabetes include administering to a patient in need thereof gaboxadol or a pharmaceutically acceptable salt thereof, in combination with about 10 mg to about 500 mg nateglinide or a pharmaceutically acceptable salt thereof.

In embodiments, about 10 mg to about 500 mg of nateglinide or a pharmaceutically acceptable salt thereof may be administered in 24 hours. In embodiments, about 25 mg to about 500 mg of nateglinide or a pharmaceutically acceptable salt thereof may be administered in 24 hours. In embodiments, about 30 mg to about 500 mg of nateglinide or a pharmaceutically acceptable salt thereof may be administered in 24 hours. In embodiments, about 60 mg to about 450 mg of nateglinide or a pharmaceutically acceptable salt thereof may be administered in 24 hours. In embodiments, about 90 mg to about 425 mg of nateglinide or a pharmaceutically acceptable salt thereof may be administered in 24 hours. In embodiments, about 120 mg to about 400 mg of nateglinide or a pharmaceutically acceptable salt thereof may be administered in 24 hours. In embodiments, about 150 mg to about 360 mg of nateglinide or a pharmaceutically acceptable salt thereof may be administered in 24 hours. In embodiments, about 180 mg to about 360 mg of nateglinide or a pharmaceutically acceptable salt thereof may be administered in 24 hours. In embodiments, about 210 mg to about 360 mg of nateglinide or a pharmaceutically acceptable salt thereof may be administered in 24 hours. In embodiments, about 240 mg to about 360 mg of nateglinide or a pharmaceutically acceptable salt thereof may be administered in 24 hours. In embodiments, about 270 mg to about 360 mg of nateglinide or a pharmaceutically acceptable salt thereof may be administered in 24 hours. In embodiments, about 300 mg to about 360 mg of nateglinide or a pharmaceutically acceptable salt thereof may be administered in 24 hours. In embodiments, about 330 mg to about 360 mg of nateglinide or a pharmaceutically acceptable salt thereof may be administered in 24 hours. In embodiments, about 90 mg of nateglinide or a pharmaceutically acceptable salt thereof may be administered in 24 hours. In embodiments, about 120 mg of nateglinide or a pharmaceutically acceptable salt thereof may be administered in 24 hours. In embodiments, about 150 mg of nateglinide or a pharmaceutically acceptable salt thereof may be administered in 24 hours. In embodiments, about 180 mg of nateglinide or a pharmaceutically acceptable salt thereof may be administered in 24 hours. In embodiments, about 210 mg of nateglinide or a pharmaceutically acceptable salt thereof may be administered in 24 hours. In embodiments, about 240 mg of nateglinide or a pharmaceutically acceptable salt thereof may be administered in 24 hours. In embodiments, about 270 mg of nateglinide or a pharmaceutically acceptable salt thereof may be administered in 24 hours. In embodiments, about 300 mg of nateglinide or a pharmaceutically acceptable salt thereof may be administered in 24 hours. In embodiments, about 330 mg of nateglinide or a pharmaceutically acceptable salt thereof may be administered in 24 hours. In embodiments, about 360 mg of nateglinide or a pharmaceutically acceptable salt thereof may be administered in 24 hours. In embodiments, about 390 mg of nateglinide or a pharmaceutically acceptable salt thereof may be administered in 24 hours. In embodiments, about 420 mg of nateglinide or a pharmaceutically acceptable salt thereof may be administered in 24 hours. In embodiments, about 450 mg of nateglinide or a pharmaceutically acceptable salt thereof may be administered in 24 hours. In embodiments, about 480 mg of nateglinide or a pharmaceutically acceptable salt thereof may be administered in 24 hours. In embodiments, the nateglinide or a pharmaceutically acceptable salt thereof may be administered in divided doses over 24 hours, e.g., 30 mg, 60 mg, 90 mg, 120 mg, or 150 twice or three times daily. In embodiments, nateglinide or a pharmaceutically acceptable salt thereof may be administered once a day, e.g. 60 mg or 120 mg.

In embodiments, the patient is administered 10 mg to 15 mg, 15 mg to 20 mg, 20 mg to 25 mg, 25 mg to 30 mg, 30 mg to 35 mg, 35 mg to 40 mg, 40 mg to 45 mg, 45 mg to 50 mg, 50 mg to 55 mg, 55 mg to 60 mg, 60 mg to 75 mg, 75 mg, to 80 mg, 80 mg to 85 mg, 85 mg to 90 mg, 90 mg to 95 mg, 95 mg to 100 mg, 100 mg to 110 mg, 110 mg to 115 mg, 115 mg to 120 mg, 125 mg to 130 mg, 130 mg to 135 mg, 135 mg to 140 mg, 140 mg to 145 mg, 145 mg to 150 mg, 150 mg to 155 mg, 155 mg to 160 mg, 160 mg, to 165 mg, 165 mg to 170 mg, 175 mg to 180 mg, 180 mg to 185 mg, 185 mg to 190 mg, 190 mg to 195 mg, 195 to 200 mg, 200 mg to 225 mg, 225 mg to 250 mg, 250 mg to 275 mg, 275 mg to 300 mg, 300 mg to 325 mg, 325 mg to 350 mg, 350 mg to 375 mg, 375 mg to 400 mg, 400 mg to 425 mg, 425 mg to 450 mg, 450 mg to 475 mg, or 475 mg to 500 mg, nateglinide or a pharmaceutically acceptable salt thereof.

In embodiments, the patient is administered 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 210 mg, 220 mg, 225 mg, 230 mg, 240 mg, 250 mg, 260 mg, 270 mg, 275 mg, 280 mg, 290 mg, 300 mg, 310 mg, 320 mg, 325 mg, 330 mg, 340 mg, 350 mg, 360 mg, 370 mg, 375 mg, 380 mg, 390 mg, 400 mg, 425 mg, 450 mg, 475 mg, or 500 mg, nateglinide or a pharmaceutically acceptable salt thereof.

In embodiments methods of treating a metabolic disorder such as type 1 diabetes, type 2 diabetes or pre-diabetes include administering to a patient in need thereof gaboxadol or a pharmaceutically acceptable salt thereof, in combination with a pharmaceutical composition including about 10 mg to about 500 mg nateglinide or a pharmaceutically acceptable salt thereof.

In embodiments, the compositions include 10 mg to 15 mg, 15 mg to 20 mg, 20 mg to 25 mg, 25 mg to 30 mg, 30 mg to 35 mg, 35 mg to 40 mg, 40 mg to 45 mg, 45 mg to 50 mg, 50 mg to 55 mg, 55 mg to 60 mg, 60 mg to 75 mg, 75 mg to 80 mg, 80 mg to 85 mg, 85 mg to 90 mg, 90 mg to 95 mg, 95 mg to 100 mg, 100 mg to 110 mg, 110 mg to 115 mg, 115 mg to 120 mg, 120 mg, to 130 mg, 125 mg to 130 mg, 130 mg to 135 mg, 135 mg to 140 mg, 140 mg to 145 mg, 145 mg to 150 mg, 150 mg to 155 mg, 155 mg to 160 mg, 160 mg to 165 mg, 165 mg to 170 mg, 175 mg to 180 mg, 180 mg to 185 mg, 185 mg to 190 mg, 190 mg to 195 mg, 195 to 200 mg, 200 mg to 225 mg, 225 mg to 250 mg, 250 mg to 275 mg, 275 mg to 300 mg, 300 mg to 325 mg, 325 mg to 350 mg, 350 mg to 375 mg, 375 mg to 400 mg, 400 mg to 425 mg, 425 mg to 450 mg, 450 mg to 475 mg, or 475 mg to 500 mg, nateglinide or a pharmaceutically acceptable salt thereof.

In embodiments, the compositions include 10 mg, 15 mg, 20 mg, 25 mg, 30 mg, 35 mg, 40 mg, 45 mg, 50 mg, 55 mg, 60 mg, 70 mg, 75 mg, 80 mg, 85 mg, 90 mg, 95 mg, 100 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 210 mg, 220 mg, 225 mg, 230 mg, 240 mg, 250 mg, 275 mg, 300 mg, 325 mg, 350 mg, 375 mg, 400 mg, 425 mg, 450 mg, 475 mg, or 500 mg, nateglinide or a pharmaceutically acceptable salt thereof.

In embodiments, methods of treating a metabolic disorder such as type 1 diabetes, type 2 diabetes or pre-diabetes include administering to a patient in need thereof gaboxadol or a pharmaceutically acceptable salt thereof, in combination with about 1 mg to about 60 mg mitiglinide or a pharmaceutically acceptable salt thereof.

In embodiments, about 1 mg to about 60 mg of mitiglinide or a pharmaceutically acceptable salt thereof may be administered in 24 hours. In embodiments, about 2 mg to about 60 mg of mitiglinide or a pharmaceutically acceptable salt thereof may be administered in 24 hours. In embodiments, about 3 mg to about 60 mg of mitiglinide or a pharmaceutically acceptable salt thereof may be administered in 24 hours. In embodiments, about 4 mg to about 55 mg of mitiglinide or a pharmaceutically acceptable salt thereof may be administered in 24 hours. In embodiments, about 5 mg to about 50 mg of mitiglinide or a pharmaceutically acceptable salt thereof may be administered in 24 hours. In embodiments, about 6 mg to about 45 mg of mitiglinide or a pharmaceutically acceptable salt thereof may be administered in 24 hours. In embodiments, about 7 mg to about 40 mg of mitiglinide or a pharmaceutically acceptable salt thereof may be administered in 24 hours. In embodiments, about 8 mg to about 35 mg of mitiglinide or a pharmaceutically acceptable salt thereof may be administered in 24 hours. In embodiments, about 10 mg to about 30 mg of mitiglinide or a pharmaceutically acceptable salt thereof may be administered in 24 hours. In embodiments, about 10 mg to about 30 mg of mitiglinide or a pharmaceutically acceptable salt thereof may be administered in 24 hours. In embodiments, about 10 mg to about 20 mg of mitiglinide or a pharmaceutically acceptable salt thereof may be administered in 24 hours. In embodiments, about 10 mg to about 15 mg of mitiglinide or a pharmaceutically acceptable salt thereof may be administered in 24 hours. In embodiments, about 15 mg to about 30 mg of mitiglinide or a pharmaceutically acceptable salt thereof may be administered in 24 hours. In embodiments, about 10 mg of mitiglinide or a pharmaceutically acceptable salt thereof may be administered in 24 hours. In embodiments, about 15 mg of mitiglinide or a pharmaceutically acceptable salt thereof may be administered in 24 hours. In embodiments, about 20 mg of mitiglinide or a pharmaceutically acceptable salt thereof may be administered in 24 hours. In embodiments, about 25 mg of mitiglinide or a pharmaceutically acceptable salt thereof may be administered in 24 hours. In embodiments, about 30 mg of mitiglinide or a pharmaceutically acceptable salt thereof may be administered in 24 hours. In embodiments, about 35 mg of mitiglinide or a pharmaceutically acceptable salt thereof may be administered in 24 hours. In embodiments, about 40 mg of mitiglinide or a pharmaceutically acceptable salt thereof may be administered in 24 hours. In embodiments, about 45 mg of mitiglinide or a pharmaceutically acceptable salt thereof may be administered in 24 hours. In embodiments, about 50 mg of mitiglinide or a pharmaceutically acceptable salt thereof may be administered in 24 hours. In embodiments, about 55 mg of mitiglinide or a pharmaceutically acceptable salt thereof may be administered in 24 hours. In embodiments, about 60 mg of mitiglinide or a pharmaceutically acceptable salt thereof may be administered in 24 hours. In embodiments, the mitiglinide or a pharmaceutically acceptable salt thereof may be administered in divided doses over 24 hours, e.g., 5 mg, 10 mg, 15 mg, 20 mg, 25 mg, or 30 mg, twice or three times daily. In embodiments, mitiglinide or a pharmaceutically acceptable salt thereof may be administered once a day, e.g. 30 mg or 60 mg.

In embodiments, the patient is administered 1.0 mg to 30 mg, 5 mg to 10 mg, 5 mg to 15 mg, 5 mg to 20 mg, 5 mg to 25 mg, 5 mg to 30 mg, 5 mg to 35 mg, 5 mg to 40 mg, 5 mg to 45 mg, 5 mg to 50 mg, 5 mg to 55 mg, 5 mg to 60 mg, 10 mg to 15 mg, 10 mg to 20 mg, 10 mg to 25, 10 mg to 30 mg, 10 mg to 35 mg, 10 mg to 40 mg, 10 mg to 45 mg, 10 mg to 50 mg, 10 mg to 60 mg, 15 mg to 20 mg, 15 mg to 25 mg, 15 mg to 30 mg, 15 mg, 35 mg, 15 mg to 40 mg, 15 mg to 45 mg, 15 mg to 50 mg, 15 mg to 55 mg, 15 mg to 60 mg, 20 mg to 25 mg, 20 mg to 30 mg, 20 mg to 35 mg, 20 mg to 40 mg, 20 mg to 45 mg, 20 mg to 50 mg, 20 mg to 60 mg, 25 mg to 30 mg, 25 mg to 35 mg, 25 mg to 40 mg, 25 mg to 45 mg, 25 mg to 50 mg, 25 mg to 55 mg, 25 mg to 60 mg, 30 mg to 35 mg, 35 mg to 40 mg, 45 mg to 50 mg, or 55 mg to 60 mg, mitiglinide or a pharmaceutically acceptable salt thereof.

In embodiments, the patient is administered 1 mg, 5 mg, 10 mg, 12 mg, 15 mg, 17 mg, 20 mg, 25 mg, 30 mg, 35 mg, 40 mg, 45 mg, 50 mg, 55 mg, or 60 mg mitiglinide or a pharmaceutically acceptable salt thereof.

In embodiments methods of treating a metabolic disorder such as type 1 diabetes, type 2 diabetes or pre-diabetes include administering to a patient in need thereof gaboxadol or a pharmaceutically acceptable salt thereof, in combination with a pharmaceutical composition including about 1 mg to about 60 mg mitiglinide or a pharmaceutically acceptable salt thereof.

In embodiments, the compositions include 1.0 mg to 10 mg, 1.0 mg to 15 mg, 1.0 mg to 20 mg, 1.0 mg to 25 mg, 1.0 mg to 30 mg, 1.0 mg to 35 mg, 1.0 mg to 40 mg, 1.0 mg to 45 mg, 1.0 mg to 50 mg, 1.0 mg to 55 mg, 1.0 mg to 60 mg, 5 mg to 10 mg, 5 mg to 20 mg, 5 mg to 25 mg, 5 mg to 30 mg, 5 mg to 35 mg, 5 mg to 40 mg, 5 mg to 45 mg, 5 mg to 50 mg, 5 mg to 55 mg, 5 mg to 60 mg, 10 mg to 15 mg, 10 mg to 20 mg, 10 mg to 25 mg, 10 mg to 30 mg, 10 mg to 35 mg, 10 mg to 40 mg, 10 mg to 45 mg, 10 mg to 50 mg, 10 mg to 55 mg, 10 mg to 60 mg, 15 mg to 20 mg, 20 mg to 25 mg, 25 mg to 30 mg, 25 mg to 35 mg, 25 mg to 40 mg, 25 mg to 45 mg, 25 mg to 50 mg, 25 mg to 55 mg, 30 mg to 35 mg, 30 mg to 40 mg, 35 mg to 45 mg, 35 mg to 40 mg, 35 mg to 45 mg, 35 mg to 50 mg, 35 mg to 55 mg, 35 mg to 60 mg, 40 mg to 45 mg, 40 mg to 50 mg, 40 mg to 55 mg, 40 mg to 60 mg, 45 mg to 50 mg, 45 mg to 55 mg, 45 mg to 60 mg, 50 mg to 55 mg, 50 mg to 60 mg, or 55 mg to 60 mg, mitiglinide or a pharmaceutically acceptable salt thereof.

In embodiments, the compositions include 5 mg, 10 mg, 15 mg, 20 mg, 25 mg, 30 mg, 35 mg, 40 mg, 45 mg, 50 mg, 55 mg, or 60 mg mitiglinide or a pharmaceutically acceptable salt thereof.

In embodiments, methods of treating a metabolic disorder such as type 1 diabetes, type 2 diabetes or pre-diabetes include administering to a patient in need thereof gaboxadol or a pharmaceutically acceptable salt thereof, in combination with insulin or an insulin analog. The insulin can be commercially available fast acting insulin analogs, e.g., lispro or glulisine, short acting (regular) insulin, intermediate acting (NPH) insulin, long acting insulin, e.g., glargine or detemir, ultra-long acting, e.g., degludec, or combination insulin products. Insulin or insulin analogs may be administered parenterally, e.g., subcutaneously. Short acting or regular human insulin may be available in 2 concentrations:

100 units of insulin per mL (U-100) and 500 units of insulin per mL (U-500). Insulin may be administered as a fixed dose or as a flexible dose therapy. Factors which may affect insulin dosage include carbohydrate intake, physical activity, illness, body mass and insulin resistance. Typically, insulin doses are individualized based on metabolic needs and frequent monitoring of blood glucose. In general, total daily insulin requirements can be between 0.5 to 1 unit/kg/day.

Unless defined otherwise, all technical and scientific terms used herein have the same meanings as commonly understood by one of skill in the art to which the disclosure herein belongs.

The term "about" or "approximately" as used herein means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, up to 10%, up to 5%, and/or up to 1% of a given value. Alternatively, particularly with respect to biological systems or processes, the term can mean within an order of magnitude, preferably within 5-fold, and more preferably within 2-fold, of a value.

"Improvement" refers to the treatment of symptoms or conditions associated with metabolic diseases, measured relative to at least one symptom or condition of the metabolic disease.

"Improvement in next day functioning" or "wherein there is improvement in next day functioning" refers to improvement after waking from an overnight sleep period wherein the beneficial effect of administration of one or more of gaboxadol alone or in combination with one or more hypoglycemic agents such as a biguanide, a dipeptidyl peptidase-4 (DPP-4) inhibitor, a sulphonylurea, a thiazolidinedione, a meglitinide (glinide), an alpha-glucosidase blocker, an glucagon-like peptide-1 receptor agonist, insulin and an insulin analog, applies to at least one symptom or condition associated with a metabolic disease and is discernable, either subjectively by a patient or objectively by an observer, for a period of time, e.g., 2 hours, 3 hours, 4 hours, 5 hours, 6 hours, 12 hours, 24 hours, etc. after waking.

"Treat", "Treating" or "treatment" refers to alleviating or delaying the appearance of clinical symptoms of a disease or condition in a subject that may be afflicted with or predisposed to the disease or condition, but does not yet experience or display clinical or subclinical symptoms of the disease or condition. In certain embodiments, "treat", "treating" or "treatment" may refer to preventing the appearance of clinical symptoms of a disease or condition in a subject that may be afflicted with or predisposed to the disease or condition, but does not yet experience or display clinical or subclinical symptoms of the disease or condition. "Treat", "treating" or "treatment" also refers to inhibiting the disease or condition, e.g., arresting or reducing its development or at least one clinical or subclinical symptom thereof. "Treat", "treating" or "treatment" further refers to relieving the disease or condition, e.g., causing regression of the disease or condition or at least one of its clinical or subclinical symptoms. The term "treat" "treating" or "treatment" may mean to relieve or alleviate the intensity and/or duration of a manifestation of a disease experienced by a subject in response to a given stimulus (e.g., pressure, tissue injury, cold temperature, etc.). The benefit to a subject to be treated may be statistically significant, mathematically significant, or at least perceptible to the subject and/or the physician.

"Patient in need thereof" may include individuals that have been diagnosed with a metabolic disease. "Patient" and "subject" are used interchangeably herein.

"Effective amount" or "therapeutically effective amount" means a dosage sufficient to alleviate one or more symptoms of a disorder, disease, or condition being treated, or to otherwise provide a desired pharmacological and/or physiologic effect. The "effective amount" or "therapeutically effective amount" can vary depending on the compound, the disease and its severity and the age, weight, physical condition and responsiveness of the subject to be treated. In embodiments, a therapeutically effective amount of active agent(s) is an amount effective to treat a metabolic disease. The effective amount of the drug for pharmacological action, and therefore the dosage strength may depend on progression of the disease itself "Effective amount" or "therapeutically effective amount" may be used interchangeably herein.

"Pharmaceutically acceptable" refers to molecular entities and compositions that are "generally regarded as safe", e.g., they are biologically or pharmacologically compatible for in vivo use in animals or humans, that are physiologically tolerable and do not typically produce an allergic or similar untoward reaction, when administered to a human. In embodiments, this term refers to molecular entities and compositions approved by a regulatory agency of the federal or a state government, as the GRAS list under section 204(s) and 409 of the Federal Food, Drug and Cosmetic Act, that is subject to premarket review and approval by the FDA or similar lists, the U.S. Pharmacopeia or another generally recognized pharmacopeia for use in animals, and more particularly in humans.

The term "pharmaceutically acceptable salt", as used herein, refers to derivatives of the compounds defined herein, wherein the parent compound is modified by making acid or base salts thereof. Example of pharmaceutically acceptable salts include but are not limited to mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, tolunesulfonic, naphthalenesulfonic, methanesulfonic, ethane disulfonic, oxalic, and isethionic salts. The pharmaceutically acceptable salts can be synthesized from the parent compound, which contains a basic or acidic moiety, by conventional chemical methods.

"Co-administered with", "in combination with", "administered in combination with", "a combination of" or "administered along with" may be used interchangeably and mean that two or more agents are administered in the course of therapy. The agents may be administered together at the same time or separately in spaced apart intervals. The agents may be administered in a single dosage form or in separate dosage forms.

As used herein, "sustained release" or "extended release" means that the release of the therapeutically active agent occurs over an extended period of time leading to lower peak plasma concentrations and/or is directed to a prolonged $T_{max}$ as compared to "conventional release" or "immediate release." For example, extended release compositions may have a mean $T_{max}$ of about 5 or more hours.

The term "dissolution requirement" means the dissolution rate of dosage forms, including bead-based dosage forms, obtained when tested using the equipment and procedure specified in the USP XXV and conducted pursuant to the individual Official Monographs of USP XXV for the particular therapeutically active agent(s).

"PK" refers to the pharmacokinetic profile. $C_{max}$ is defined as the highest plasma drug concentration estimated during an experiment (ng/ml). $T_{max}$ is defined as the time when $C_{max}$ is estimated (min). $AUC_{0-\infty}$ is the total area under the plasma drug concentration-time curve, from drug administration until the drug is eliminated (ng·hr/ml or µg·hr/ml). The area under the curve is governed by clearance. Clearance is defined as the volume of blood or plasma that is totally cleared of its content of drug per unit time (ml/min).

"Prodrug" refers to a pharmacological substance (drug) that is administered to a subject in an inactive (or significantly less active) form. Once administered, the prodrug is metabolized in the body (in vivo) into a compound having the desired pharmacological activity.

"Analog" and "Derivative" may be used interchangeably and refer to a compound that possesses the same core as the parent compound, but may differ from the parent compound in bond order, the absence or presence of one or more atoms and/or groups of atoms, and combinations thereof. The derivative can differ from the parent compound, for example, in one or more substituents present on the core, which may include one or more atoms, functional groups, or substructures. In general, a derivative can be imagined to be formed, at least theoretically, from the parent compound via chemical and/or physical processes.

EXAMPLES

The Examples provided herein are included solely for augmenting the disclosure herein and should not be considered to be limiting in any respect.

Example 1

Prospective Assessment of the Efficacy of Gaboxadol in Patients with Type 2 Diabetes This study is designed to investigate the efficacy and safety of once-daily gaboxadol monotherapy administered orally at 5 mg, 10 mg and 20-mg doses vs. placebo over a 6-month period in treatment-naive patients with type 2 diabetes inadequately controlled with diet and exercise. This will be a multicenter, randomized, four-arm, parallel-group, double-blind, placebo-controlled trial. Patients between 18 and 77 years old with type 2 diabetes inadequately controlled with diet and exercise (HbA1c greater than or equal to 7.0% at screening visit) will be eligible. Patients with a screening HbA1c greater than 7.0% and less than 10.0% will encompass the main treatment cohort (MTC), whereas those with an HbA1c greater than 10.0% and less than 12.0% who otherwise meet all other inclusion and exclusion criteria will be eligible for direct entry into the open-label cohort (OLC). For eligibility, all patients will be required to be treatment naive (defined as never receiving medical treatment for diabetes [insulin and/or oral hypoglycemic medication] for greater than 6 months after original diagnosis, and no oral hypoglycemic medication for more than 3 consecutive days or 7 nonconsecutive days during the 8 weeks prior to screening), have a fasting C-peptide greater than or equal to 1 ng/mL (greater than or equal to 0.33 nmol/L), and a body mass index (BMI) less than or equal to 40 kg/m².

Following screening, MTC patients will enter a single-blind 2-week dietary and exercise placebo lead-in period. Patients who meet entrance criteria and demonstrate adequate compliance (80 to 120% of prescribed drug consumption) with study medication (placebo) during the lead-in period will qualify for enrollment. Patients will be randomized (1:1:1:1) to oral gaboxadol 5 mg, 10 mg, 20 mg, or placebo and will be followed for 24 weeks on double-blind study medication. Patients enrolled in the OLC will be entered directly into a 24-week treatment period where they will receive received oral, open-label gaboxadol at a dose of 20 mg once daily.

The primary endpoint will be change in HbA1c from baseline to week 24. Secondary endpoints will include change from baseline to week 24 in: (1) fasting plasma glucose (FPG); (2) proportion of patients achieving an HbA1 less than 7.0%; and (3) change from baseline in area under the curve (AUC) from 0 to 180 min for postprandial glucose (PPG) in response to a 75-g oral glucose tolerance test (OGTT). Other prespecified efficacy outcome measures will be PPG change from baseline at 120 min in response to an OGTT and changes from baseline to week 24 in levels of both fasting and postprandial insulin, C-peptide, and glucagon levels. B-Cell function will be measured by homeostasis model assessment (HOMA)-2 and insulin resistance.

Efficacy analyses will be performed on the randomized patients dataset, which will consist of randomized patients who receive at least one dose of study medication and who have a baseline and at least one post-baseline measurement. Each gaboxadol group will be compared with placebo for changes from baseline to week 24 in continuous variables utilizing an analysis of covariance (ANCOVA) model with treatment group as an effect and baseline value as a covariate. The percentage of patients achieving target HbA1c at week 24 will be compared between each gaboxadol treatment group vs. placebo, using a two-sided Fisher exact test. Demographic and other baseline characteristics will be summarized using descriptive statistics. Estimated average glucose (eAG) values will be calculated post hoc based on HbA1c values using the following linear regression: $eAG_{mg/dL}=28.7 \times HbA1c-46.7$. Within the framework of the ANCOVA model, point estimates and 95% confidence intervals (CIs) for the absolute and adjusted mean change within each treatment group, as well as for the differences in mean changes between each of the gaboxadol treatment groups (5 mg, 10 mg, and 20 mg) and the placebo group, will be calculated. For the primary endpoint, each comparison between a gaboxadol treatment group and the placebo group will be performed at the alpha=0.019 level from Dunnett's adjustment so that the overall type I error rate will be controlled at the 0.05 significance level. Sequential testing methodology will be utilized for secondary efficacy endpoints to adjust for multiplicity and preserve the overall type I error rate within each treatment group at the 0.05 level.

Example 2

Prospective Assessment of the Efficacy of Gaboxadol when Added to Metformin in Patients with Type 2 Diabetes This will be a 24 week randomized, four-arm, double-blind, placebo-controlled study of gaboxadol (5 mg, 10 mg or 20 mg once daily) or placebo plus a stable dose of metformin (1,500-2,500 mg) in patients (A1C≥7.0 and ≤10.0%). The study will include men and women with type 2 diabetes and inadequate glycemic control (A1C≥7.0 and ≤10.0%) taking a stable dose of metformin (≥1,500 but not >2,550 mg/day) for at least 8 weeks before screening, fasting C-peptide concentration≥1.0 ng/ml, age 18-77 years, and BMI≤40 kg/m².

Eligible patients will be enrolled in a 2-week, single-blind, dietary and exercise placebo lead-in period and will receive open-label metformin at their prestudy dose. After the lead-in period, eligible patients will be randomly assigned 1:1:1:1 (permuted blocks stratified by site) to 5 mg, 10 mg or 20 mg gaboxadol or placebo for 24 weeks in addition to their lead-in dose of open-label metformin. Gaboxadol tablets will be identical in appearance to the matched placebo. The primary efficacy outcome will be change from baseline in A1C to week 24. Secondary end points will include change from baseline to week 24 in fasting plasma glucose (FPG), the percentage of patients at the glycemic target (defined as A1C<7.0%), and postprandial glucose (PPG) 3-h area under the curve (AUC) during a 75-g oral glucose tolerance test (OGTT). Per protocol, the OGTT will occur 30 min after administration of study medication. Other efficacy outcomes will include 2-h postprandial plasma glucose (as measured during the OGTT), percentage of patients at glycemic target based on pre-defined A1C and glucose values, and change from baseline to week 24 in fasting and postprandial plasma glucagon, insulin, and C-peptide concentrations; homeostasis model assessment (HOMA)-2-derived indexes of insulin resistance and β-cell function (HOMA-2β); and indexes of insulin sensitivity and β-cell function derived from the OGTT.

Efficacy analyses will be performed on the randomly assigned patient population, consisting of randomly assigned patients who receive at least one dose of study medication and have a baseline and at least one post-baseline measurement. Each gaboxadol group will be compared with the placebo group for changes from baseline to week 24 in continuous end points using an ANCOVA with treatment group as an effect and baseline value as a covariate. Point estimates and 95% CIs for the least-squares mean change within each treatment group as well as the differences in least-squares mean changes between each gaboxadol group and the placebo group at week 24 will be calculated. Sequential testing methodology will be used for secondary efficacy end points. Other continuous efficacy variables will be summarized using descriptive statistics. The percentage of patients achieving a therapeutic glycemic response at week 24 will be compared between each gaboxadol group and the metformin plus placebo group using the Fisher's exact test. Last observation carried forward methodology will be used to handle missing data. Safety analyses will be performed on the treated patient population, consisting of randomly assigned patients who receive at least one dose of study medication.

Example 3

Prospective Assessment of the Efficacy of Gaboxadol and a DPP-4 Inhibitor in Patients with Type 2 Diabetes This study is designed to investigate the efficacy and safety of once-daily gaboxadol administered orally at 5 mg, 10 mg and 20-mg doses and a DPP-4 inhibitor, sitagliptin at 100 mg per day vs. placebo over a 6-month period in treatment-naive patients with type 2 diabetes inadequately controlled with diet and exercise. This will be a multicenter, randomized, four-arm, parallel-group, double-blind, placebo-controlled trial. Patients between 18 and 77 years old with type 2 diabetes inadequately controlled with diet and exercise (HbA1c greater than or equal to 7.0% at screening visit) will be eligible. Patients with a screening HbA1c greater than 7.0% and less than 10.0% will encompass the main treatment cohort (MTC), whereas those with an HbA1c greater than 10.0% and less than 12.0% who otherwise meet all other inclusion and exclusion criteria will be eligible for direct entry into the open-label cohort (OLC). For eligibility, all patients will be required to be treatment naive (defined as never receiving medical treatment for diabetes [insulin and/or oral hypoglycemic medication] for greater than 6 months after original diagnosis, and no oral hypoglycemic medication for more than 3 consecutive days or 7 nonconsecutive days during the 8 weeks prior to screening), have a fasting C-peptide greater than or equal to 1 ng/mL (greater than or equal to 0.33 nmol/L), and a body mass index (BMI) less than or equal to 40 kg/m'.

Following screening, MTC patients will enter a single-blind 2-week dietary and exercise placebo lead-in period. Patients who meet entrance criteria and demonstrate adequate compliance (80 to 120% of prescribed drug consumption) with study medication (placebo) during the lead-in period will qualify for enrollment. Patients will be randomized (1:1:1:1) to oral gaboxadol 5 mg, 10 mg, 20 mg, and oral sitagliptin 100 mg, oral sitagliptin 100 mg alone, or placebo and will be followed for 24 weeks on double-blind study medication. Patients enrolled in the OLC will be entered directly into a 24-week treatment period where they will receive received oral, open-label gaboxadol at a dose of 20 mg in combination with oral sitagliptin 100 mg once daily.

The primary endpoint will be change in HbA1c from baseline to week 24. Secondary endpoints will include change from baseline to week 24 in: (1) fasting plasma glucose (FPG); (2) proportion of patients achieving an HbA1 less than 7.0%; and (3) change from baseline in area under the curve (AUC) from 0 to 180 min for postprandial glucose (PPG) in response to a 75-g oral glucose tolerance test (OGTT). Other prespecified efficacy outcome measures will be PPG change from baseline at 120 min in response to an OGTT and changes from baseline to week 24 in levels of both fasting and postprandial insulin, C-peptide, and glucagon levels. B-Cell function will be measured by homeostasis model assessment (HOMA)-2 and insulin resistance.

Efficacy analyses will be performed on the randomized patients dataset, which will consist of randomized patients who receive at least one dose of study medication and who have a baseline and at least one post-baseline measurement. Each gaboxadol/sitagliptin group and sitagliptin group will be compared with each other and the placebo for changes from baseline to week 24 in continuous variables utilizing an analysis of covariance (ANCOVA) model with treatment group as an effect and baseline value as a covariate. The percentage of patients achieving target HbA1c at week 24 will be compared between each gaboxadol/sitagliptin treatment group vs. sitagliptin monotherapy treatment group vs. placebo, using a two-sided Fisher exact test. Demographic and other baseline characteristics will be summarized using descriptive statistics. Estimated average glucose (eAG) values will be calculated post hoc based on HbA1c values using the following linear regression: $eAG_{mg/dL}=28.7 \times HbA1c-46.7$. Within the framework of the ANCOVA model, point estimates and 95% confidence intervals (CIs) for the absolute and adjusted mean change within each treatment group, as well as for the differences in mean changes between each of the gaboxadol/sitagliptin treatment groups (5 mg, 10 mg, and 20 mg), the sitagliptin monotherapy treatment group and the placebo group, will be calculated. For the primary endpoint, each comparison between a gaboxadol/sitagliptin treatment group, the sitagliptin monotherapy treatment group and the placebo group will be performed at the alpha=0.019 level from Dunnett's adjustment so that the overall type I error rate will be controlled at the 0.05 significance level. Sequential testing methodology will be utilized for secondary efficacy endpoints to adjust for multiplicity and preserve the overall type I error rate within each treatment group at the 0.05 level.

Those skilled in the art will recognize, or be able to ascertain using no more than routine experimentation, many equivalents to the specific embodiments described herein. Such equivalents are intended to be encompassed by the claims.

What is claimed is:

1. A method of treating diabetes comprising administering gaboxadol or a pharmaceutically acceptable salt thereof to a patient in need thereof in an amount effective to lower the patient's HbA1c level by an amount greater than 0.5% as compared to the patient's HbA1c level prior to treatment with gaboxadol or a pharmaceutically acceptable salt thereof.

2. The method of treating diabetes according to claim 1, wherein the diabetes is Type 2 diabetes.

3. The method of treating diabetes according to claim 1, wherein the diabetes is Type 1 diabetes.

4. The method of treating diabetes according to claim 1, wherein the HbA1c level is lowered by an amount greater than 1.0% in the patient as compared to the patient's HbA1c level prior to treatment with gaboxadol or a pharmaceutically acceptable salt thereof.

5. The method of treating diabetes according to claim 1, wherein the gaboxadol or a pharmaceutically acceptable salt thereof is administered in an amount ranging from 0.05 mg to 30.0 mg.

6. The method of treating diabetes according to claim 1, wherein the gaboxadol or a pharmaceutically acceptable salt thereof is administered in combination with one or more hypoglycemic agents selected from the group consisting of a biguanide, a dipeptidyl peptidase-4 (DPP-4) inhibitor, a sulphonylurea, a thiazolidinedione, a glinide, an alpha-glucosidase blocker, an glucagon-like peptide-1 receptor agonist, insulin and an insulin analog.

7. The method of treating diabetes according to claim 6, wherein the combination of the gaboxadol or a pharmaceutically acceptable salt thereof and the one or more hypoglycemic agents provides a therapeutic benefit greater than the additive effect of administering the same dosage of each of the gaboxadol or a pharmaceutically acceptable salt thereof and the hypoglycemic agents alone.

8. A method of treating diabetes comprising administering gaboxadol or a pharmaceutically acceptable salt thereof to a patient in need thereof in an amount effective to lower fasting plasma glucose level in the patient as compared to the patient's fasting plasma glucose level prior to treatment with gaboxadol or a pharmaceutically acceptable salt thereof.

9. The method of treating diabetes according to claim 8, wherein the diabetes is Type 2 diabetes.

10. The method of treating diabetes according to claim 8, wherein the diabetes is Type 1 diabetes.

11. The method of treating diabetes according to claim 8, wherein the patient has an HbA1c level that is lowered by an amount greater than 0.5% as compared to the patient's fasting plasma glucose level prior to treatment with gaboxadol or a pharmaceutically acceptable salt thereof.

12. The method of treating diabetes according to claim 8, wherein the patient has an HbA1c level that is lowered by an amount greater than 1.0% as compared to the patient's fasting plasma glucose level prior to treatment with gaboxadol or a pharmaceutically acceptable salt thereof.

13. The method of treating diabetes according to claim 8, wherein the gaboxadol or a pharmaceutically acceptable salt thereof is administered in an amount ranging from 0.05 mg to 30.0 mg.

14. The method of treating diabetes according to claim 8, wherein the gaboxadol or a pharmaceutically acceptable salt thereof is administered in combination with one or more hypoglycemic agents selected from the group consisting of a biguanide, a dipeptidyl peptidase-4 (DPP-4) inhibitor, a sulphonylurea, a thiazolidinedione, a glinide, an alpha-glucosidase blocker, an glucagon-like peptide-1 receptor agonist, insulin and an insulin analog.

15. The method of treating diabetes according to claim 14, wherein the combination of the gaboxadol or a pharmaceutically acceptable salt thereof and the one or more hypoglycemic agents provides a therapeutic benefit greater than the additive effect of administering the same dosage of each of the gaboxadol or a pharmaceutically acceptable salt thereof and the hypoglycemic agents alone.

* * * * *